US012599614B2

(12) United States Patent
Ng

(10) Patent No.: US 12,599,614 B2
(45) Date of Patent: Apr. 14, 2026

(54) METHODS AND PHARMACEUTICAL COMPOSITIONS FOR THE TREATMENT AND PROPHYLAXIS OF MICROBIAL INFECTIOUS DISEASES AND ASSOCIATED INFLAMMATORY DISORDERS AND FOR THE TREATMENT AND PROPHYLAXIS OF AGING AND ASSOCIATED DISEASES

(71) Applicant: MD VAULT LLC, Lewes, DE (US)

(72) Inventor: Meng Hua Ng, Lewes, DE (US)

(73) Assignee: MD VAULT LLC, Lewes, DE (US)

( * ) Notice: Subject to any disclaimer, the term of this patent is extended or adjusted under 35 U.S.C. 154(b) by 386 days.

(21) Appl. No.: 18/039,236

(22) PCT Filed: Dec. 13, 2021

(86) PCT No.: PCT/IB2021/061653
§ 371 (c)(1),
(2) Date: May 27, 2023

(87) PCT Pub. No.: WO2022/130178
PCT Pub. Date: Jun. 23, 2022

(65) Prior Publication Data
US 2024/0000805 A1 Jan. 4, 2024

Related U.S. Application Data

(60) Provisional application No. 63/139,337, filed on Jan. 20, 2021, provisional application No. 63/124,905, filed on Dec. 14, 2020.

(51) Int. Cl.
*A61K 31/616* (2006.01)
*A61K 31/192* (2006.01)
(Continued)

(52) U.S. Cl.
CPC .......... *A61K 31/616* (2013.01); *A61K 31/192* (2013.01); *A61K 31/495* (2013.01); *A61P 29/00* (2018.01)

(58) Field of Classification Search
CPC .. A61K 31/616; A61K 31/495; A61K 31/192; A61K 31/196; A61K 31/205;
(Continued)

(56) References Cited

U.S. PATENT DOCUMENTS

2004/0067914 A1  4/2004  Wechter et al.
2009/0258064 A1  10/2009  Newell et al.
(Continued)

FOREIGN PATENT DOCUMENTS

KR      20160046138 A  *  4/2016
WO    WO 2019 /178472 A1 *  9/2019

*Primary Examiner* — Taylor V Oh
(74) *Attorney, Agent, or Firm* — PATENTFILE, LLC; Bradley C. Fach; Steven R. Kick

(57) ABSTRACT

A pharmaceutical composition and method are provided which may be used for the treatment and prevention of various infections, diseases, and conditions. Preferably, the composition and method may be used for preventing and treating of aging and aging associated disease and its use (or method). Preferably, the composition and method may be used for treating and prophylaxis of microbial infectious diseases and associated inflammatory disorders and its use (or method). The pharmaceutical composition according to the invention includes a therapeutic agent X or a pharmaceutically acceptable salt thereof; a therapeutic agent Y or a pharmaceutically acceptable salt thereof; and at least one pharmaceutically acceptable excipient, in which the therapeutic agent X is a non-steroidal anti-inflammatory drug and the therapeutic agent Y is a fatty acid oxidation inhibitor.

9 Claims, 44 Drawing Sheets

(51) Int. Cl.
    *A61K 31/495*         (2006.01)
    *A61P 29/00*          (2006.01)

(58) Field of Classification Search
    CPC .. A61K 31/336; A61K 31/415; A61K 31/444;
               A61K 45/06; A61P 29/00; A61P 31/10;
                     A61P 39/06; Y02A 50/30
    USPC ........................................................ 514/165
    See application file for complete search history.

(56) References Cited

U.S. PATENT DOCUMENTS

2011/0048980 A1    3/2011  Seman
2016/0346309 A1   12/2016  Munger et al.

* cited by examiner

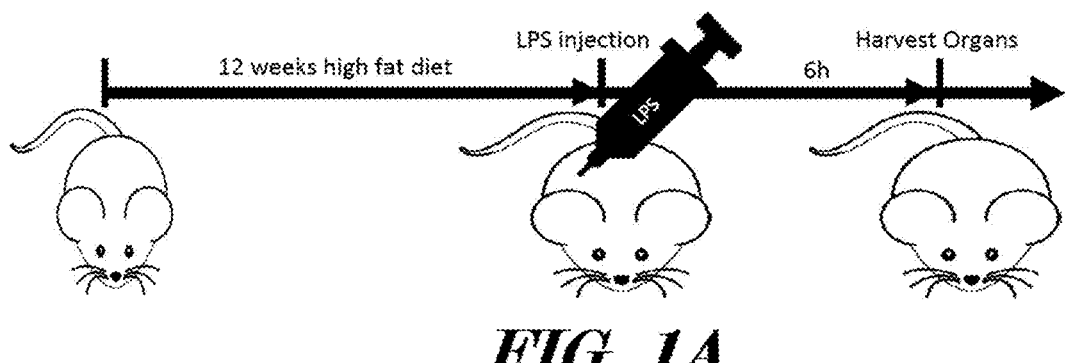
*FIG. 1A*
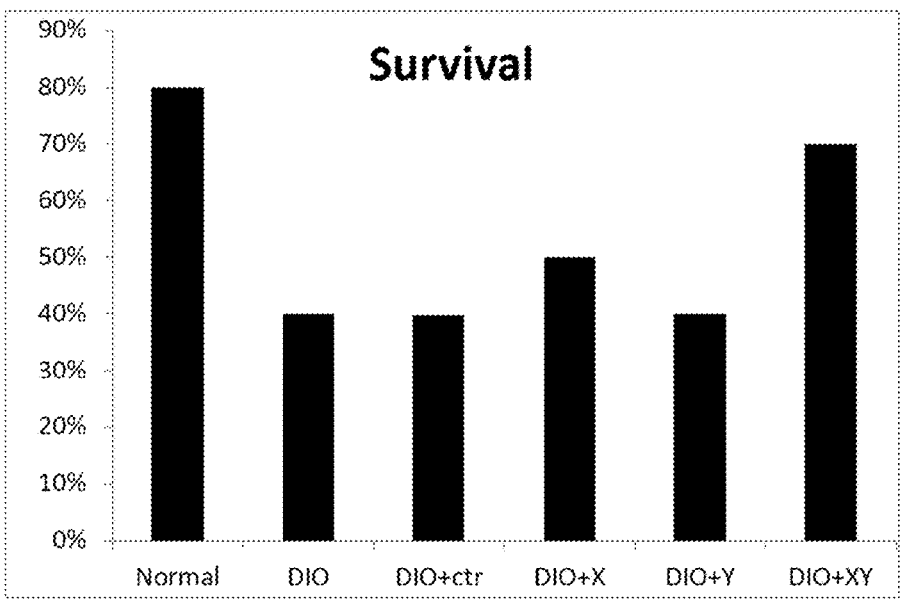
*FIG. 1B*
*FIG. 1C*

ITGB3

Down:
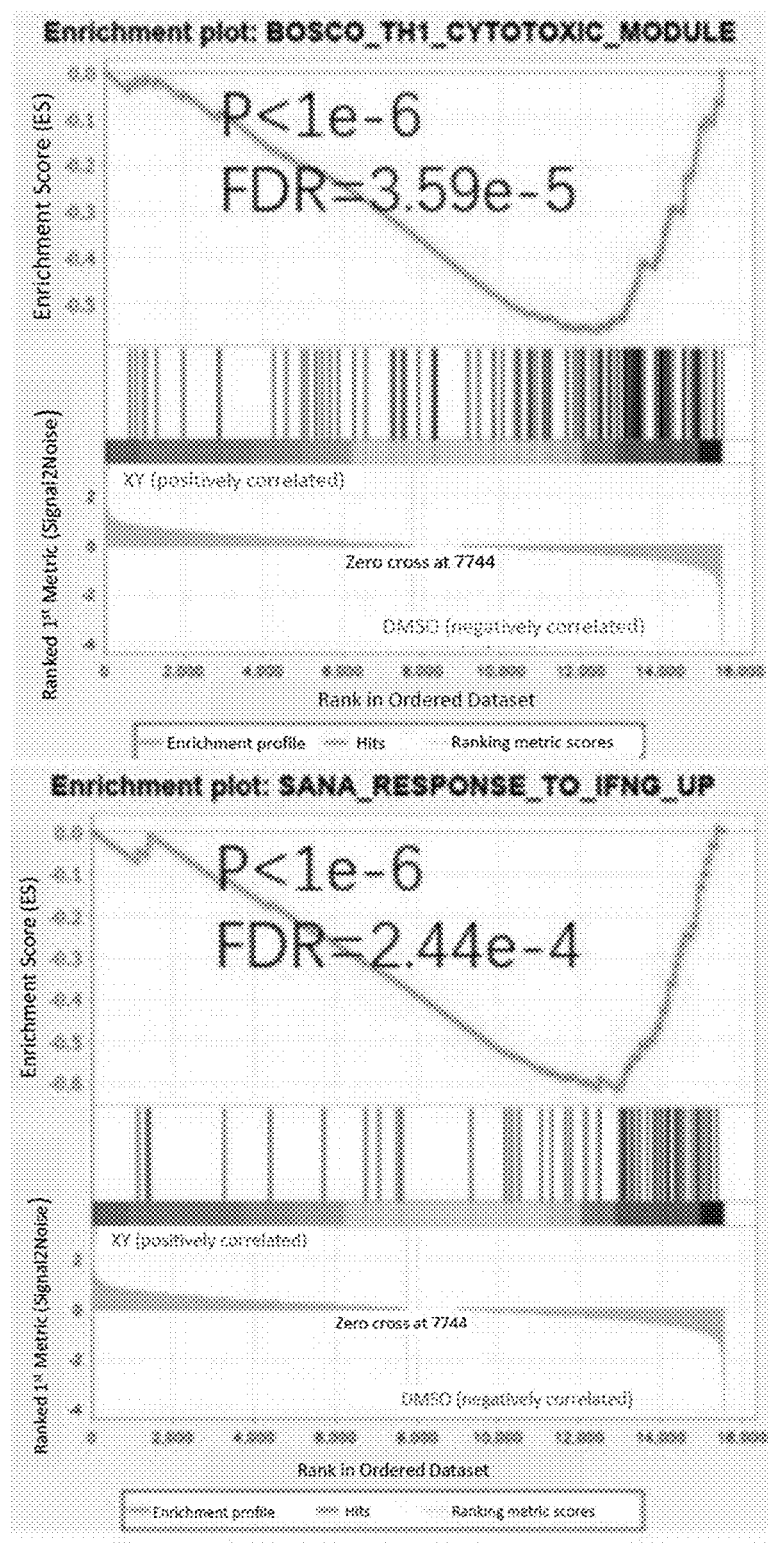
XY --| Th1
*FIG. 18A*

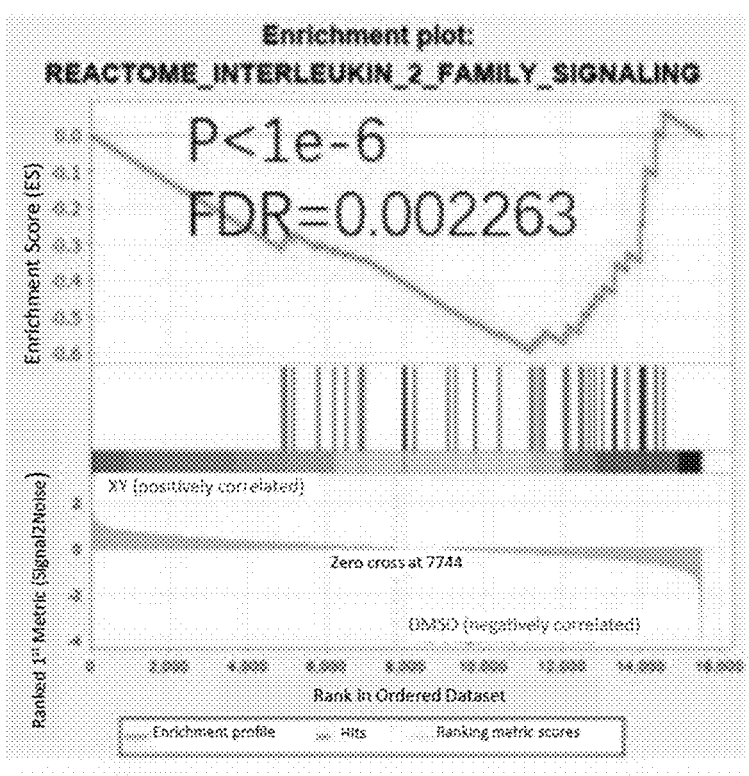
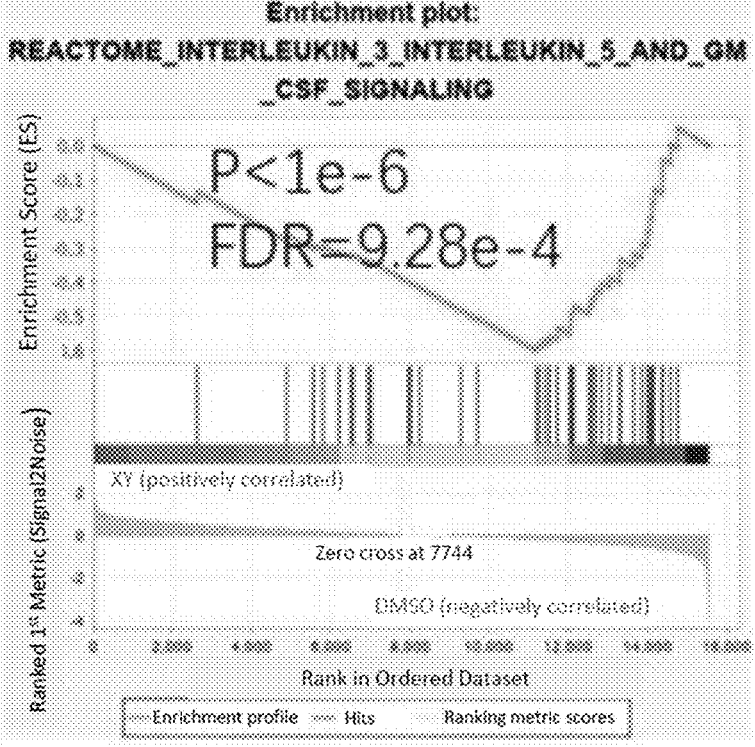
XY --| Th1, Th17, pan-Th
*FIG. 18B*

Up:
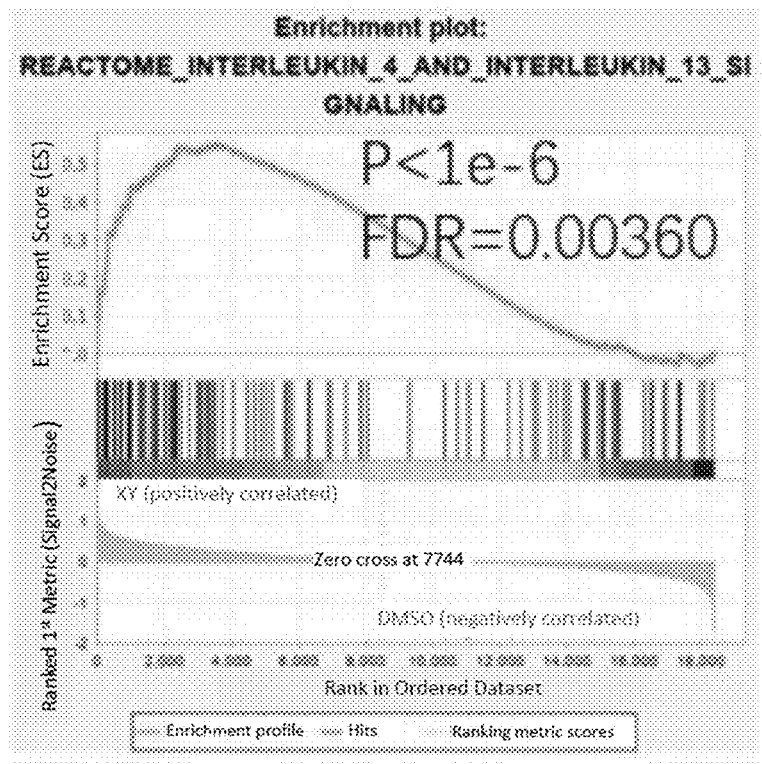
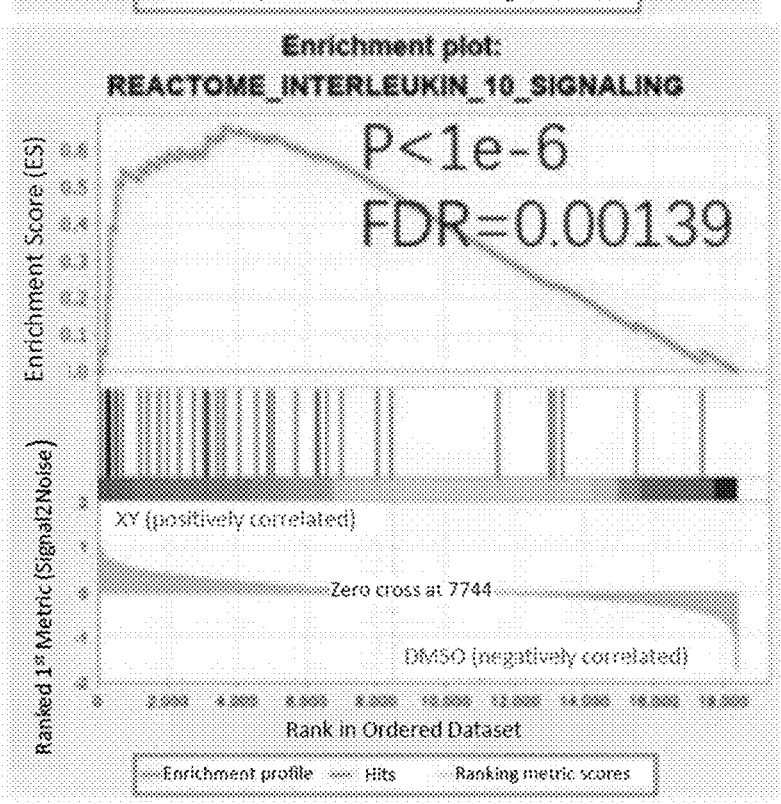
XY → Th2 & Treg
*FIG. 18C*

Ki67/DAPI

Islets fibrosis

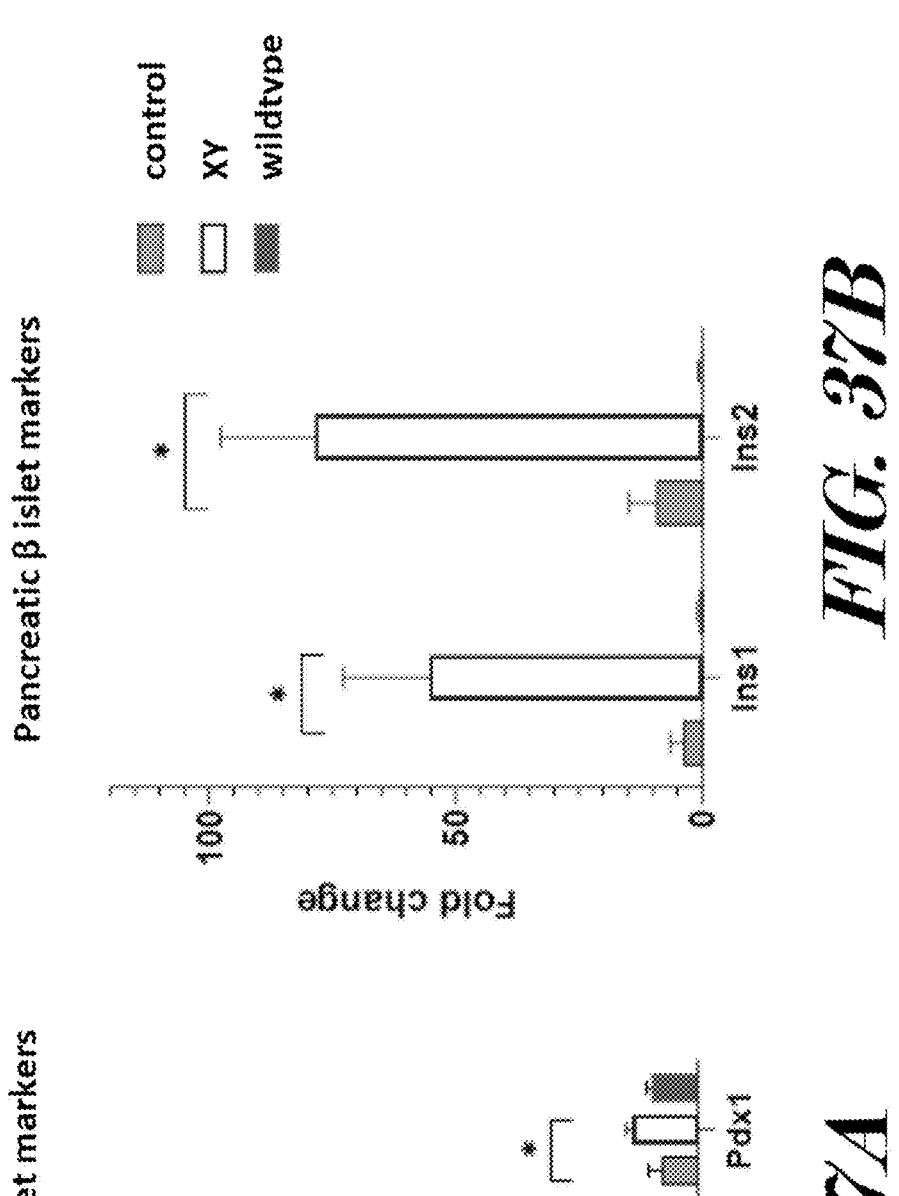

Day 1

Day 64

*FIG. 38*

|      | Acyclic | Cyclic |
|------|---------|--------|
| ctr  | 10      | 0      |
| X    | 10      | 0      |
| Y    | 10      | 0      |
| XY   | 3       | 7      |

METHODS AND PHARMACEUTICAL COMPOSITIONS FOR THE TREATMENT AND PROPHYLAXIS OF MICROBIAL INFECTIOUS DISEASES AND ASSOCIATED INFLAMMATORY DISORDERS AND FOR THE TREATMENT AND PROPHYLAXIS OF AGING AND ASSOCIATED DISEASES

CROSS REFERENCE TO RELATED APPLICATIONS

This Application is a 35 U.S.C. 371 National Stage Entry of International Application No. PCT/IB2021/061653 filed on Dec. 13, 2021, which claims priority to and the benefit of the filing date of U.S. Provisional Application No. 63/124, 905, filed on Dec. 14, 2020, entitled "METHODS AND COMPOSITIONS FOR THE TREATMENT AND PROPHYLAXIS OF MICROBIAL INFECTIOUS DISEASES AND ASSOCIATED INFLAMMATORY DISORDERS", which is hereby incorporated by reference in its entirety. This application also claims priority to and the benefit of the filing date of U.S. Provisional Application No. 63/139,337, filed on Jan. 20, 2021, entitled "METHODS AND COMPOSITIONS FOR THE TREATMENT AND PROPHYLAXIS OF AGING AND ASSOCIATED DISEASES", which is hereby incorporated by reference in its entirety.

FIELD OF THE INVENTION

This patent specification relates to the field of treatment and prevention of diseases and infections. More specifically, this patent specification relates to the use of small molecules to prevent or treat aging and associated diseases and to the use of small molecules prevent or treat microbial infection.

BACKGROUND

There are many diseases and infections which affect the humans and other mammals. This includes infectious diseases and associated inflammatory disorders and also aging and associated diseases.

Microbial infectious disease is the combinatorial process of invasion of infectious agents into the organism, the replication of these agents and the reaction of host tissue against these agents, including inflammation, adaptive immune responses and sometimes a cytokine storm. Examples of microbes include viruses, bacteria, fungi, protozoans and parasites. Microbes replicate inside host cells and can produce toxins that cause disease. Microbial infections often show different degrees of severity in different infected persons. In mild cases, infections can be manifested as fever, chills, fatigue, cough, diarrhea and other symptoms, and severe cases can be manifested as dyspnea, increased heart rate, heart fibrillations, chest pain, acute lung injury (ALI), acute respiratory distress syndrome (ARDS), cytokine release syndrome (CRS), thrombosis, tissue inflammation, tissue damage, acute organ failure, sepsis, and even death. It has been discussed that the severity of microbial infections is heavily dependent on host responses. Hence, it will be of great importance to target microbial infections by modulating the internal environment of the host, by modulating systems endogenous to the host.

As mentioned, microbial infection can be caused by viruses. Virus infections can be caused by a DNA virus or an RNA virus such as members of the Myoviridae, Podoviridae, Siphoviridae, Alloherpesviridae, Herpesviridae (including human herpes virus, and Varicella zoster virus), Malocoherpesviridae, Lipothrixviridae, Rudiviridae, Adenoviridae, Ampullaviridae, Ascoviridae, Asfarviridae (including African swine fever virus), Baculoviridae, Cicaudaviridae, Clavaviridae, Corticoviridae, Fuselloviridae, Globuloviridae, Guttaviridae, Hytrosaviridae, Iridoviridae, Maseilleviridae, Mimiviridae, Nudiviridae, Nimaviridae, Pandoraviridae, Papillomaviridae, Phycodnaviridae, Plasmaviridae, Polydnaviruses, Polyomaviridae (including Simian virus 40, JC virus, BK virus), Poxviridae (including Cowpox and smallpox), Sphaerolipoviridae, Tectiviridae, Turriviridae, Dinodnavirus, Salterprovirus, Rhizidovirus, Coronaviridae, Picornaviridae, Caliciviridae, Flaviviridae, Togaviridae, Bornaviridae, Filoviridae, Paramyxoviridae, Pneumoviridae, Rhabdoviridae, Arenaviridae, Bunyaviridae, Orthomyxoviridae, or Deltavirus. A viral infection may further be caused by a Coronavirus, Poliovirus, Rhinovirus, Hepatitis A, Hepatitis B virus, Norwalk virus, Yellow fever virus, West Nile virus, human immunodeficiency virus, Hepatitis C virus, Dengue fever virus, Zika virus, Rubella virus, Ross River virus, Sindbis virus, Chikungunya virus, Borna disease virus, Ebola virus, Marburg virus, Measles virus, Mumps virus, Nipah virus, Hendra virus, Newcastle disease virus, Human respiratory syncytial virus, Rabies virus, Lassa virus, Hantavirus, Crimean-Congo hemorrhagic fever virus, Influenza, or Hepatitis D virus.

Severity of viral infection can be divided into mild, moderate, severe, and critically ill according to clinical manifestations. Current anti-viral therapies include antibody cocktails or drugs targeting processes critical to the life cycles of the virus such as viral entry, viral uncoating, viral replication, viral synthesis, viral assembly, or viral release. These aforementioned strategies tend to target a particular virus or particular class of virus, hence limiting their application in the face of a different viral outbreak.

Ageing is associated with a progressive degeneration of the tissues, which has a negative impact on the structure and function of vital organs and is among the most important known risk factors for most chronic diseases. Given the proportion of the world's population aged >60 years doubles over the next four decades, the increased incidences of chronic age-related diseases will place a huge burden on healthcare resources.

Today, we are beginning to understand that aging is a ubiquitous complex phenomenon that results from environmental, stochastic, genetic, and epigenetic events in different cells and tissues and their interactions throughout life. A pervasive feature of aging tissues and age-related diseases is chronic inflammation. "Inflammaging" describes the low-grade, chronic, systemic inflammation in aging, in the absence of overt infection ("sterile" inflammation), and is a highly significant risk factor for both morbidity and mortality in the elderly people. There is overwhelming epidemiological evidence that a state of mild inflammation, revealed by elevated levels of inflammatory biomarkers is associated and predictive of many aging phenotypes—for example, changes in body composition, energy production and utilization, metabolic homeostasis, immune senescence, and neuronal health.

Targeting pathways that control age-related inflammation across multiple systems may therefore be beneficial in old people or in treating aging related disorders or syndromes.

Therefore, a need exists for novel methods and compositions for the treatment and prophylaxis of microbial infectious diseases and associated inflammatory disorders. A need also exists for novel methods and compositions for the treatment and prophylaxis of aging and associated diseases.

BRIEF SUMMARY OF THE INVENTION

The present application provides pharmaceutical compositions and methods of using a drug combination which may be used to treat and prevent various aging related disorders and syndromes and which may also be used to improve the host response, for prophylaxis and treatment of infectious diseases and their associated inflammatory disorders.

According to one aspect consistent with the principles of the invention, a pharmaceutical composition is provided which may be used for preventing and treating of infectious disease. According to another aspect, the pharmaceutical composition may be used for preventing and treating of aging and aging associated disease.

In some embodiments, the pharmaceutical composition may comprise a therapeutic agent X or a pharmaceutically acceptable salt thereof; a therapeutic agent Y or a pharmaceutically acceptable salt thereof; and at least one pharmaceutically acceptable excipient, in which the therapeutic agent X is a non-steroidal anti-inflammatory drug and the therapeutic agent Y is a fatty acid oxidation inhibitor. The pharmaceutical composition according to the invention may be used in a method of treating one or more conditions in a subject in need thereof, the conditions including the prevention and treatment of infectious disease and the prevention and treatment of aging associated diseases and syndromes. A method of treating a condition in a subject in need may comprise administering to the subject an effective amount of the pharmaceutical composition that comprises a therapeutic agent X or a pharmaceutically acceptable salt thereof; a therapeutic agent Y or a pharmaceutically acceptable salt thereof; and at least one pharmaceutically acceptable excipient, in which the therapeutic agent X is a non-steroidal anti-inflammatory drug and the therapeutic agent Y is a fatty acid oxidation inhibitor.

In further embodiments, in the pharmaceutical composition, the therapeutic agent X and the therapeutic agent Y are included in a single dosage form.

In further embodiments, in the pharmaceutical composition, the therapeutic agent X and the therapeutic agent Y exist in separate dosage forms.

In further embodiments, the therapeutic agent X is selected from at least one of the COX inhibitors, salicylates, ibuprofen, indomethacin, flurbiprofen, phenoxyibuprofen, naproxen, nabumetone, piroxicam, butazone, diclofenac, fenoprofen, ketoprofen, ketorolac, tetrachlorofenoic acid, sulindac and tometine. In some embodiments, agent X is a salicylate or a derivative thereof. In some embodiments, agent X is 2-acetyloxybenzoic acid.

In further embodiments, the therapeutic agent Y is selected from at least one of the CPT inhibitors, carnitine biosynthesis inhibitors, 3-ketoacyl-coenzyme A thiolase inhibitors, etomoxir, oxfenicine, perhexiline, mildronate, trimetazidine, ethoxylcarnitine, aminocarnitine or a phosphonyloxy derivative of carnitine. In some embodiments, agent Y is 1-[(2,3,4-trimethoxyphenyl)methyl]piperazine.

In some embodiments, the weight ratio of the therapeutic agent X and the therapeutic agent Y of the pharmaceutical composition may be between 1:1 to 10:1, including 1:1, 2:1, 3:1, 4:1, 5:1, 6:1, 7:1, 8:1, 9:1, or 10:1. In further embodiments, the mass ratio of the therapeutic agent X and the therapeutic agent Y may be between 1:1 to 10:1, including 1:1, 2:1, 3:1, 4:1, 5:1, 6:1, 7:1, 8:1, 9:1, or 10:1.

In some embodiments, the pharmaceutical composition may be administered in an oral dosage form. In further embodiments, the pharmaceutical composition may be administered in injection form.

In some embodiments, the therapeutic agent X and the therapeutic agent Y are administered simultaneously. In some embodiments, the therapeutic agent X and the therapeutic agent Y are included in a single dosage form. In some embodiments, the single drug dosage form is an oral dosage form. In further embodiments, the single drug dosage form is an injection form.

In some embodiments, the therapeutic agent X and the therapeutic agent Y are administered respectively. In some embodiments, the therapeutic agent X is administered prior to the therapeutic agent Y. In some embodiments, the therapeutic agent X is administered after the therapeutic agent Y. In some embodiments, therapeutic agent X and therapeutic agent Y are administered orally, respectively. In some embodiments, therapeutic agent X and therapeutic agent Y are administered by injection, respectively.

BRIEF DESCRIPTION OF THE DRAWINGS

Some embodiments of the present invention are illustrated as an example and are not limited by the figures of the accompanying drawings, in which like references may indicate similar elements and in which:

FIG. 1A-FIG. 1A shows the scheme for microbial disease modeling and drug dosing.

FIG. 1B-FIG. 1B shows the drug combination X and Y prevents microbial LPS-induced death in mice.

FIG. 1C-FIG. 1C shows the drug combination X and Y ameliorates microbial LPS-induced lung inflammation in mice.

FIG. 18A-FIG. 18A shows that the drug combination X and Y reverses inflammaging-associated and immunosenescence-associated gene signatures.

FIG. 18B-FIG. 18B shows that the drug combination X and Y reverses inflammaging-associated and immunosenescence-associated gene signatures.

FIG. 18C-FIG. 18C shows that the drug combination X and Y reverses inflammaging-associated and immunosenescence-associated gene signatures.

-FIG. 37A shows that drug combination X and Y increased β islet cell growth and proliferation according to qRT-PCR for Pax6, Mafa, and Pdx1 using primers from Origene, thereby promoting pancreatic β islet regeneration.

FIG. 37B-FIG. 37B shows that drug combination X and Y increased β islet cell growth and proliferation according to qRT-PCR for Ins1 and Ins2 using primers from Origene, thereby promoting pancreatic β islet regeneration.

FIG. 38-FIG. 38 shows that drug combination X and Y promoted both aged hair regeneration and wound healing by 64 days.

DETAILED DESCRIPTION OF THE INVENTION

Figure 2:
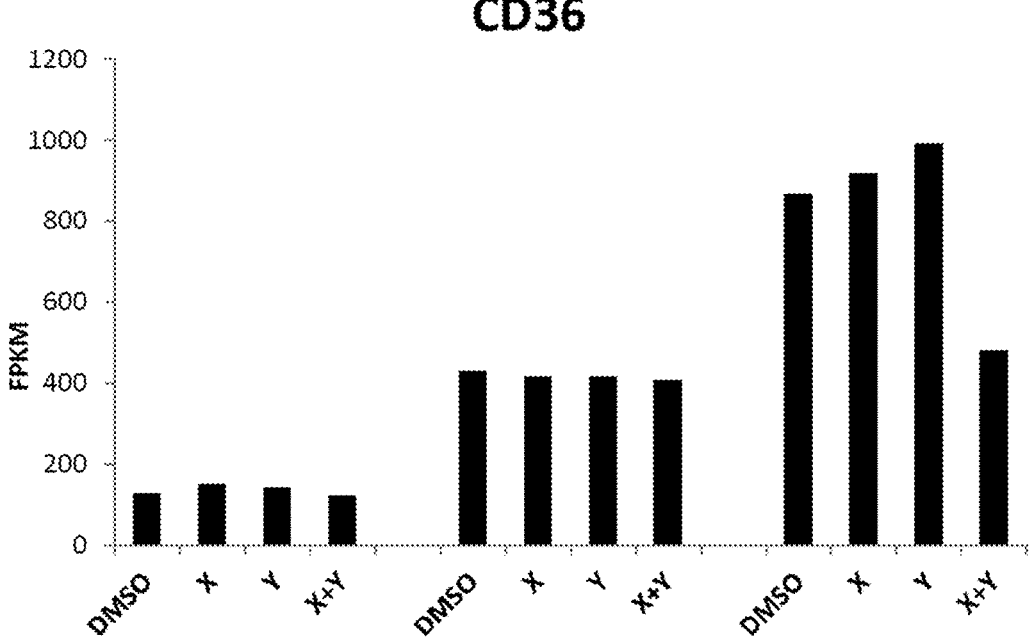
FIG. 2-FIG. 2 shows that the drug combination X and Y decreases expression of the hepatitis C virus coreceptor CD36.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

The term "microbe" refers to tiny organisms that include virus, bacteria, fungi, protozoa, algae, amoebas, and slime molds and other potential disease-causing organisms.

The term "infection" refers to the invasion of an organism's body tissues by disease-causing agents, their multiplication, and the reaction of host tissues to the infectious agents and the toxins they produce.

The term "aging-associated diseases" refers to diseases where incidences of diseases increase with age and diseases that are degenerative.

The term "inflammaging" refers to the invasion of an organism's body tissues by disease-causing agents, their multiplication, and the reaction of host tissues to the infectious agents and the toxins they produce.

The term "NSAID" or "nonsteroidal anti-inflammatory drugs" are used herein interchangeably to refer to members of a drug class that inhibits the activity of cyclooxygenase enzymes (COX) to reduce pain, decrease fever and prevent drug clots. It is known in the art that not all inflammatory disorders can be treated with NSAIDs.

The terms "fatty acid oxidation" and "FAO" are used herein interchangeably to refer to the biochemical process of breaking down a fatty acid into acetyl-CoA units. In some embodiments, the FAO is in the mitochondria of a cell. In some embodiments, the FAO is in the peroxisome of a cell. In some embodiments, the FAO rate-limiting step is catalyzed by carnitine palmitoyltransferase (CPT).

As used herein, "treatment" or "treating" is an approach for obtaining beneficial or desired results including clinical results. For purposes of this invention, beneficial or desired clinical results include, but are not limited to, one or more of the following: decreasing one or more symptoms resulting from the disease, diminishing the extent of the disease, stabilizing the disease or condition (e.g., preventing or delaying the worsening of the disease or condition), preventing or delaying the spread of the disease or condition, preventing or delaying the occurrence or recurrence of the disease or condition, delaying or slowing the progression of the disease or condition, ameliorating the disease state, providing a remission (whether partial or total) of the disease or condition, decreasing the dose of one or more other medications required to treat the disease or condition, delaying the progression of the disease or condition, increasing the quality of life, and/or prolonging survival. Also encompassed by "treatment" is a reduction of pathological consequence of the disease or condition. The methods of the present application utilize any one or more of these aspects of treatment.

As used herein, the term "prevention" and "prophylaxis" refers to a measure for preventing or protecting against a disease, disorder or condition from occurring in subjects that are at risk of disease but has not yet been diagnosed. Prevention (and effective preventive doses) or prophylaxis can be demonstrated in population studies, e.g., relative to the untreated control subjects, an effective amount to prevent or protect against a given disease or medical condition is an effective way to reduce the incidence in the treated subjects.

The terms "individual," "subject" and "patient" are used interchangeably herein to describe a mammal, including humans. An individual includes, but is not limited to, human, bovine, ovine, porcine, equine, feline, canine, rodent, or primate. In some embodiments, the individual is human. In some embodiments, an individual suffers from a disease or condition. In some embodiments, the individual is in need of treatment.

As is understood in the art, an "effective amount" refers to an amount of a composition sufficient to produce a desired therapeutic outcome. For therapeutic use, beneficial or desired results include, e.g., decreasing one or more symptoms resulting from the disease or condition (biochemical, histologic and/or behavioral), including its complications and intermediate pathological phenotypes presented during development of the disease or condition, increasing the quality of life of those suffering from the disease or condition, decreasing the dose of other medications required to treat the disease or condition, enhancing effect of another medication, delaying the progression of the disease or condition, and/or prolonging survival of patients.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

The terms "X and Y" or "X+Y" or "XY" are used interchangeably herein to refer to a combination comprising of both therapeutic agent X or pharmaceutically acceptable salts thereof and therapeutic agent Y or pharmaceutically acceptable salts thereof.

Both therapeutic agent X or pharmaceutically acceptable salts thereof and therapeutic agent Y can either be administered together or administered one after another.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

As used in this application, the term "about" or "approximately" refers to a range of values within plus or minus 20% of the specified number. Additionally, as used in this application, the term "substantially" means that the actual value is within about 10% of the actual desired value, particularly within about 5% of the actual desired value and especially within about 1% of the actual desired value of any variable, element or limit set forth herein.

New methods and compositions for the treatment and prophylaxis of aging and associated diseases and for the treatment and prophylaxis of microbial infectious diseases and associated inflammatory disorders are discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

The present invention will now be described by example and through referencing the appended figures representing preferred and alternative embodiments. According to an embodiment of the present invention a composition of matter is provided which may be used to treat various diseases, conditions, and infections. In some embodiments, the composition of matter may comprise a pharmaceutical composition having a therapeutic agent X or a pharmaceutically acceptable salt thereof; a therapeutic agent Y or a pharmaceutically acceptable salt thereof; and at least one pharmaceutically acceptable excipient, in which the therapeutic agent X is a non-steroidal anti-inflammatory drug and the therapeutic agent Y is a fatty acid oxidation inhibitor. In some embodiments, therapeutic agent X is a salicyclic acid or derivative thereof (e.g. salsalate). In some embodiments, therapeutic agent X is 2-acetyloxybenzoic acid. In some embodiments, therapeutic agent Y is 1-[(2,3,4-trimethoxyphenyl)methyl]piperazine. According to another embodiment of the present invention a method of treating one or more conditions in a subject in need thereof, the conditions including the prevention and treatment of infectious disease and the prevention and treatment of aging associated diseases and syndromes is provided. A method of treating a condition in a subject in need may comprise administering to the subject an effective amount of the pharmaceutical composition that comprises a therapeutic agent X or a pharmaceutically acceptable salt thereof; a therapeutic agent Y or a pharmaceutically acceptable salt thereof; and at least one pharmaceutically acceptable excipient, in which the therapeutic agent X is a non-steroidal anti-inflammatory drug and the therapeutic agent Y is a fatty acid oxidation inhibitor.

The pharmaceutical composition and method comprising the administration of the pharmaceutical composition according to the invention is able to effectively treat or prevent microbial infections.

In some embodiments, the pharmaceutical composition comprising therapeutic agent X or a pharmaceutically acceptable salt thereof and a therapeutic agent Y or a pharmaceutically acceptable salt thereof may effectively prevent and or treat viral infections by modulating the immune system. In some preferred embodiments, the pharmaceutical composition comprising therapeutic agent X or a pharmaceutically acceptable salt thereof and a therapeutic agent Y or a pharmaceutically acceptable salt thereof may regulate immunomodulatory factors such as but not limited to: ACVR1, ACVR1B, ACVR2A, ACVR2B, ACVRL1, AMH, AMHR2, BMP2, BMP7, BMPR1A, BMPR1B, BMPR2, CCL11, CCL15, CCL17, CCL19, CCL2, CCL20, CCL21, CCL22, CCL23, CCL24, CCL27, CCL28, CCL3, CCL4, CCL5, CCL7, CCL8, CCR1, CCR10, CCR2, CCR3,

11

CCR4, CCR5, CCR6, CCR7, CCR8, CCR9, CD27, CD40, CD40LG, CD70, CLCF1, CNTF, CNTFR, CRLF2, CSF1, CSF1R, CSF2, CSF2RA, CSF2RB, CSF3, CSF3R, CTF1, CX3CL1, CX3CR1, CXCL10, CXCL11, CXCL12, CXCL13, CXCL14, CXCL16, CXCL6, CXCL9, CXCR1, CXCR2, CXCR3, CXCR4, CXCR5, CXCR6, EDA, EDA2R, EDAR, EGF, EGFR, EPO, EPOR, FAS, FASLG, FLT1, FLT3, FLT3LG, FLT4, GDF5, GH1, GHR, HGF, IFNA1, IFNA10, IFNA17, IFNA2, IFNA4, IFNA5, IFNA6, IFNA7, IFNA8, IFNAR1, IFNAR2, IFNB1, IFNE, IFNG, IFNGR1, IFNGR2, IFNK, IFNL3, IFNLR1, IL10, IL10RA, IL10RB, IL11, IL11RA, IL12A, IL12B, IL12RB1, IL12RB2, IL13, IL13RA1, IL15, IL15RA, IL17A, IL17B, IL17RA, IL17RB, IL18, IL18R1, IL18RAP, IL19, ILIA, IL1B, IL1R1, IL1R2, IL1RAP, IL2, IL20, IL20RA, IL20RB, IL21, IL21R, IL22, IL22RA1, IL22RA2, IL23A, IL23R, IL24, IL25, IL2RA, IL2RB, IL2RG, IL3, IL4, IL4R, IL5, IL5RA, IL6, IL6R, IL6ST, IL7, IL7R, IL9, IL9R, INHBA, INHBB, INHBC, INHBE, KDR, KIT, KITLG, LEP, LEPR, LIF, LIFR, LTA, LTB, MET, MPL, NGFR, OSM, OSMR, PDGFA, PDGFB, PDGFC, PDGFRA, PDG-FRB, PLEKHO2, PPBP, PRL, PRLR, RELT, TGFB1, TGFB2, TGFB3, TGFBR1, TGFBR2, TNFA, TNFRSF10B, TNFRSF10C, TNFRSF10D, TNFRSF11A, TNFR5F11B, TNFRSF12A, TNFRSF13B, TNFRSF13C, TNFRSF14, TNFRSF17, TNFRSF18, TNFRSF19, TNFRSF1A, TNFRSF1B, TNFRSF21, TNFRSF25, TNFRSF4, TNFRSF8, TNFRSF9, TNFSF10, TNFSF11, TNFSF12, TNFSF13, TNFSF13B, TNFSF14, TNFSF15, TNFSF18, TNFSF4, TNFSF8, TNFSF9, TPO, TSLP, VEGFA, VEGFB, VEGFC, VEGFD, XCL1, XCR1. In another aspect, the invention provides a method of treating a condition in a subject in need by regulating one or more of the above immunomodulatory factors, the method comprising administering to the subject an effective amount of the pharmaceutical composition.

In some embodiments, the pharmaceutical composition comprising therapeutic agent X or a pharmaceutically acceptable salt thereof and a therapeutic agent Y or a pharmaceutically acceptable salt thereof may effectively prevent and or treat viral infections by modulating inflammation. In some preferred embodiments, the pharmaceutical composition comprising therapeutic agent X or a pharmaceutically acceptable salt thereof and a therapeutic agent Y or a pharmaceutically acceptable salt thereof may decrease the expression of factors such as but not limited to: AKT1, AKT2, AKT3, BTK, CASP8, CCL3, CCL4, CCL5, CD14, CD180, CD40, CD80, CD86, CHUK, CISH, CTNNAL1, CUEDC2, CXCL10, CXCL11, CXCL8, CXCL9, CYLD, FADD, FBXW5, FOS, GM-CSF, IFNA1, IFNA10, IFNA13, IFNA14, IFNA16, IFNA17, IFNA2, IFNA21, IFNA4, IFNA5, IFNA6, IFNA7, IFNA8, IFNAR1, IFNAR2, IFNB1, IFNG, IKBKB, IKBKE, IKBKG, IL12A, IL12B, IL18, IL1B, IL6, IL8, IRAK1, IRAK2, IRAK3, IRAK4, IRF3, IRF5, IRF7, JUN, LBP, LY96, MAP2K1, MAP2K2, MAP2K3, MAP2K4, MAP2K6, MAP2K7, MAP3K7, MAP3K8, MAPK1, MAPK10, MAPK11, MAPK12, MAPK13, MAPK14, MAPK3, MAPK8, MAPK9, MBL2, MIR105-1, MIR6502, MIR718, MIR98, MIRLET7E, MIRLET7I, MLST8, MYD88, NFKB1, NFKB2, NFKBIA, OTUD5, PELI1, PELI2, PELI3, PIK3CA, PIK3CB, PIK3CD, PIK3CG, PIK3R1, PIK3R2, PIK3R3, PIK3R5, PLK1, PROBE, PTPN6, RAC1, RBCK1, RELA, RIPK1, RNF216, RNF31, RNF41, SARM1, SFTPA2, SFTPD, SIGIRR, SMAD6, SOCS1, SPP1, SQSTM1, STAT1, SYK, TAB1, TAB2, TABS, TBK1, TICAM1, TICAM2, TIFA, TIRAP, TLR1, TLR2, TLR3, TLR4, TLR5, TLR6, TLR7,

12

TLR8, TLR9, TMED7, TNFA, TNFAIP3, TOLLIP, TRAF3, TRAF6, TRAFD1, TREM1, USP7, ZMYND11. In another aspect, the invention provides a method of treating a condition in a subject in need by decreasing the expression of one or more of the above factors, the method comprising administering to the subject an effective amount of the pharmaceutical composition.

In some embodiments, the pharmaceutical composition comprising therapeutic agent X or a pharmaceutically acceptable salt thereof and a therapeutic agent Y or a pharmaceutically acceptable salt thereof may effectively prevent and or treat viral infections by decreasing a viral receptor. In some preferred embodiments, the pharmaceutical composition comprising therapeutic agent X or a pharmaceutically acceptable salt thereof and a therapeutic agent Y or a pharmaceutically acceptable salt thereof may decrease the expression of factors such as but not limited to: ACE2, CD4, CD36, CD81, CLDN1, CXCR4, DPP4, HAVCR1, HAVCR2, ITGAV, ITGB1, ITGB3, ITGB5, ITGB6, MAG, SLC1A4, SLC1A5, SLC7A1, SLC20A1, SLC20A2. In another aspect, the invention provides a method of treating a condition in a subject in need by decreasing the expression of one or more of the above factors, the method comprising administering to the subject an effective amount of the pharmaceutical composition.

In some embodiments, the pharmaceutical composition comprising therapeutic agent X or a pharmaceutically acceptable salt thereof and a therapeutic agent Y or a pharmaceutically acceptable salt thereof may effectively prevent and or treat microbial infections caused by a virus, a bacterium, a fungus, a protozoan, or a parasite. In further embodiments, a method of effectively preventing and/or treating microbial infections caused by a virus, a bacterium, a fungus, a protozoan, or a parasite, may comprise administering to the subject an effective amount of the pharmaceutical composition.

In embodiments where the infection is viral, it may be caused by a DNA virus. In some specific embodiments, the DNA virus may include, but is not necessarily limited to members of the Adenoviridae, Papovaviridae, Parvoviridae, Anelloviridae, Pleolipoviridae, Myoviridae, Podoviridae, Siphoviridae, Alloherpesviridae, Herpesviridae (including human herpes virus, and Varicella zoster virus), Malocoherpesviridae, Lipothrixviridae, Rudiviridae, Adenoviridae, Ampullaviridae, Ascoviridae, Asfarviridae (including African swine fever virus), Baculoviridae, Cicaudaviridae, Clavaviridae, Corticoviridae, Fuselloviridae, Globuloviridae, Guttaviridae, Hytrosaviridae, Iridoviridae, Maseilleviridae, Mimiviridae, Nudiviridae, Nimaviridae, Pandoraviridae, Papillomaviridae, Phycodnaviridae, Plasmaviridae, Polydnaviruses, Polyomaviridae (including Simian virus 40, JC virus, BK virus), Poxviridae (including Cowpox and smallpox), Sphaerolipoviridae, Tectiviridae, Turriviridae, Dinodnavirus, Salterprovirus, or Rhizidovirus.

A viral infection may also be caused by a double-stranded RNA virus, a positive sense RNA virus, a negative sense RNA virus, a retrovirus, or a combination thereof. A viral infection may further be caused by a Coronaviridae virus, a Picornaviridae virus, a Reoviridae virus, a Caliciviridae virus, a Flaviviridae virus, a Togaviridae virus, a Bornaviridae virus, a Filoviridae virus, a Paramyxoviridae virus, a Pneumoviridae virus, a Rhabdoviridae virus, an Arenaviridae, a Bunyaviridae virus, an Astroviridae virus an Orthomyxoviridae virus, an Arteriviridae virus, a Hepeviridae virus, a Retroviridae virus, a Caulimoviridae virus, a Hepadnaviridae virus or a Deltavirus. A viral infection may further be caused by a Coronavirus, Poliovirus, Rhinovirus, Hepatitis A, Norwalk virus, Yellow fever virus, West Nile virus, Hepatitis C virus, Dengue fever virus, Zika virus, Rubella virus, Ross River virus, Sindbis virus, Chikungunya virus, Borna disease virus, Ebola virus, Marburg virus, Measles virus, Mumps virus, Nipah virus, Hendra virus, Newcastle disease virus, Human respiratory syncytial virus, Rabies virus, Lassa virus, Hantavirus, Crimean-Congo hemorrhagic fever virus, Influenza, or Hepatitis D virus. In some preferred embodiments, the viral infection is caused by a coronavirus. Examples of a coronavirus includes but is not limited to Alphacoronavirus 1, Human coronavirus 229E, Human coronavirus NL63, Miniopterus bat coronavirus 1, Miniopterus bat coronavirus HKU8, Porcine epidemic diarrhea virus, Rhinolophus bat coronavirus HKU2, Scotophilus bat coronavirus 512, Betacoronavirus 1 (Bovine Coronavirus, Human coronavirus OC43), Hedgehog coronavirus 1, Human coronavirus HKU1, Middle East respiratory syndrome-related coronavirus, Murine coronavirus, Pipistrellus bat coronavirus HKU5, Rousettus bat coronavirus HKU9, Severe acute respiratory syndrome-related coronavirus (SARS-CoV, SARS-CoV-2), Tylonycteris bat coronavirus HKU4, Avian coronavirus, Beluga whale coronavirus SW1, Bulbul coronavirus HKU11 and Porcine coronavirus HKU15. In some preferred embodiments, the viral infection is caused by SARS-CoV2.

In other embodiments, the infection may be bacterial in nature. The bacterium causing the bacterial infection may include, but is not necessarily limited to, *Acinetobacter* species, *Actinobacillus* species, *Actinomycetes* species, an *Actinomyces* species, *Aerococcus* species an *Aeromonas* species, an *Anaplasma* species, an *Alcaligenes* species, a *Bacillus* species, a *Bacteroides* species, a *Bartonella* species, a *Bifidobacterium* species, a *Bordetella* species, a *Borrelia* species, a *Brucella* species, a *Burkholderia* species, a *Campylobacter* species, a *Capnocytophaga* species, a *Chlamydia* species, a *Citrobacter* species, a *Coxiella* species, a *Corynbacterium* species, a *Clostridium* species, an *Eikenella* species, an *Enterobacter* species, an *Escherichia* species, an *Enterococcus* species, an *Ehrlichia* species, an *Epidermophyton* species, an *Erysipelothrix* species, a *Eubacterium* species, a *Francisella* species, a *Fusobacterium* species, a *Gardnerella* species, a *Gemella* species, a *Haemophilus* species, a *Helicobacter* species, a *Kingella* species, a *Klebsiella* species, a *Lactobacillus* species, a *Lactococcus* species, a *Listeria* species, a *Leptospira* species, a *Legionella* species, a *Leptospira* species, *Leuconostoc* species, a *Mannheimia* species, a *Microsporum* species, a *Micrococcus* species, a *Moraxella* species, a *Morganell* species, a *Mobiluncus* species, a *Micrococcus* species, *Mycobacterium* species, a *Mycoplasm* species, a *Nocardia* species, a *Neisseria* species, a *Pasteurelaa* species, a *Pediococcus* species, a *Peptostreptococcus* species, a *Pityrosporum* species, a *Plesiomonas* species, a *Prevotella* species, a *Porphyromonas* species, a *Proteus* species, a *Providencia* species, a *Pseudomonas* species, a *Propionibacteriums* species, a *Rhodococcus* species, a *Rickettsia* species, a *Rhodococcus* species, a *Serratia* species, a *Stenotrophomonas* species, a *Salmonella* species, a *Serratia* species, a *Shigella* species, a *Staphylococcus* species, a *Streptococcus* species, a *Spirillum* species, a *Streptobacillus* species, a *Treponema* species, a *Tropheryma* species, a *Trichophyton* species, an *Ureaplasma* species, a *Veillonella* species, a *Vibrio* species, a *Yersinia* species, a *Xanthomonas* species, or combination thereof.

In other embodiments, the infection may be fungal, and may be caused by fungi such as, but not necessarily limited to, *Aspergillus, Blastomyces, Candidiasis, Coccidiodomycosis, Cryptococcus neoformans, Cryptococcus gatti,* sp. *His-*

14

*toplasma* sp. (such as *Histoplasma capsulatum*), *Pneumocystis* sp. (such as *Pneumocystis jirovecii*), *Stachybotrys* (such as *Stachybotrys chartarum*), *Mucroymcosis, Sporothrix,* fungal eye infections ringworm, *Exserohilum, Cladosporium, Geotrichum, Saccharomyces,* a *Hansenula* species, a *Candida* species, a *Kluyveromyces* species, a *Debaryomyces* species, a *Pichia* species, a *Penicillium* species, a *Cladosporium* species, a *Byssochlamys* species or a combination thereof.

In other embodiments, the infection may be caused by a protozoan, such as Euglenozoa, a Heterolobosea, a Diplomonadida, an Amoebozoa, a Blastocystic, an Apicomplexa, or a combination thereof.

In other embodiments, the infection may be caused by a parasite, such as, but not necessarily limited to, *Trypanosoma cruzi* (Chagas disease), *T. brucei gambiense, T. brucei rhodesiense, Leishmania braziliensis, L. infantum, L. mexicana, L. major, L. tropica, L. donovani, Naegleria fowleri, Giardia intestinalis (G. lamblia, G. duodenalis), canthamoeba castellanii, Balamuthia madrillaris, Entamoeba histolytica, Blastocystic hominis, Babesia microti, Cryptosporidium parvum, Cyclospora cayetanensis, Plasmodium falciparum, P. vivax, P. ovale, P. malariae,* and *Toxoplasma gondii,* or a combination thereof.

In some embodiments, the pharmaceutical composition and method comprising the administration of the pharmaceutical composition according to the invention is able to treat and/or prevent an associated inflammatory disorder that is related to cytokine and immune dysfunction, such as, but not limited to CRS, ARDS, ALI, AIDS, asthma, chronic peptic ulcer, tuberculosis, rheumatoid arthritis, periodontitis, ulcerative colitis, Crohn's disease, sinusitis, encephalitis, myelitis, meningitis, arachnoiditis, neuritis, dacryoadenitis, scleritis, episcleritis, keratitis, retinitis, chorioretinitis, blepharitis, conjunctivitis, uveitis, otitis externa, otitis media, Labyrinthitis, mastoiditis, carditis, endocarditis, myocarditis, pericarditis, vasculitis, arteritis, phlebitis, capillaritis, sinusitis, rhinitis, pharyngitis, laryngitis, tracheitis, bronchitis, bronchiolitis, pneumonitis, pleuritis, mediastinitis, stomatitis, gingivitis, gingivostomatitis, glossitis, tonsillitis, sialadenitis, parotitis, cheilitis, pulpitis, gnathitis, esophagitis, gastritis, gastroenteritis, enteritis, colitis, enterocolitis, duodenitis, ileitis, caecitis, appendicitis, proctitis, hepatitis, ascending cholangitis, cholecystitis, pancreatitis, peritonitis, dermatitis, folliculitis, cellulitis, hidradenitis, arthritis, dermatomyositis, myositis, synovitis, tenosynovitis, bursitis, enthesitis, fasciitis, capsulitis, epicondylitis, tendinitis, panniculitis, osteochondritis, osteitis, osteomyelitis, spondylitis, periostitis, chondritis, nephritis, glomerulonephritis, pyelonephritis, ureteritis, cystitis, urethritis, oophoritis, salpingitis, endometritis, parametritis, cervicitis, vaginitis, vulvitis, mastitis, orchitis, epididymitis, prostatitis, seminal vesiculitis, balanitis, posthitis, balanoposthitis, chorioamnionitis, funisitis, omphalitis, insulitis, hypophysitis, thyroiditis, parathyroiditis, adrenalitis, lymphangitis or lymphadenitis.

In some embodiments, the pharmaceutical composition and method comprising the administration of the pharmaceutical composition according to the invention is able to treat and/or prevent aging-related diseases, the pharmaceutical composition comprising therapeutic agent X or a pharmaceutically acceptable salt thereof and a therapeutic agent Y or a pharmaceutically acceptable salt thereof.

In some embodiments, the pharmaceutical composition and method comprising therapeutic agent X or a pharmaceutically acceptable salt thereof and a therapeutic agent Y or a pharmaceutically acceptable salt thereof may effectively prevent and/or treat aging associated diseases by promoting regeneration.

In some embodiments, the pharmaceutical composition and method comprising therapeutic agent X or a pharmaceutically acceptable salt thereof and a therapeutic agent Y or a pharmaceutically acceptable salt thereof may effectively prevent and or treat aging associated diseases by reversing fibrosis.

In some embodiments, the pharmaceutical composition and method comprising therapeutic agent X or a pharmaceutically acceptable salt thereof and a therapeutic agent Y or a pharmaceutically acceptable salt thereof may effectively prevent and or treat aging associated diseases by reversing senescence. The effect of therapeutic agent X and therapeutic agent Y is able to be evaluated by testing the therapeutic agents against relevant cell and tissue models, some of which are detailed in the examples listed. Alternatively, the effect of therapeutic agent X and therapeutic agent Y is able to be evaluated by testing the therapeutic agents against relevant animal models, some of which are described in the examples.

In some embodiments, the pharmaceutical composition and method comprising therapeutic agent X or a pharmaceutically acceptable salt thereof and a therapeutic agent Y or a pharmaceutically acceptable salt thereof may effectively prevent and or treat aging associated diseases by improving insulin sensitivity or preventing or treating insulin resistance. In some preferred embodiments, the pharmaceutical composition comprising therapeutic agent X or a pharmaceutically acceptable salt thereof and a therapeutic agent Y or a pharmaceutically acceptable salt thereof may by improving insulin sensitivity, thereby improve glucose tolerance.

In some embodiments, the pharmaceutical composition and method comprising therapeutic agent X or a pharmaceutically acceptable salt thereof and a therapeutic agent Y or a pharmaceutically acceptable salt thereof may effectively prevent and or treat aging and aging associated diseases by modulating inflammation. In some embodiments, the pharmaceutical composition comprising therapeutic agent X or a pharmaceutically acceptable salt thereof and a therapeutic agent Y or a pharmaceutically acceptable salt thereof may effectively prevent and or treat aging and aging associated diseases by preventing or treating or reducing chronic inflammation or inflammaging. In some preferred embodiments, the pharmaceutical composition and method comprising therapeutic agent X or a pharmaceutically acceptable salt thereof and a therapeutic agent Y or a pharmaceutically acceptable salt thereof may decrease the expression of factors such as but not limited to: AKT1, AKT2, AKT3, BTK, CASP8, CCL3, CCL4, CCL5, CD14, CD180, CD40, CD80, CD86, CHUK, CISH, CTNNAL1, CUEDC2, CXCL10, CXCL11, CXCL8, CXCL9, CYLD, FADD, FBXW5, FOS, GM-CSF, IFNA1, IFNA10, IFNA13, IFNA14, IFNA16, IFNA17, IFNA2, IFNA21, IFNA4, IFNA5, IFNA6, IFNA7, IFNA8, IFNAR1, IFNAR2, IFNB1, IFNG, IKBKB, IKBKE, IKBKG, IL12A, IL12B, IL18, IL1B, IL6, IL8, IRAK1, IRAK2, IRAK3, IRAK4, IRF3, IRF5, IRF7, JUN, LBP, LY96, MAP2K1, MAP2K2, MAP2K3, MAP2K4, MAP2K6, MAP2K7, MAP3K7, MAP3K8, MAPK1, MAPK10, MAPK11, MAPK12, MAPK13, MAPK14, MAPK3, MAPK8, MAPK9, MBL2, MIR105-1, MIR6502, MIR718, MIR98, MIRLET7E, MIRLET7I, MLST8, MYD88, NFKB1, NFKB2, NFKBIA, OTUD5, PELI1, PELI2, PELI3, PIK3CA, PIK3CB, PIK3CD, PIK3CG, PIK3R1, PIK3R2, PIK3R3, PIK3R5, PLK1, PROBE, PTPN6, RAC1, RBCK1, RELA, RIPK1, RNF216, RNF31, RNF41, SARM1, SFTPA2, SFTPD, SIGIRR, SMAD6, SOCS1, SPP1, SQSTM1, STAT1, SYK, TAB1, TAB2, TABS, TBK1, TICAM1, TICAM2, TIFA, TIRAP, TLR1, TLR2, TLR3, TLR4, TLR5, TLR6, TLR7, TLR8, TLR9, TMED7, TNFA, TNFAIP3, TOLLIP, TRAF3, TRAF6, TRAFD1, TREM1, USP7, ZMYND11.

In some embodiments, the pharmaceutical composition and method comprising therapeutic agent X or a pharmaceutically acceptable salt thereof and a therapeutic agent Y or a pharmaceutically acceptable salt thereof may effectively prevent and or treat aging associated diseases such as Alzheimer's Disease, Parkinson's Disease, dementia atherosclerosis, cardiovascular disease, type II Diabetes, cancer, arthritis, rheumatoid arthritis, periodontitis, cataracts, osteoporosis, fibrosis, cirrhosis, idiopathic pulmonary fibrosis, cardiac fibrosis, uterine fibrosis, scarring, arthrofibrosis, chronic kidney disease, Crohn's disease, keloids, myelofibrosis, retroperitoneal fibrosis, scleroderma, sclerosis, chronic wounds (such as diabetic foot ulcer), chronic dermal fibrosis, cutaneous fibrosis, skin aging, nonalcoholic steatohepatitis (NASH), hair loss, tissue atrophy, menopause, primary ovarian insufficiency, endometrial hyperplasia, adenomyosis and sarcopenia.

In some preferred embodiments, the pharmaceutical composition and method comprising therapeutic agent X or a pharmaceutically acceptable salt thereof and a therapeutic agent Y or a pharmaceutically acceptable salt thereof may effectively prevent and or treat fibrosis. It is widely accepted in the state of the art that fibrosis, inflammation-induced fibrosis, inflammation and inflammaging can be modeled in animals for example by administering bleomycin or lipopolysaccharide to animal models (e.g., mice or rats).

In some preferred embodiments, the pharmaceutical composition and method comprising therapeutic agent X or a pharmaceutically acceptable salt thereof and a therapeutic agent Y or a pharmaceutically acceptable salt thereof may effectively prevent and or treat pulmonary fibrosis. Non-limiting examples of pulmonary fibrosis include but are not limited to Chronic obstructive pulmonary disease (COPD), Idiopathic pulmonary fibrosis (IPF), Interstitial Lung Disease (ILD).

In some preferred embodiments, the pharmaceutical composition and method comprising therapeutic agent X or a pharmaceutically acceptable salt thereof and a therapeutic agent Y or a pharmaceutically acceptable salt thereof may effectively prevent and or treat hair loss or alopecia. Non-limiting examples of hair loss include but are not limited to alopecia areata, alopecia totalis and alopecia universalis and androgenic alopecia.

In some preferred embodiments, the pharmaceutical composition and method comprising therapeutic agent X or a pharmaceutically acceptable salt thereof and a therapeutic agent Y or a pharmaceutically acceptable salt thereof may effectively prevent and or treat cirrhosis.

In some preferred embodiments, the pharmaceutical composition and method comprising therapeutic agent X or a pharmaceutically acceptable salt thereof and a therapeutic agent Y or a pharmaceutically acceptable salt thereof may effectively prevent and or treat NASH.

In some preferred embodiments, the pharmaceutical composition and method comprising therapeutic agent X or a pharmaceutically acceptable salt thereof and a therapeutic agent Y or a pharmaceutically acceptable salt thereof may effectively prevent and or treat type II diabetes.

In some preferred embodiments, the pharmaceutical composition and method comprising therapeutic agent X or a pharmaceutically acceptable salt thereof and a therapeutic agent Y or a pharmaceutically acceptable salt thereof may effectively prevent and or treat chronic wounds.

In some preferred embodiments, the pharmaceutical composition and method comprising therapeutic agent X or a pharmaceutically acceptable salt thereof and a therapeutic agent Y or a pharmaceutically acceptable salt thereof may effectively prevent and or treat aging-associated diseases specific to women such as but not limited to menopause, primary ovarian insufficiency, endometrial hyperplasia, adenomyosis, polycystic ovary syndrome.

In some preferred embodiments, the pharmaceutical composition and method comprising therapeutic agent X or a pharmaceutically acceptable salt thereof and a therapeutic agent Y or a pharmaceutically acceptable salt thereof may effectively prevent and/or treat sarcopenia.

In some preferred embodiments, the pharmaceutical composition and method comprising therapeutic agent X or a pharmaceutically acceptable salt thereof and a therapeutic agent Y or a pharmaceutically acceptable salt thereof may effectively prevent and or treat sarcopenia. Sarcopenia is a condition characterized by loss of skeletal muscle mass and function and occurs in high prevalence among the aged, especially aged men. Increase in muscle mass may therefore be seen as a way to ameliorate or treat such a condition.

In some embodiments, the present invention may comprise a pharmaceutical composition having a therapeutic agent X or a pharmaceutically acceptable salt thereof; a therapeutic agent Y or a pharmaceutically acceptable salt thereof; and at least one pharmaceutically acceptable excipient, in which the therapeutic agent X is a non-steroidal anti-inflammatory drug and the therapeutic agent Y is a fatty acid oxidation inhibitor. In further embodiments, the present invention may comprise a method of treating a condition in a subject in need thereof, the method comprising administering to the subject an effective amount of a pharmaceutical composition having a therapeutic agent X or a pharmaceutically acceptable salt thereof; a therapeutic agent Y or a pharmaceutically acceptable salt thereof; and at least one pharmaceutically acceptable excipient, in which the therapeutic agent X is a non-steroidal anti-inflammatory drug and the therapeutic agent Y is a fatty acid oxidation inhibitor.

In some embodiments, in the pharmaceutical composition, the therapeutic agent X or a pharmaceutically acceptable salt thereof and the therapeutic agent Y or a pharmaceutically acceptable salt thereof are included in a single dosage form.

In further embodiments, in the pharmaceutical composition, the therapeutic agent X or a pharmaceutically acceptable salt thereof and the therapeutic agent Y or a pharmaceutically acceptable salt exist in separate dosage forms.

In some embodiments, the therapeutic agent X is selected from at least one of the COX inhibitors, salicylates, ibuprofen, phenoxyibuprofen, naproxen, diclofenac, celecoxib, mefenamic acid, etoricoxib, indomethacin, ketorolac, tetrachlorofenoic acid, sulindac and tometine. In some embodiments, therapeutic agent X is a salicylate or derivative thereof. In some embodiments, therapeutic agent X is 2-acetyloxybenzoic acid. In some embodiments, the therapeutic agent Y is selected from at least one of the CPT inhibitors, carnitine biosynthesis inhibitors, 3-ketoacyl-co-enzyme A thiolase inhibitors, etomoxir, oxfenicine, perhexiline, mildronate, 1-(2,3,4-Trimethoxybenzyl) piperazine dihydrochloride, trimetazidine, ethoxylcarnitine, aminocarnitine or a phosphonyloxy derivative of carnitine. In some preferred embodiments, therapeutic agent Y is 1-(2,3,4-Trimethoxybenzyl) piperazine dihydrochloride.

In some embodiments, the mass ratio of the therapeutic agent X and the therapeutic agent Y is between 1:1 to 10:1, including 1:1, 2:1, 3:1, 4:1, 5:1, 6:1, 7:1, 8:1, 9:1, or 10:1. In some preferred embodiments, the mass ratio of the therapeutic agents is 5:1 or 6:1 or 7:1.

In some embodiments, the amount of therapeutic agent X can range anywhere from 1 mg/kg to 100 mg/kg or more per day and the amount of therapeutic agent Y can range anywhere from 0.25 mg/kg to 100 mg/kg or more per day. The exact amount to be used varies according the exact disease indication and the physiology of the individual. In some embodiments, therapeutic agent X and therapeutic agent Y can be administered once in n days, where n ranges from 1 to 14. In some embodiments, therapeutic agent X and therapeutic agent Y can be administered once a day or multiple times a day. In some embodiments, therapeutic agent X and therapeutic agent Y can be administered every day, every two days, every three days, every four days, every five days, every six days, weekly, etc.

In some embodiments, the therapeutic agent X and the therapeutic agent Y are administered simultaneously. In some embodiments, the therapeutic agent X and the therapeutic agent Y are included in a single dosage form. In some embodiments, the possible routes of administration of therapeutic agent X and therapeutic agent Y in a single dosage form include but is not limited to: oral, sublingual, buccal, nasal, inhalation, intratracheal, intravenous, intraarterial, intracoronary, intrathecal, intramuscular, intraperitoneal, intramyocardial, trans-endocardial, trans-epicardial, subcutaneous, transdermal, vaginal, rectal, or otic. In some preferred embodiments, therapeutic agent X and therapeutic agent Y in a single dose form are administered orally or intravenously or subcutaneously.

In some embodiments, the therapeutic agent X and the therapeutic agent Y are administered respectively. In some embodiments, the therapeutic agent X is administered prior to the therapeutic agent Y. In some embodiments, the therapeutic agent X is administered after the therapeutic agent Y. In some embodiments, the possible routes of administration of therapeutic agent X and therapeutic agent Y in separate dosage forms include but is not limited to: oral, sublingual, buccal, nasal, inhalation, intratracheal, intravenous, intraarterial, intracoronary, intrathecal, intramuscular, intraperitoneal, intramyocardial, trans-endocardial, trans-epicardial, subcutaneous, transdermal, vaginal, rectal, or otic. In some embodiments, therapeutic agent X and therapeutic agent Y in separate dosage forms are administered orally or intravenously.

In some embodiments, therapeutic agent X and therapeutic agent Y are administered orally, respectively. In some embodiments, therapeutic agent X and therapeutic agent Y are administered by injection, respectively.

Pharmaceutical compositions for parenteral injection include aqueous or non-aqueous solutions, dispersions, suspensions, or emulsions, pharmaceutically acceptable sterile or non-sterile, and powders for reconstitution in sterile injectable solutions or dispersions.

In some embodiments, and for a more effective distribution, the compounds of the invention may be embedded in extended controlled release or directed administration systems, such as polymeric matrices, liposomes and microspheres.

In preferred embodiments, the pharmaceutical composition of the present invention may be a solid composition for oral administration, and specific examples thereof include tablets, granules, fine granules, capsules, powders, and pills. The solid oral composition of the present invention may have an excipient, a binder, a lubricant and the like added thereto, in addition to the pharmaceutically acceptable salt of therapeutic agent X or therapeutic agent Y or combinations thereof, and may be formulated into the respective forms. Examples of excipients that may be used include lactose, corn starch, crystalline cellulose, sucrose, glucose, mannitol, sorbitol, and calcium carbonate. Examples of the binder include hydroxypropyl cellulose, hydroxyethyl cellulose, hypromellose, hydroxyethylethyl cellulose, hydroxyethylm-ethyl cellulose, polyvinylpyrrolidone, and polyvinyl alco-hol. Examples of the lubricant include magnesium stearate, stearic acid, palmitic acid, calcium stearate, and talc. Such formulations are described in detail in a number of sources which are well known and readily available to those skilled in the art. For example, Remington's The Science and Practice of Pharmacy, edited by Allen, Loyd V., Jr, 22nd edition, describe the making of formulations which may be used in connection with the subject invention.

The examples below are intended to be purely exemplary of the present application and should therefore not be considered to limit the invention in any way. The following examples and detailed descriptions are offered by way of illustration and not by way of limitation.

Example 1: LPS-Induced Inflammation

Lipopolysaccharide (LPS) is a common antigen expressed by many pathogenic microbes, with severe effects on the host response that are not treatable with non-steroidal anti-inflammatory drugs alone. In particular, intraperitoneal treatment with LPS is a reliable model of pathogen-induced CRS, that also recapitulates many features of human ARDS, including enhanced production of pro-inflammatory factors, high levels of immune infiltration, and loss of endothelial and vascular integrity in the lung.

Adult 6-8 week-old DIO mice were fed with high fat diet (Jackson Labs) for 12 weeks before any experiments were initiated. DIO mice received 5 mg/kg of LPS (Sigma) injected intraperitoneally. Mice on a normal chow diet served as controls. Mice injected with PBS vehicle served as controls for drug treatment. Mice were killed at 6 hours after stimulation with LPS (FIG. 1A). Lungs were frozen in liquid nitrogen for molecular assays, or fixed in formalin for histologic examination. Histology results showed severe pulmonary congestion, alveolar thickening, hyaline mem-brane formations, and inflammatory infiltration in lung tissues from all LPS-treated mice, but these changes were more pronounced in DIO mice. Lungs from DIO mice exhibited more severe signs of ALI compared with normal mice, as shown by the increased lung protein content, cell number in bronchoalveolar lavage fluid (BALF), and lactic acid dehydrogenase (LDH) content in BALF. These results show that diet-induced obese (DIO) mice are more suscep-tible to LPS-induced lung injury (FIG. 1B).

To test effects on mortality and survival, LPS was injected intraperitoneally at a dose of 30 mg/kg. The mortality of mice was recorded every 12 hours for 3 days after the LPS injection (n=12). LPS-treated DIO mice started to die by 16 hours, and ~80% of the mice were dead by 40 hours. In contrast, normal mice treated with LPS lived longer, and only ~40% died by 40 hours. These results showed that diet-induced obese (DIO) mice are more susceptible to death from LPS-induced inflammation (FIG. 1B).

Further assessments of the infiltration of inflammatory cells into lungs showed that lung myeloperoxidase (MPO) activity and the number of neutrophils in BALF were higher in DIO mice compared to normal mice. The levels of TNF-a in BALF and lung tissue were also much higher in DIO mice than normal mice treated with LPS. These results show that obesity exacerbates LPS-induced lung inflammation (FIG. 1C).

To test whether prophylactic treatment with the drugs X and Y may block ALI pathogenesis, we performed a rescue experiment using intraperitoneal injections of X and Y. In this experiment, and in examples listed henceforth, X is 2-acetoxybenzoic acid (CAS no: 50-78-2) and Y is 1-[(2,3, 4-trimethoxyphenyl)methyl]piperazine, (CAS no: 5011-34-7). Histologic analysis showed that the lung structure of DIO mice prophylactically treated with the drug combination XY 2 weeks before LPS injection, was significantly improved in comparison to DIO mice treated with X alone, Y alone, or PBS vehicle, 2 weeks before LPS injection. These results show that the drug combination XY ameliorates ALI in DIO mice (FIG. 1B).

Survival analysis further showed that the survival rate of DIO mice prophylactically treated with the drug combina-tion XY 2 weeks before LPS injection, was significantly improved in comparison to DIO mice treated with X alone, Y alone, or PBS vehicle, 2 weeks before LPS injection. These results show that the drug combination XY prevents ALI-induced death in DIO mice (FIG. 1B).

Moreover, the edema formation protein, cell number, LDH content and neutrophil counts in BALF, and MPO activity of DIO mice prophylactically treated with the drug combination XY 2 weeks before LPS injection, were all significantly attenuated in comparison to DIO mice treated with X alone, Y alone, or PBS vehicle, 2 weeks before LPS injection. These results show that the drug combination XY ameliorates LPS-induced lung inflammation (FIG. 1C).

Example 2: Virus Coreceptors

Figure 3:
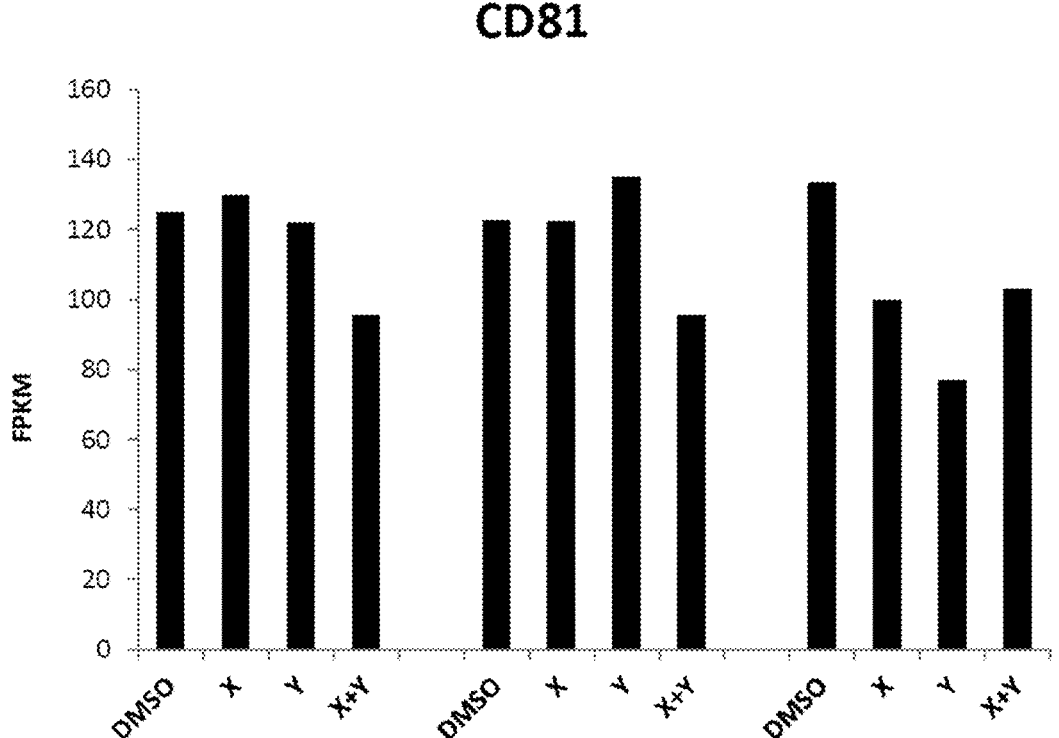
FIG. 3-FIG. 3 shows that the drug combination X and Y decreases expression of the hepatitis C virus coreceptor CD81.
Figure 4:
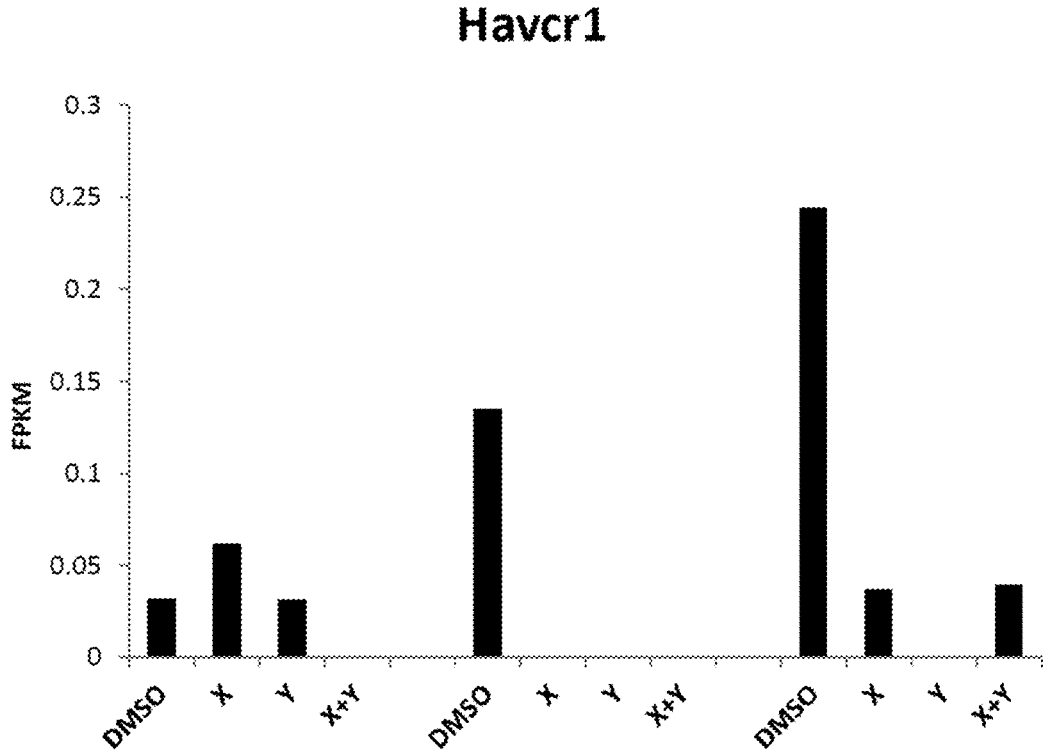
FIG. 4-FIG. 4 shows that the drug combination X and Y decreases expression of the hepatitis A virus coreceptor HAVCR1.
Figure 5:
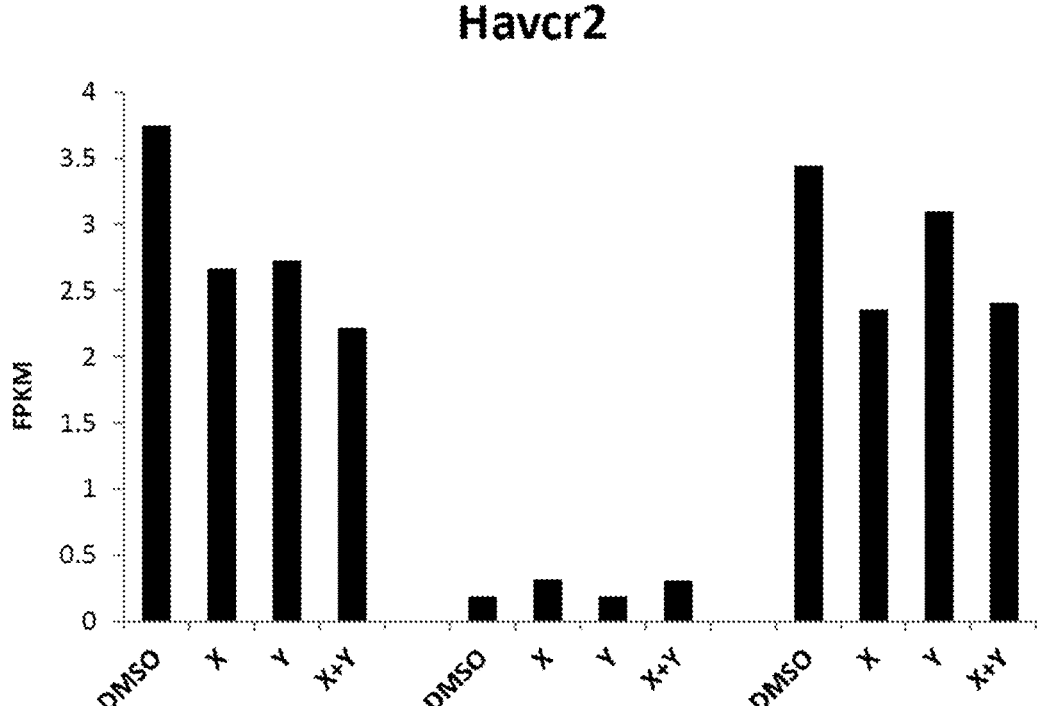
FIG. 5-FIG. 5 shows that the drug combination X and Y decreases expression of the hepatitis A virus coreceptor HAVCR2
Figure 6:
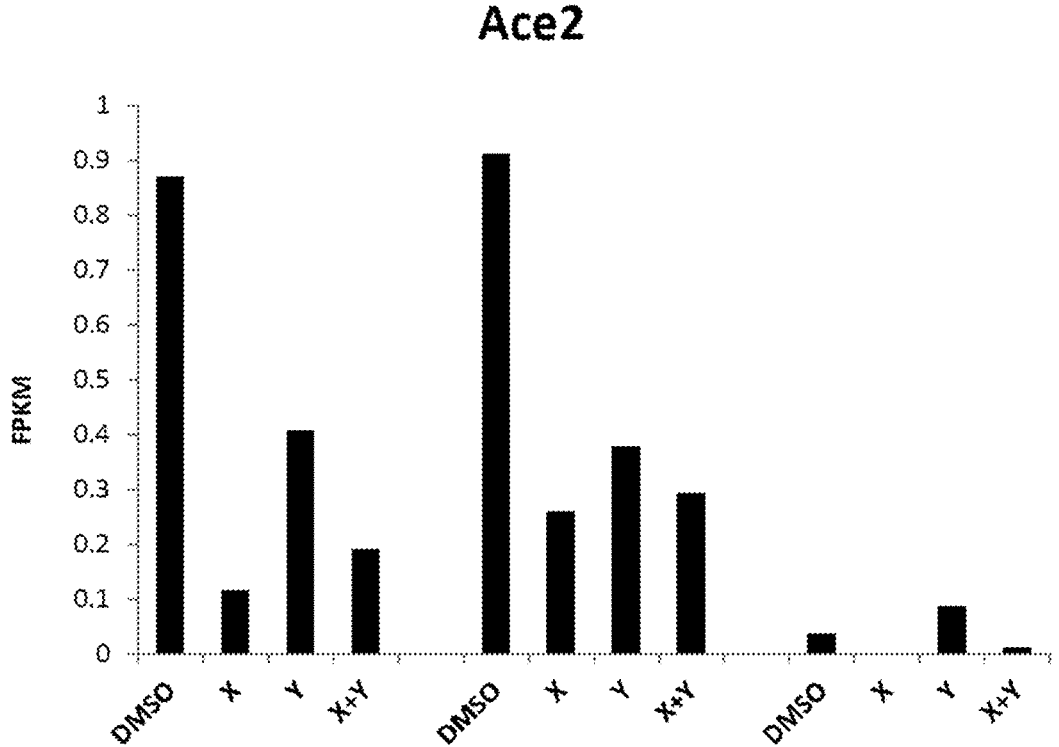
FIG. 6-FIG. 6 shows that the drug combination X and Y decreases expression of the coronavirus coreceptor ACE2.
Figure 7:
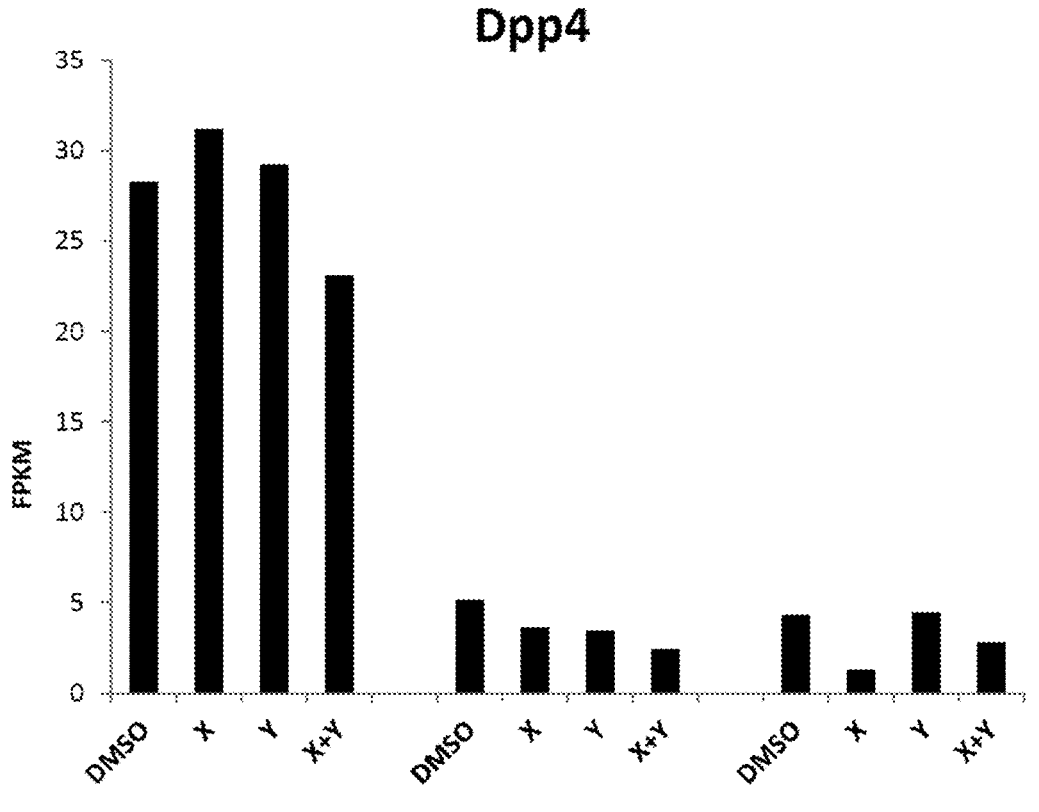
FIG. 7-FIG. 7 shows that the drug combination X and Y decreases expression of the coronavirus coreceptor DPP4
Figure 8:
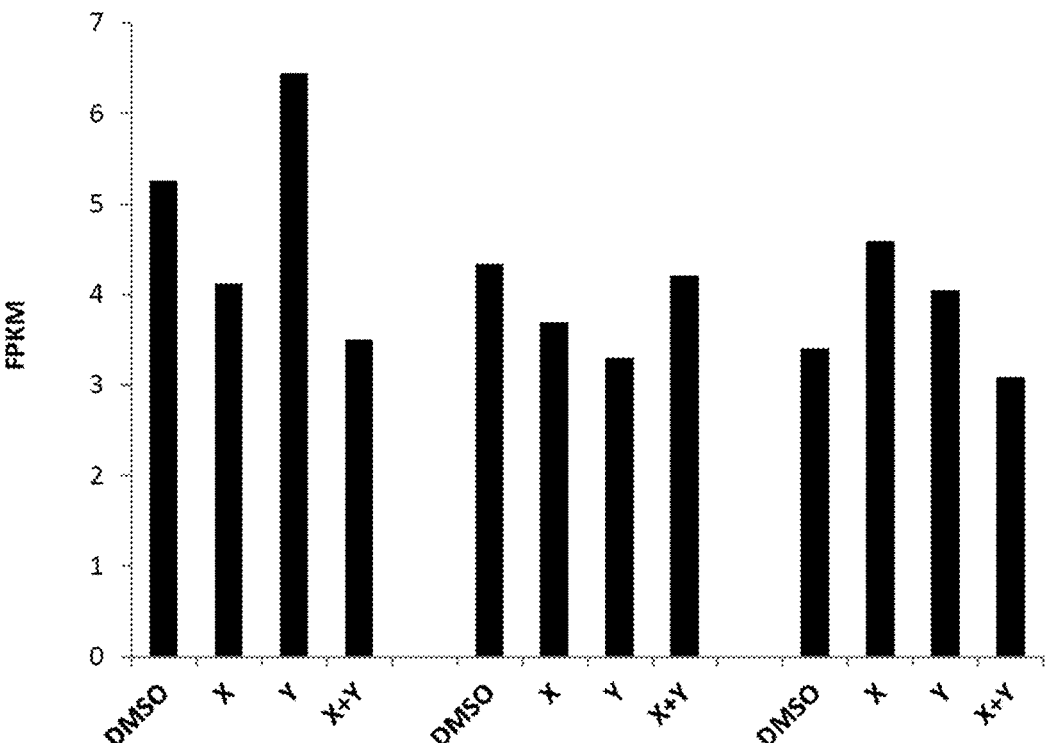
FIG. 8-FIG. 8 shows that the drug combination X and Y decreases expression of the virus coreceptor integrin alpha (v).
Figure 9:
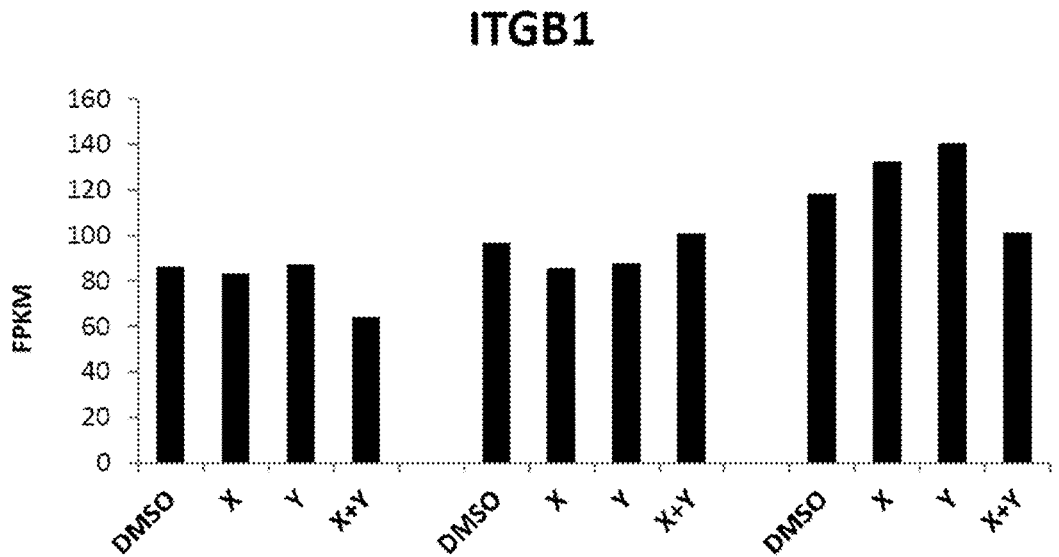
FIG. 9-FIG. 9 shows that the drug combination X and Y decreases expression of the virus coreceptor integrin beta1.
Figure 10:
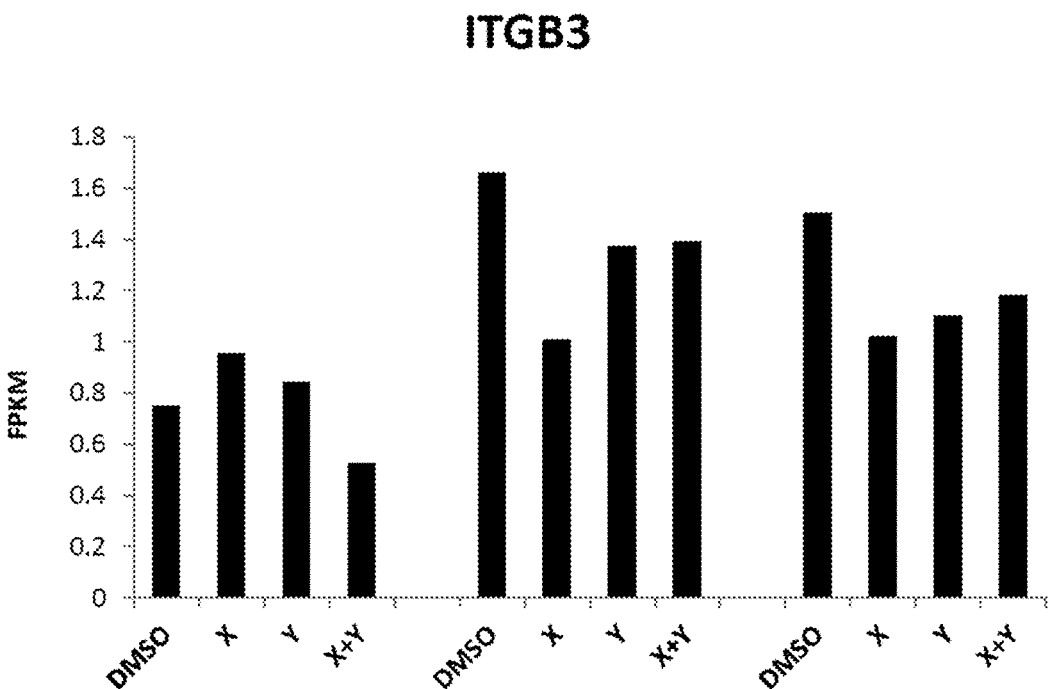
FIG. 10-FIG. 10 shows that the drug combination X and Y decreases expression of the virus coreceptor integrin beta3.
Figure 11:
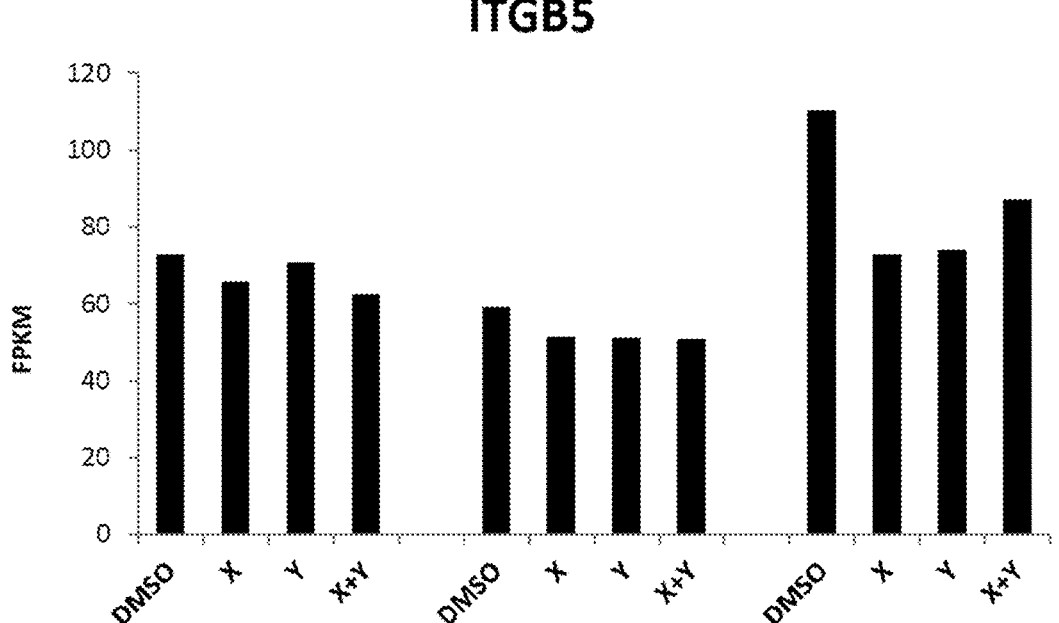
FIG. 11-FIG. 11 shows that the drug combination X and Y decreases expression of the virus coreceptor integrin beta5.
Figure 12:
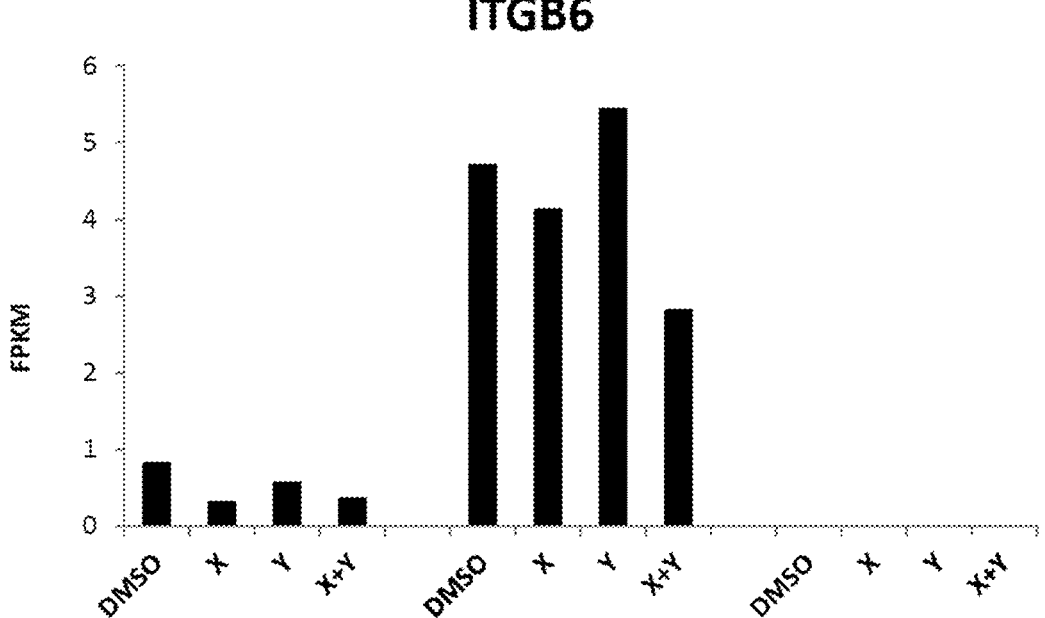
FIG. 12-FIG. 12 shows that the drug combination X and Y decreases expression of the virus coreceptor integrin beta6.

To test if the drug treatment might be effective in reducing viral coreceptor expression, with potential efficacy in reduc-ing virus infection, we performed RNAseq profiling of various organs after 3 days of XY treatment. Briefly, total RNA was purified by ethanol precipitation and sent for RNAseq. Paired-end libraries were constructed and sequenced using a Nova-PE150 platform (Illumina). FIGS. 2 and 3 show that the drug combination XY decreases expression of the hepatitis C virus coreceptors CD36 and CD81. FIGS. 4 and 5 show that the drug combination XY decreases expression of the hepatitis A virus coreceptors HAVCR1 and HAVCR2. FIG. 6 shows that the drug com-bination XY decreases expression of the coreceptor for SARS-CoV and SARS-CoV-2, ACE2, as well as the core-ceptor for MERS coronavirus DPP4. FIGS. 7-12 show that the drug combination XY decreases expression of integrin alpha(v), integrin beta1, integrin beta3, integrin beta5, inte-grin beta6, which are coreceptors for adenoviruses, parvo-viruses and cytomegaloviruses. These results show that the drug combination XY may mitigate the spread of viral infectious disease.

Example 3: Senescent Cells in Aged Mammalian Tissues

Figure 13A:
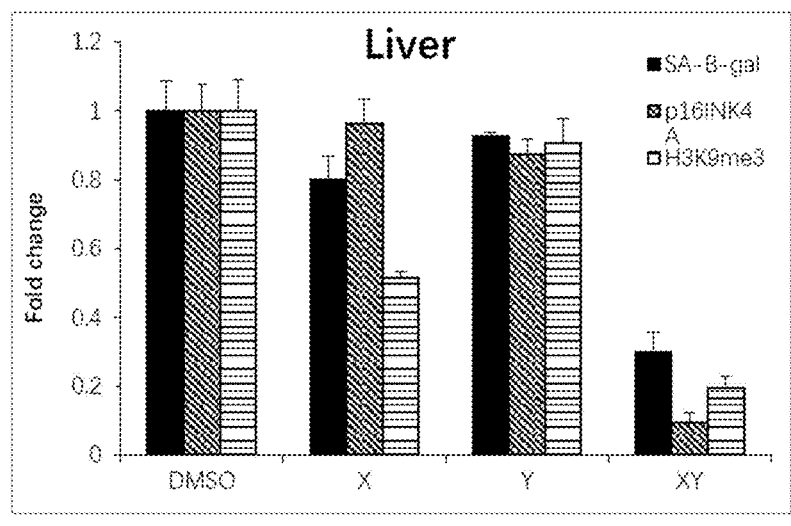
FIG. 13A-FIG. 13A shows that the drug combination X and Y suppresses senescence biomarkers and reduces senescent cells in aged liver tissues.
Figure 13B:
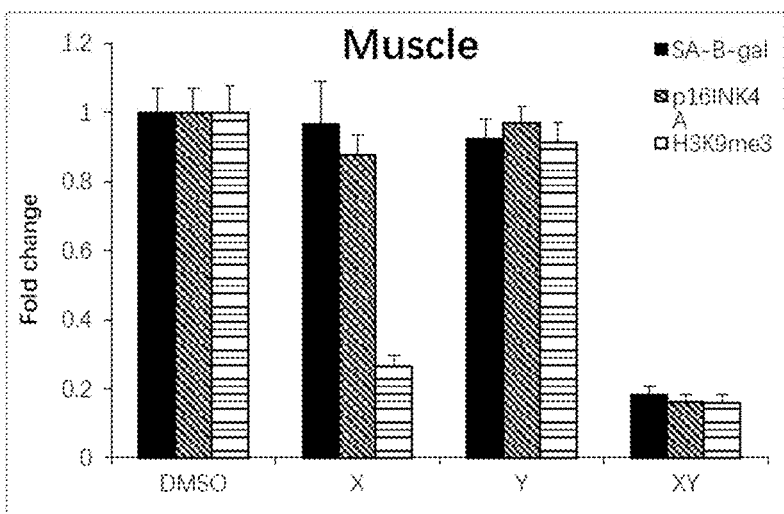
FIG. 13B-FIG. 13B shows that the drug combination X and Y suppresses senescence biomarkers and reduces senescent cells in aged muscle tissues.
Figure 13C:
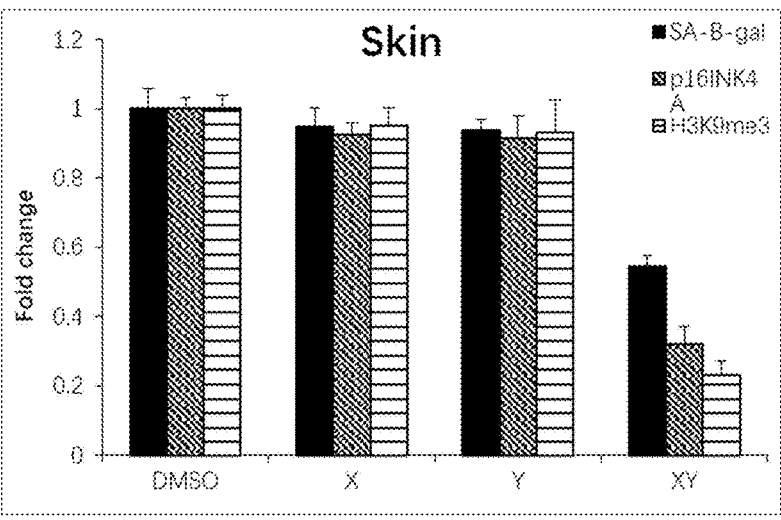
FIG. 13C-FIG. 13C shows that the drug combination X and Y suppresses senescence biomarkers and reduces senescent cells in aged skin tissues.

Mammalian cells that exhibit senescence are marked by positive staining for senescence-associated-β-galactosidase (SA-β-gal), and protein expression of p16INK4A and senes-cence-associated heterochromatin markers such as H3K9me3. To test if the drugs X and Y may reduce senescence in the tissues of aged mice, we intraperitoneally injected 2-year-old aged mice (n=10/group) with 20 mg/kg of X, or 4 mg/kg of Y, or both 20 mg/kg of X and 4 mg/kg of Y, relative to the DMSO vehicle control, on a daily basis for 30 days. Staining of liver, muscle and skin tissue sections for SA-β-gal activity was performed using the Senescence β-Galactosidase Staining Kit (Cell Signaling Technology) according to manufacturer's protocols. Protein expression of p16INK4A and H3K9me3 were evaluated by densitometric quantification of Western blots of the liver, muscle and skin tissue samples. The results revealed that only the drug combination X and Y significantly decreased all three bio-markers of senescence in aged liver, muscle and skin tissues (P<0.01), but not X alone or Y alone, relative to the DMSO vehicle control (FIGS. 13A-13C). This suggests that the drug combination X and Y is able to decrease senescent cells and/or reverse senescence.

Example 4: Cutaneous Wound Healing and Tissue Repair During Aging

Mammals manifest reduced rates of tissue repair with aging. One animal model for this phenomenon is the delayed cutaneous wound healing in aged db/db mice, compared to young mice. Chronic wounds were generated in db/db mice by performing full thickness 6 mm diameter excision wounds on the dorsal skin of 9-month-old mice. We used a well-described murine full-thickness excisional wound model (Loh et al., 2009). Briefly, a 6 mm disposable biopsy punch (Delasco) was used to make two circular full thickness wounds on the dorsal back skin of mice. Silicon wound splints (Grace BioLabs) were sutured with 4-0 Nylon to prevent skin contracture. Wounds were dressed with a sterile occlusive dressing and monitored daily. Borders were monitored by frequently application of permanent marker. Photos were taken at various time points throughout the duration of the experiment. The wounds remained open 20 days after wounding, and sometimes for over 3 months, as expected of chronic wounds. To test if the drugs X and Y can treat the chronic wounds of aged mice, we intraperitoneally injected aged mice (n=10/group) 20 days after wounding, with 20 mg/kg of X, or 4 mg/kg of Y, or both 20 mg/kg of X and 4 mg/kg of Y, relative to the DMSO vehicle control, on a daily basis for 30 days.

Figure 14:
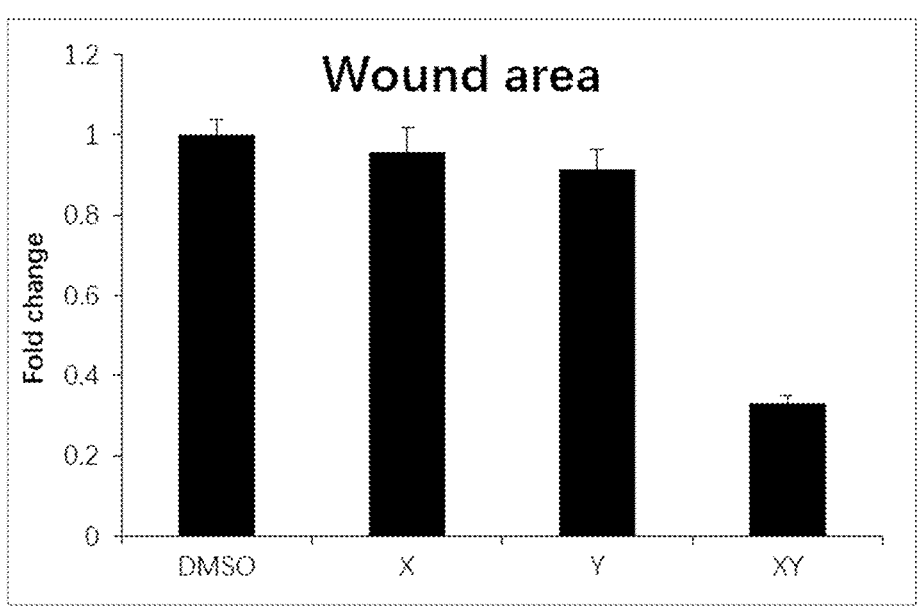
FIG. 14-FIG. 14 shows that the drug combination X and Y accelerates tissue repair in aged mice with chronic wounds.

Quantification of the dorsal wound areas revealed that only the drug combination X and Y significantly accelerated tissue repair in aged mice with chronic wounds (P<0.01), but not X alone or Y alone, relative to the DMSO vehicle control (FIG. 14).

Example 5: Hair Loss and Hair Regrowth During Aging

Figure 15:
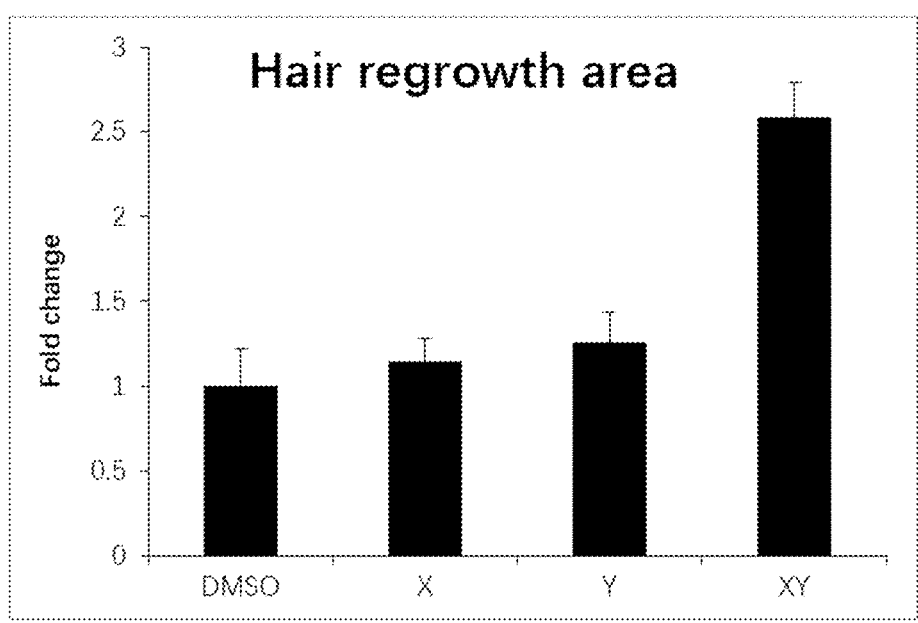
FIG. 15-FIG. 15 shows that the drug combination X and Y accelerates hair growth in aged mice with alopecia.

Humans manifest hair loss or alopecia with aging, most obviously in men exhibiting androgenetic alopecia or senile alopecia. Inflammation and aging, or inflammaging, are risk factors for alopecia. An animal model for this phenomenon is the delayed hair regeneration in ob/ob mice with inflammaging, after depilation. After dorsal hair removal from 8-week-old mice using depilatory cream (day 0), 3 wild-type mice and 3 inflammaging mice were regularly monitored until the depilated area was mostly covered with hair. Regenerated hair could be seen as dark hair on pinkish-white shaved skin. The hair regeneration area was quantified using the NIH ImageJ software program (NTIS, Springfield, VA). When the hair cycle reaches the second telogen phase by 8 weeks age in wild-type mice, depilation induces a rapid transition to anagen by the 1st week after depilation and complete hair regeneration by the 4th week after depilation in wild-type mice. In contrast, the first signs of anagen was only observed at the 6th week after depilation in inflammaging mice. To test if the drugs X and Y can ameliorate the hair regeneration defect in inflammaging mice, we intraperitoneally injected inflammaging mice after depilation (n=10/group), with 20 mg/kg of X, or 4 mg/kg of Y, or both 20 mg/kg of X and 4 mg/kg of Y, relative to the DMSO vehicle control, on a daily basis for 30 days. Quantification of the dorsal skin area with hair regeneration revealed that only the drug combination X and Y significantly accelerated hair regrowth in inflammaging mice after depilation (P<0.01), but not X alone or Y alone, relative to the DMSO vehicle control (FIG. 15).

Example 6: Tissue Fibrosis and Tissue Degeneration During Aging

Figure 16:
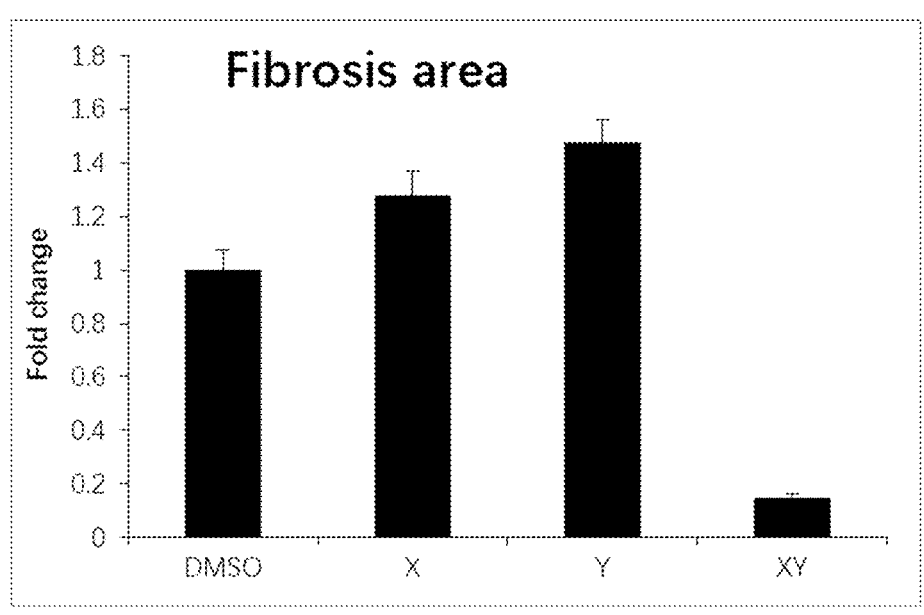
FIG. 16-FIG. 16 shows that the drug combination X and Y ameliorates tissue fibrosis in aged mice.

Aging mammals also display a reduced ability to resolve fibrosis, leading to tissue scarring and irreparable organ damage, e.g., in idiopathic pulmonary fibrosis (IPF), liver fibrosis and cardiac fibrosis. An animal model for IPF is bleomycin-induced lung injury in mice. Young and aged mice were anesthesized with intraperitoneal injection of ketamine (100 mg/kg) and xylazine (10 mg/kg), then administered with intra-tracheal bleomycin (1.25 U/kg) to induce lung injury, or saline (50 μL total volume). Fibrosis was quantified by measuring the fibrotic areas in lung tissue sections with Masson trichrome staining. An animal model for both liver fibrosis and cardiac fibrosis is the inflammaging mouse model, i.e., ob/ob mice fed on a high fat, high sugar, high cholesterol diet for 90 days (Research Labs). To test if the drugs X and Y can ameliorate the lung fibrosis in bleomycin-injured mice, and the liver and cardiac fibrosis in inflammaging mice, we intraperitoneally injected bleomy-cin-treated mice (n=10/group) and inflammaging mice (n=10/group) with 20 mg/kg of X, or 4 mg/kg of Y, or both 20 mg/kg of X and 4 mg/kg of Y, relative to the DMSO vehicle control, on a daily basis for 30 days. Quantification of the fibrosis by Masson trichrome staining revealed that only the drug combination X and Y significantly reversed fibrosis in inflammaging mice (P<0.01), but not X alone or Y alone, relative to the DMSO vehicle control (FIG. 16).

Example 7: Inflammation and Death

Figure 17:
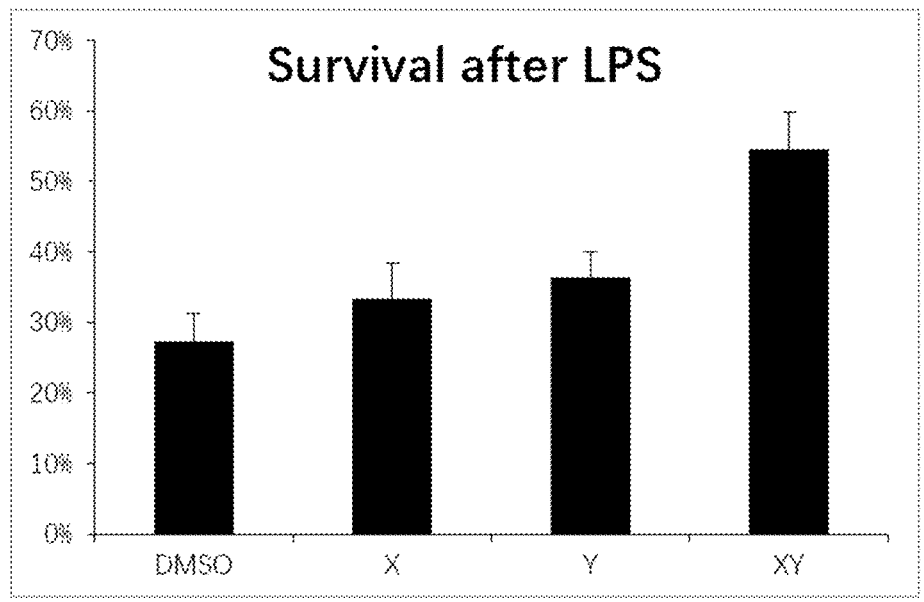
FIG. 17-FIG. 17 shows that the drug combination X and Y ameliorates inflammaging and inflammation-induced death in mice.

Aging and especially inflammaging are also associated with increased risk of death from septic shock or pro-inflammatory cytokine release syndrome. This is partly due to inflammaging-induced immunosenescence, which leads to dysfunctional immune responses that cause multi-organ failure and death. An animal model for this phenomenon is LPS endotoxin-induced septic shock in aged mice. For lethality studies, LPS (Sigma Aldrich) was injected intraperitoneally at a dose of 30 mg/kg. The mortality of mice was recorded every 12 hours for 3 days after the LPS challenge in each group. To test if the drugs X and Y can prophylactically ameliorate the lethal effects of LPS-induced sepsis, we intraperitoneally injected 2-year-old aged mice (n=10/group) with 20 mg/kg of X, or 4 mg/kg of Y, or both 20 mg/kg of X and 4 mg/kg of Y, relative to the DMSO vehicle control, on a daily basis for 30 days, before subjecting them to the LPS challenge. Quantification of the survival rate over time revealed that only the drug combination X and Y significantly improved survival after the LPS challenge (P<0.01), but not X alone or Y alone, relative to the DMSO vehicle control (FIG. 17).

Example 8: Immunosenescence-Associated Gene Signatures

Aging and especially chronic inflammaging leads to immunosenescence, i.e., the decrease in naïve T cells and dysfunctional skewing of immune cell subsets with aging. This causes an aberrant spike in the Th17- and Th1-driven pro-inflammatory responses when immunologically challenged, at the expense of the Treg- and Th2-driven anti-inflammatory response, which could lead to a lethal cytokine release syndrome and/or sepsis. To test how the drug combination X and Y affects the immune response, we isolated peripheral blood mononuclear cells (PBMCs) from mice treated with 20 mg/kg of X and 4 mg/kg of Y, relative to the DMSO vehicle control, on a daily basis for 30 days, and extracted their RNA with Trizol (Invitrogen) for RNAseq (Illumina). After Gene Set Enrichment Analysis (GSEA; Broad Institute), our results showed that the drug combination X and Y suppressed the Th1 pro-inflammatory signature, the Th1-associated/pro-Th17 cytokine IL2 signature, the Th1/Th17-associated cytokine IFNG signature, and the pan-activated Th-associated cytokines IL3/IL5/GM-CSF signature (FIGS. 18A and 18B). In contrast, X and Y promoted the Th2/Treg-associated anti-inflammatory cytokine signatures of IL4, IL10 and IL13 (FIG. 18C).

Example 9: Mimicry of Exercise to Suppress Inflammaging

Figures 19A, 19B, 19C, 19D:
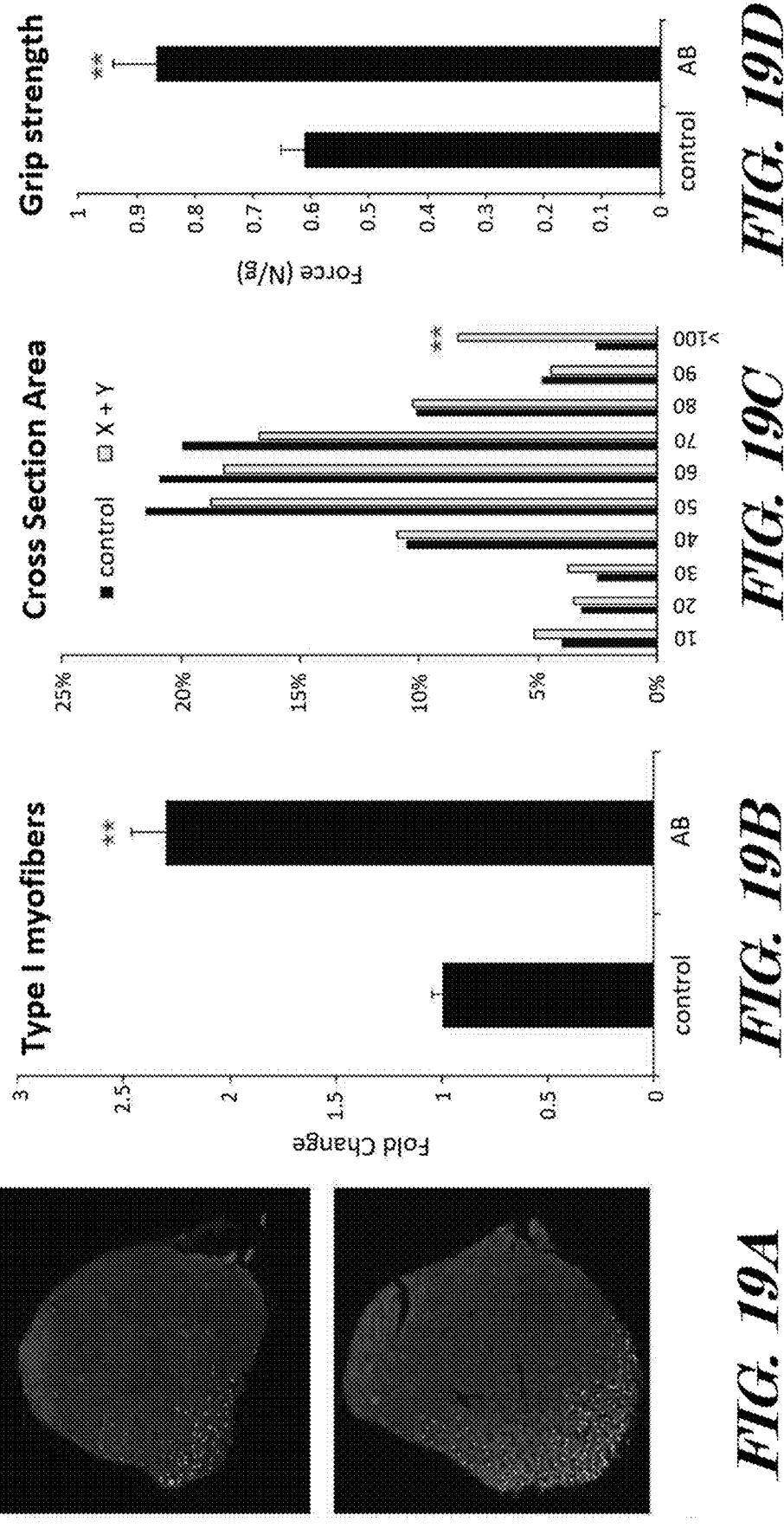
FIG. 19A-FIG. 19A shows that drug combination X and Y promotes oxidative muscle growth.
FIG. 19B-FIG. 19B shows that drug combination X and Y promotes oxidative muscle growth.
FIG. 19C-FIG. 19C shows that drug combination X and Y promotes oxidative muscle growth.
FIG. 19D-FIG. 19D shows that drug combination X and Y promotes oxidative muscle growth.

Physical muscular exercise is known to ameliorate the effects of aging, including chronic inflammaging and immunosenescence. To test how the drug combination X and Y affects the effects of physical exercise, cryosections of quadriceps muscles in inflammaging mice were immunostained for type I slow-twitch myofibers (FIG. 19A), and examined with fluorescence microscopy (Carl Zeiss). The results showed that the drug combination X and Y more than doubled the area of type I myofibers (P<0.01), indicating that the drug combination X and Y mimicked and enhanced the effects of endurance exercise (FIG. 19B). Moreover, quantification of the cross-sectional areas of the myofibers indicated that the drug combination X and Y increased the proportion of myofibers with areas above the threshold of 100 pixels (P<0.01), suggesting that the drug combination X and Y induced muscle hypertrophy like physical exercise (FIG. 19C). Finally, grip strength was measured as the average of 6 measurements of the maximal peak strength generated on a grip strength meter (Bioseb), normalized to their body weight. The results showed that the drug combination X and Y significantly increased the grip strength of the inflammaging mice (P<0.01), indicating the drug combination X and Y increases limb muscle strength like physical exercise (FIG. 19D).

Figure 20:
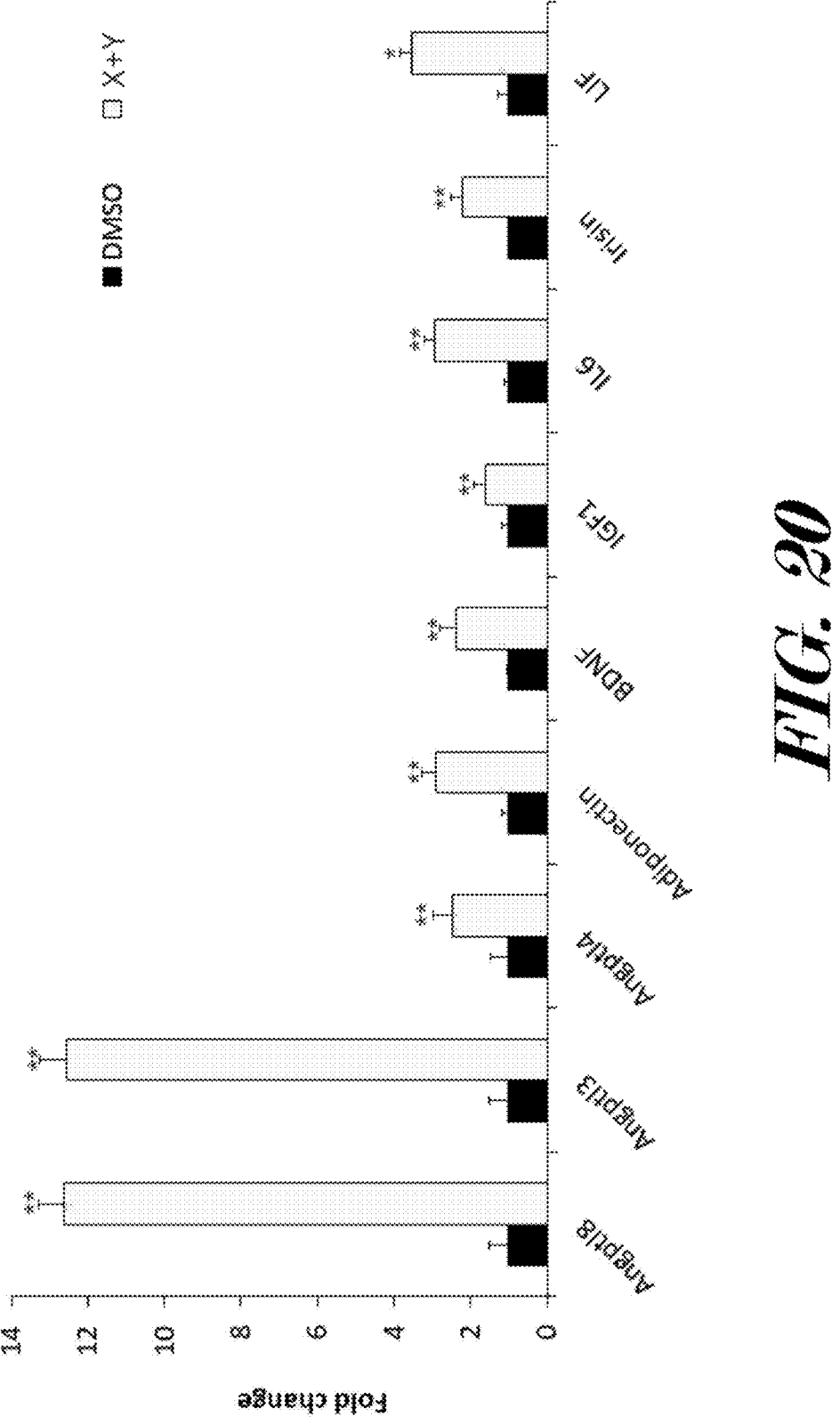
FIG. 20-FIG. 20 shows that drug combination X and Y induces many myokines/adipokines, as physical exercise does.

Example 10: Mimicry of Exercise Induces Secretory Factors to Suppress Inflammaging Physical muscular exercise is known to ameliorate the effects of aging, including chronic inflammaging and immunosenescence, by promoting the secretion of pro-metabolism and immunomodulatory cytokines. To test how the drug combination X and Y affects the effects of physical exercise via such secretory factors, the muscles of inflammaging mice were profiled with RNAseq and the serum of inflammaging mice were profiled with ELISA (R&D). The results showed that a variety of secretory factors, including myokines, were significantly increased by the drug combination X and Y (FIG. 20), including Angptl8, Angptl3, Angptl4, Adiponectin, BDNF, IGF1, IL6, Irisin and LIF (P<0.01), indicating that the drug combination X and Y affects aging and inflammaging, at least in part, by mimicking the effects of physical exercise and inducing many secretory factors including myokines.

Example 11: Mimicry of Calorie Restriction Induces Anti-Aging Gene Pathways

Figures 21A, 21B, 21C:
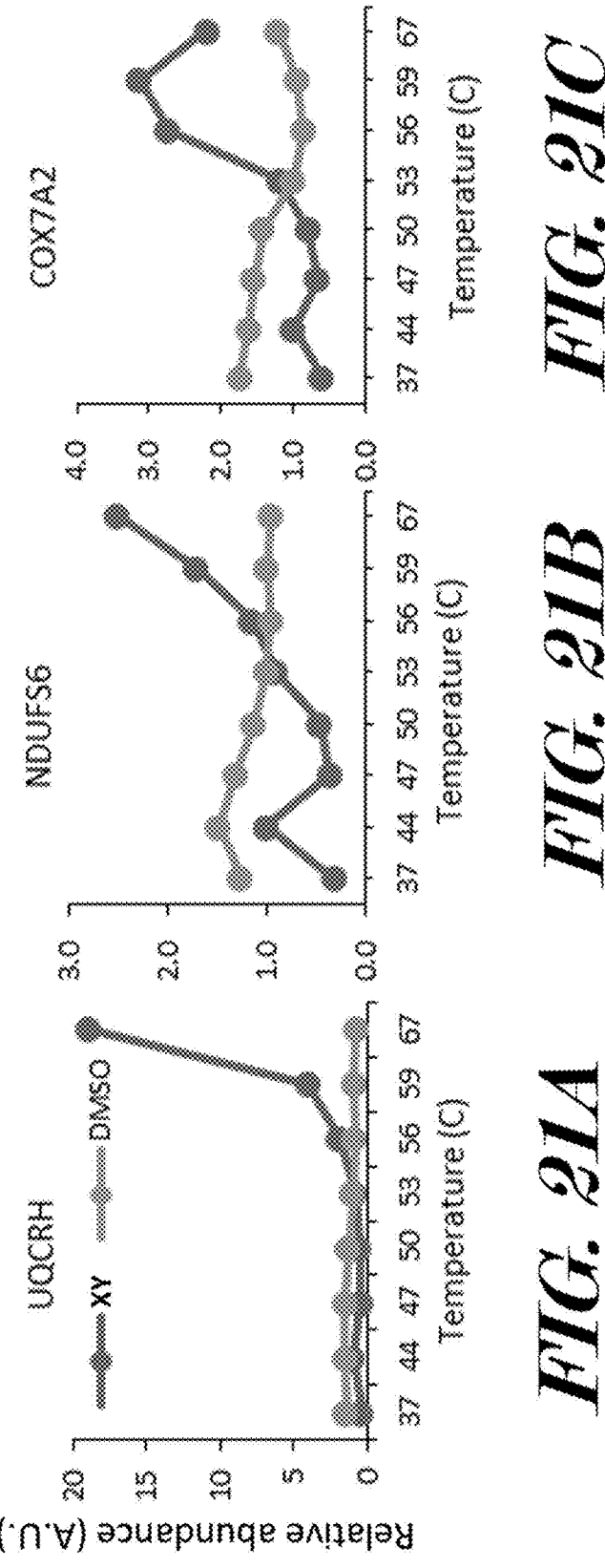
FIG. 21A-FIG. 21A shows that X and Y bound to mitochondrial protein UQCRH directly according to thermal proteome profiling with TMTpro 16plex kit and Q-Exactive HF-X mass spectrometry (Thermo Fisher).
FIG. 21B-FIG. 21B shows that X and Y bound to mitochondrial protein NDUFS6 directly according to thermal proteome profiling with TMTpro 16plex kit and Q-Exactive HF-X mass spectrometry (Thermo Fisher).
FIG. 21C-FIG. 21C shows that X and Y bound to mitochondrial protein COX7A2 directly according to thermal proteome profiling with TMTpro 16plex kit and Q-Exactive HF-X mass spectrometry (Thermo Fisher).
Figure 22:
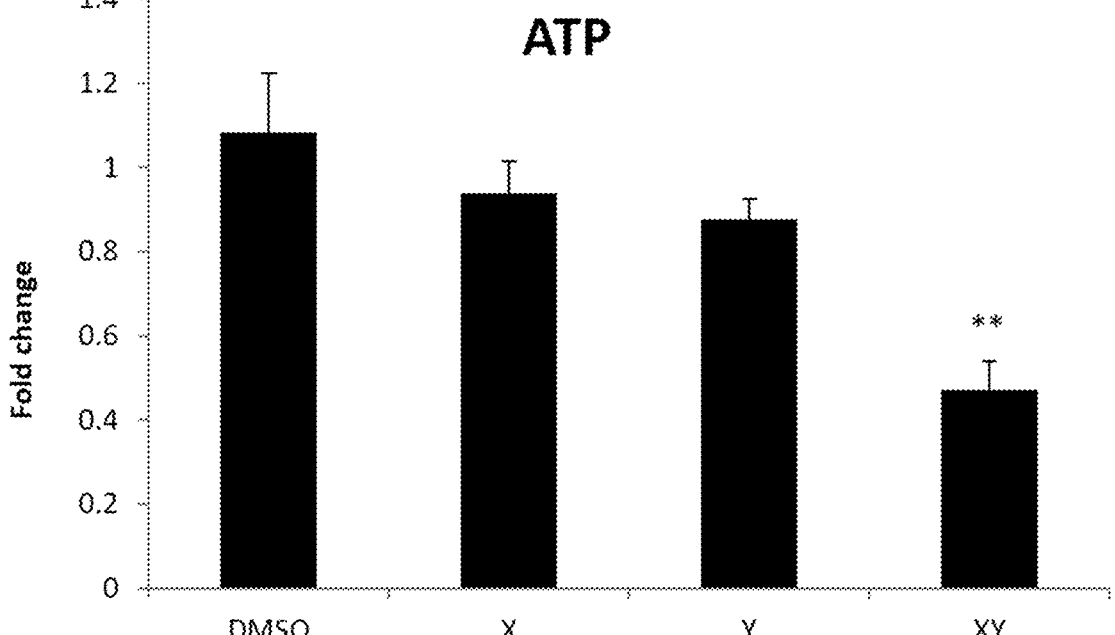
FIG. 22-FIG. 22 shows that X and Y synergistically decreased ATP levels within minutes.
Figure 23:
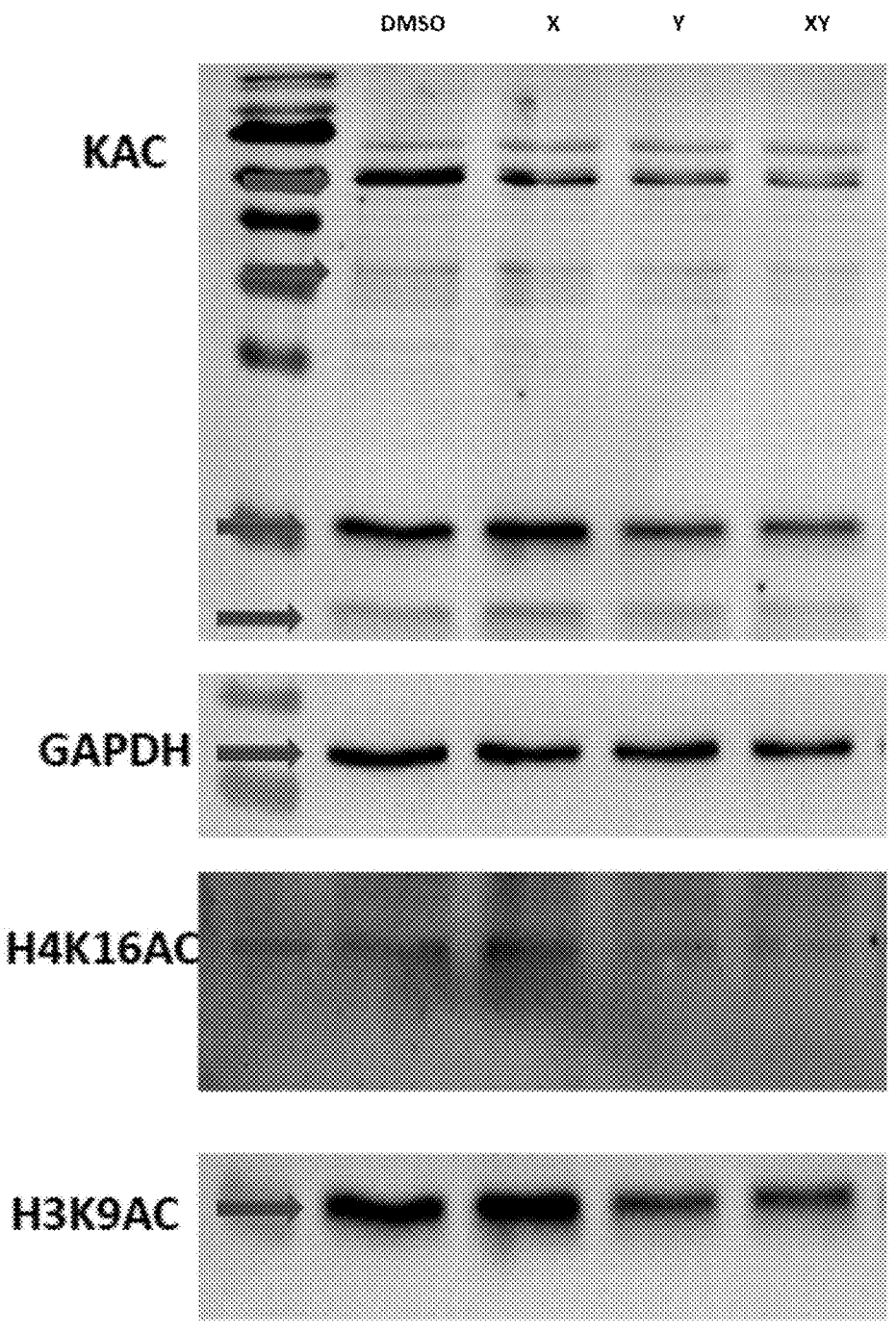
FIG. 23-FIG. 23 shows that X and Y synergistically decreased acety-CoA and protein acetylation.
Figure 24:
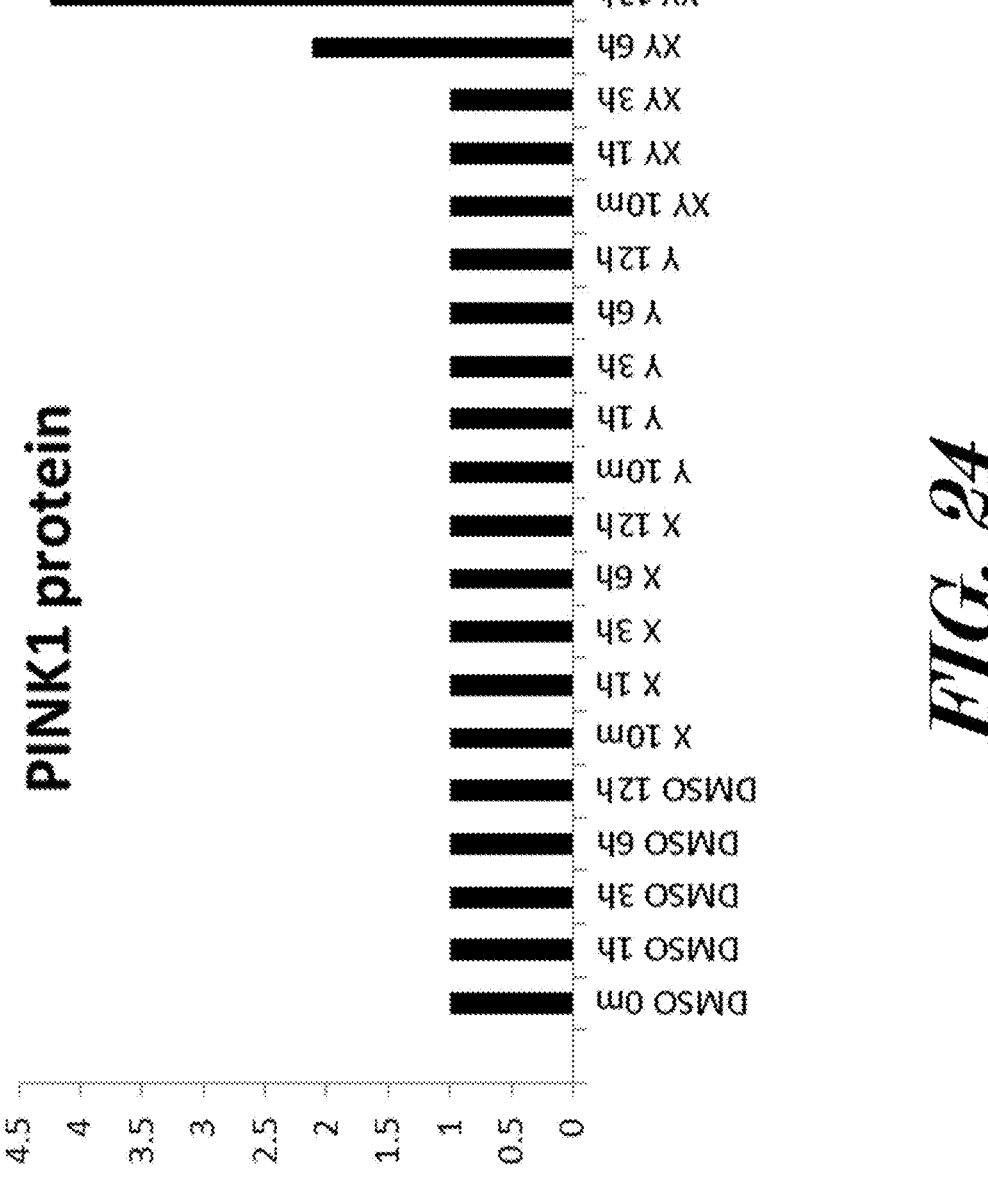
FIG. 24-FIG. 24 shows that X and Y synergistically increased Pink1 for Parkin-driven mitophagy according to immunostaining with Abcam ab23707 antibody.
Figure 25A:
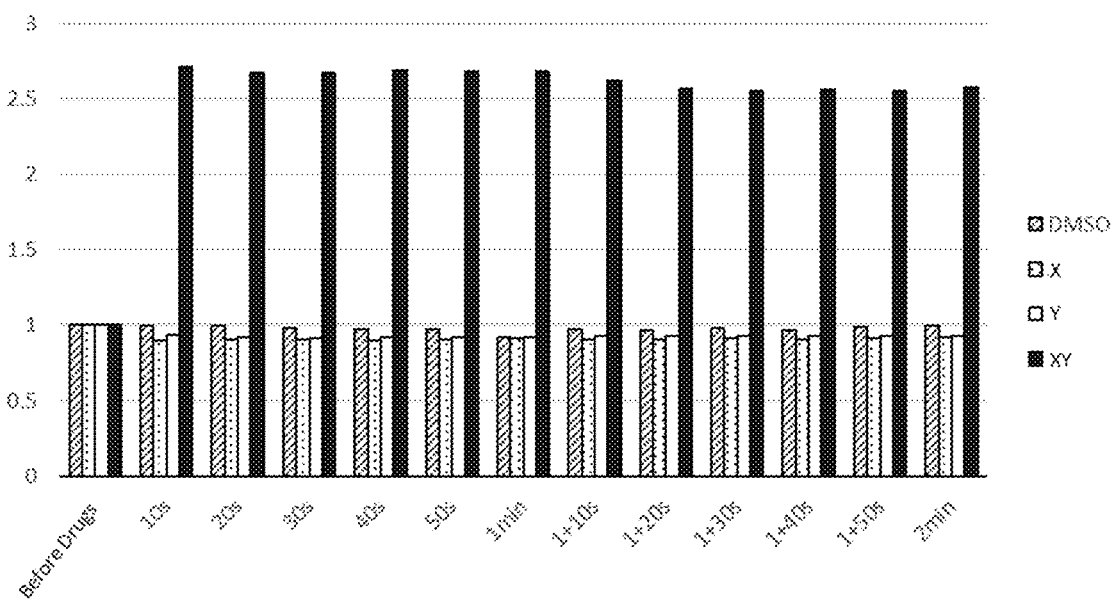
FIG. 25A-FIG. 25A shows that X and Y synergistically increased mitochondrial-targeted myoblast protein levels.
Figure 25B:
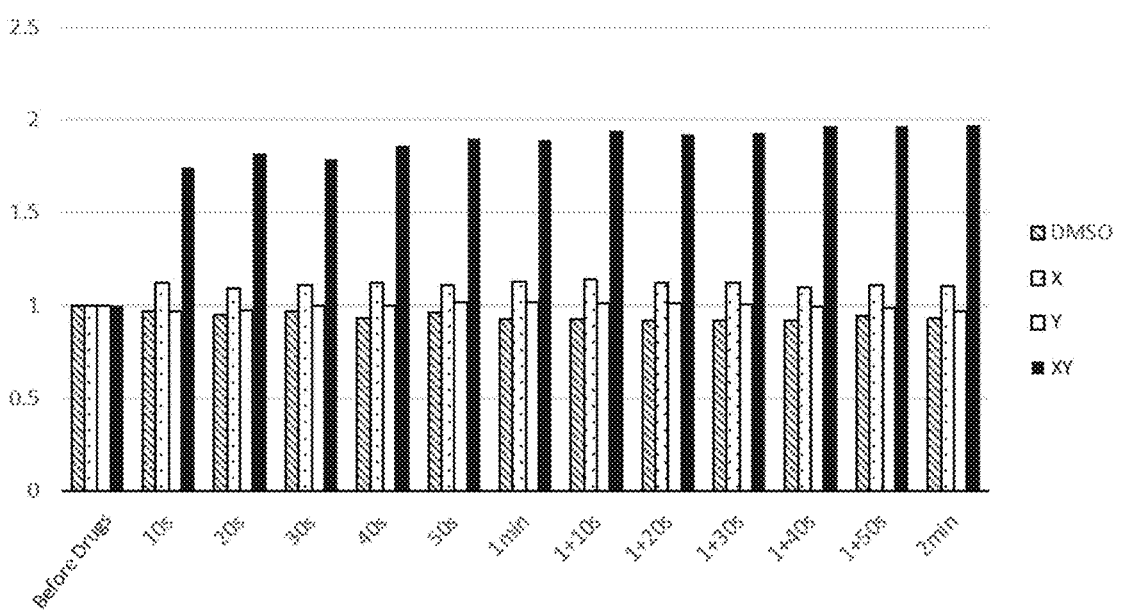
FIG. 25B-FIG. 25B shows that X and Y synergistically increased mitochondrial-targeted myotube protein levels.
Figure 26:
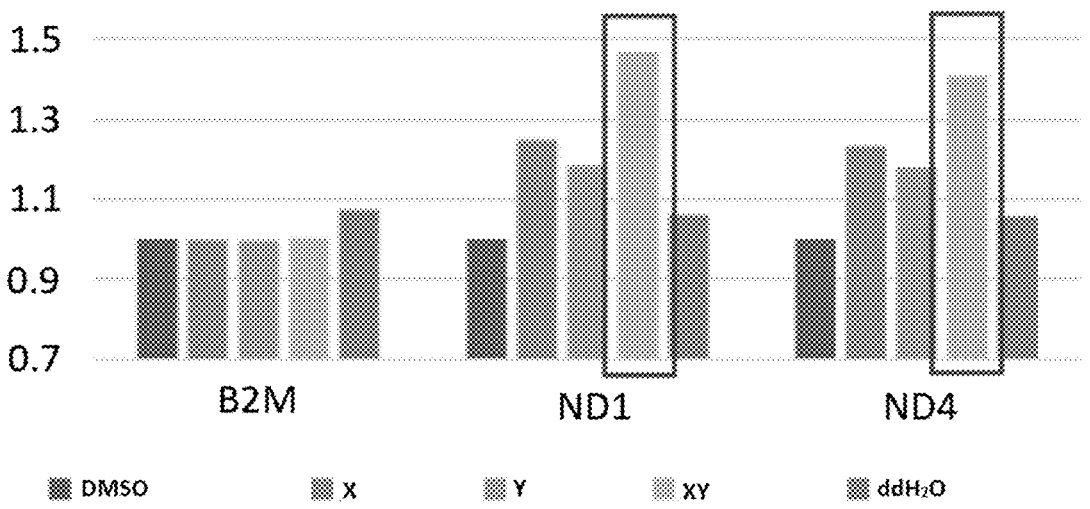
FIG. 26-FIG. 26 shows that X and Y synergistically increased mitochondrial DNA levels according to qRT-PCR for mitochondrial genomic NADH dehydrogenases ND1 and ND4 relative to nuclear genomic B2M.
Figure 27:
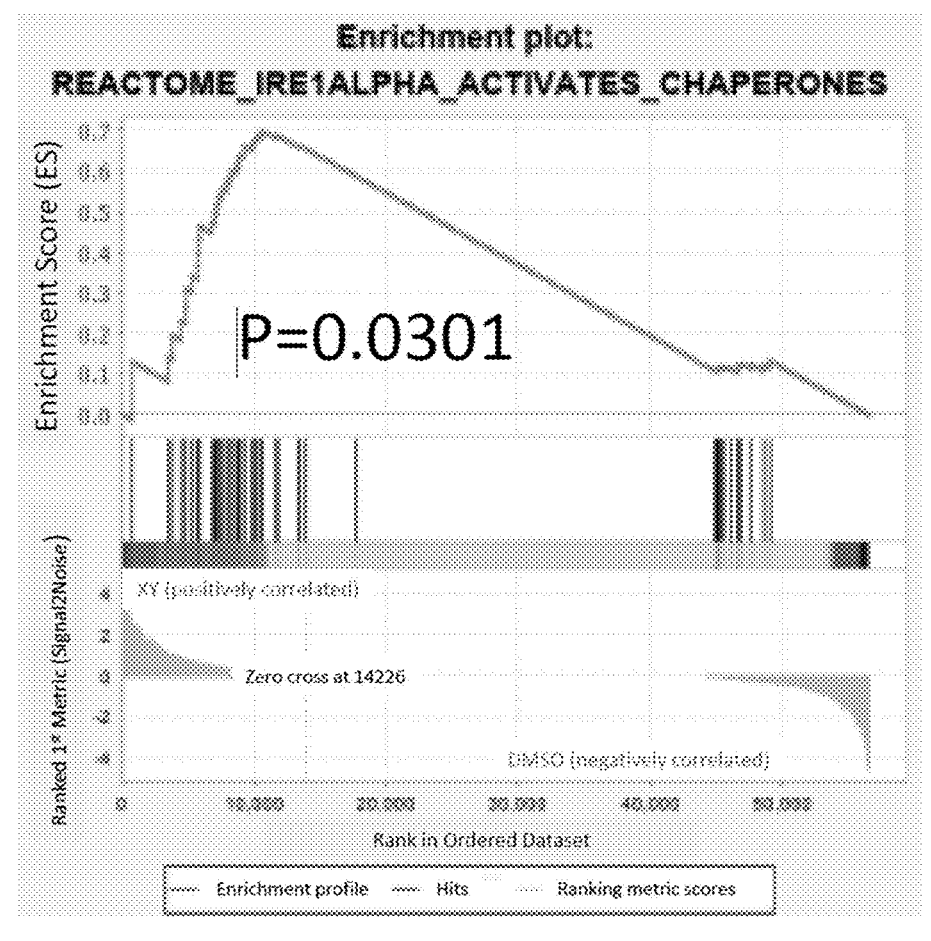
FIG. 27-FIG. 27 shows that X and Y synergistically increased the IRE1a-mediated unfolded protein response (UPR) according to RNAseq (Illumina HiSeq).
Figure 28A:
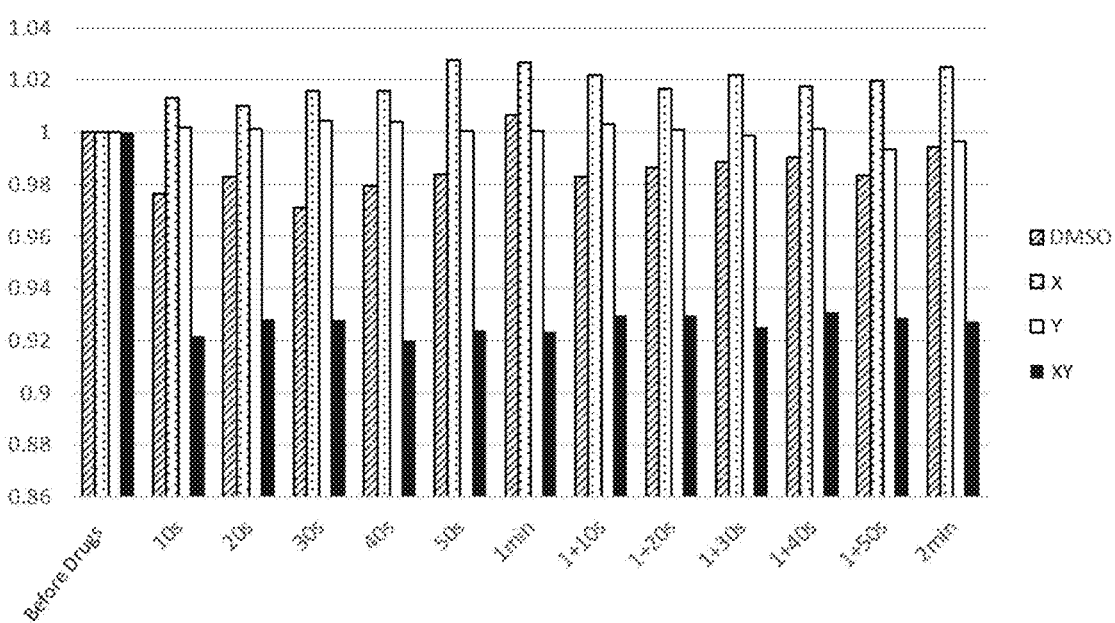
FIG. 28A-FIG. 28A shows that X and Y synergistically decreased the mitochondrial reactive oxygen species (ROS).
Figure 28B:
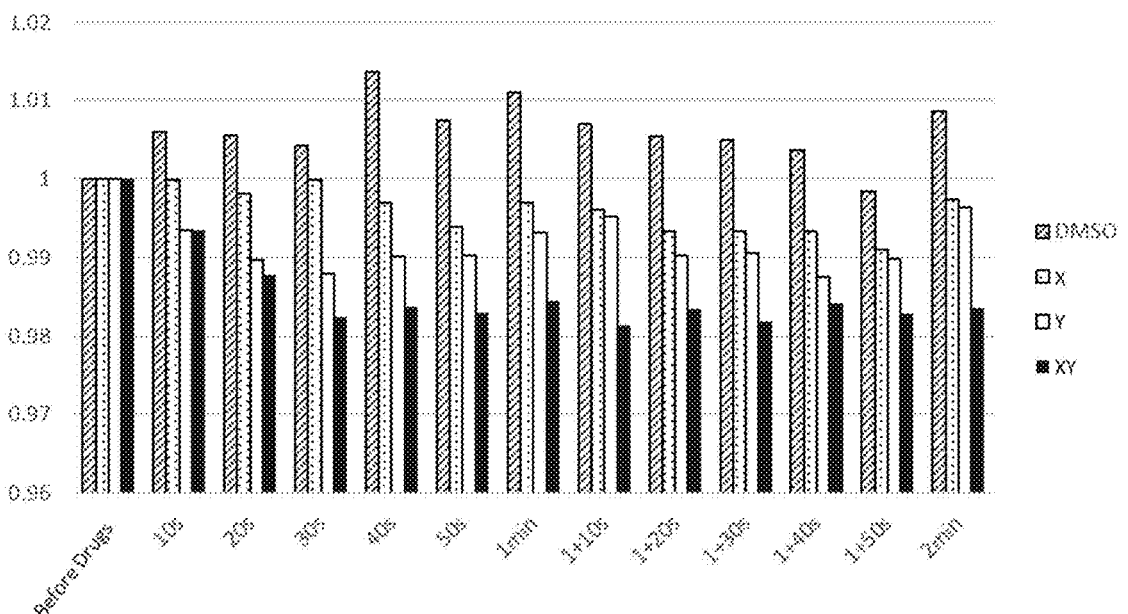
FIG. 28B-FIG. 28B shows that X and Y synergistically decreased the mitochondrial reactive oxygen species (ROS).
Figure 29A:
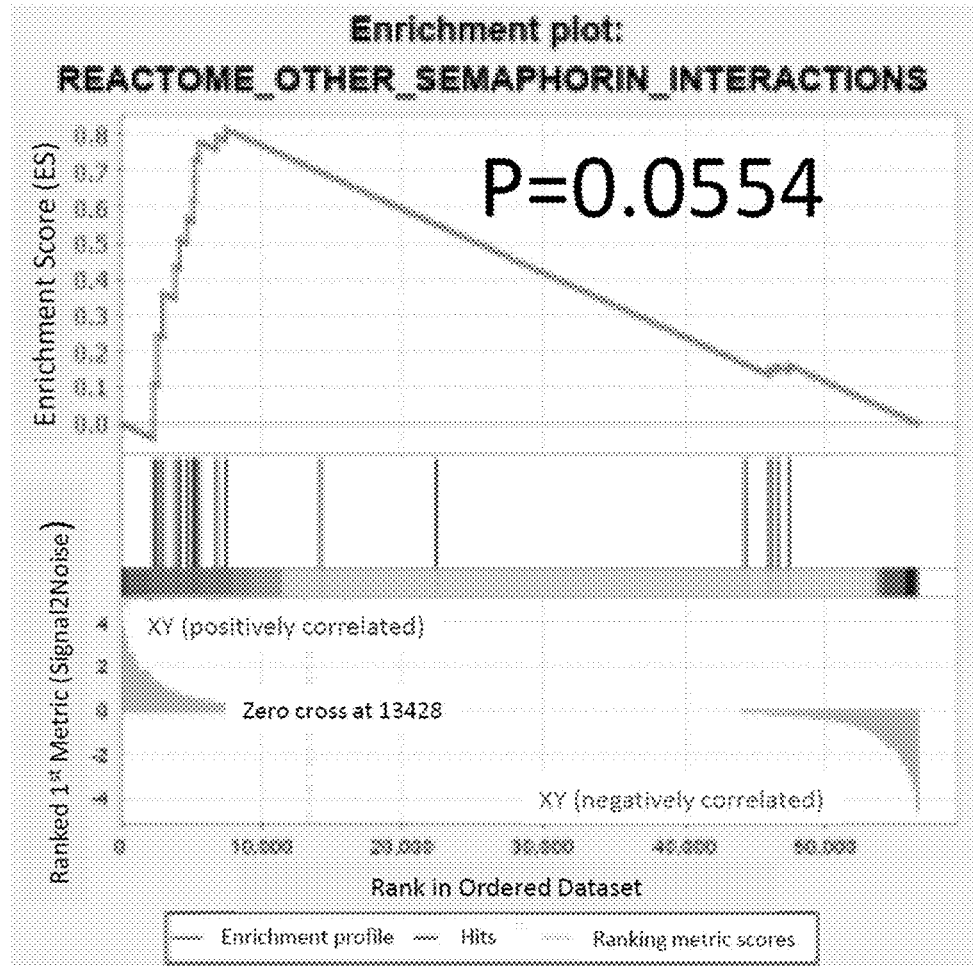
FIG. 29A-FIG. 29A shows that X and Y synergistically increased the activity of a variety of cytokine pathways (FIG. 17), including semaphorins, indicating that the drug combination X and Y delays aging by stimulating the neuroendocrine system and mimicking calorie restriction.
Figure 29B:
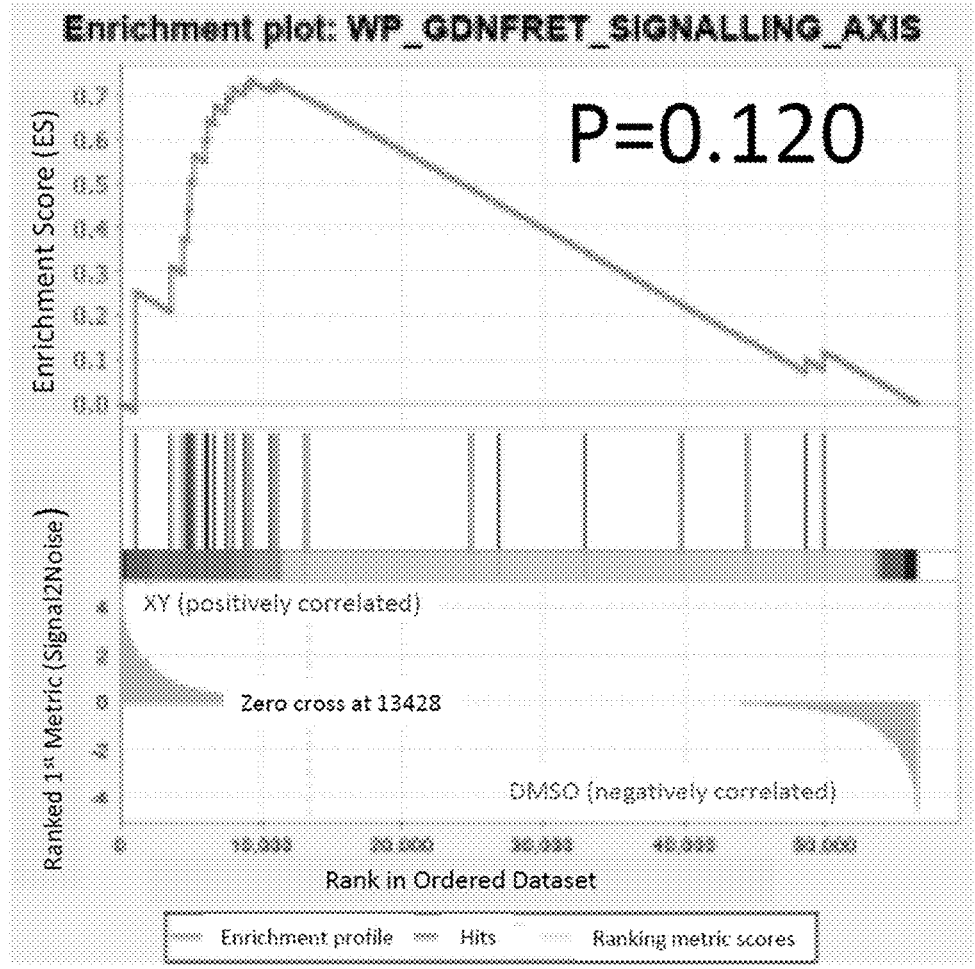
FIG. 29B-FIG. 29B shows that X and Y synergistically increased the activity of a variety of cytokine pathways (FIG. 17), including GDNF, indicating that the drug combination X and Y delays aging by stimulating the neuroendocrine system and mimicking calorie restriction.
Figure 29C:
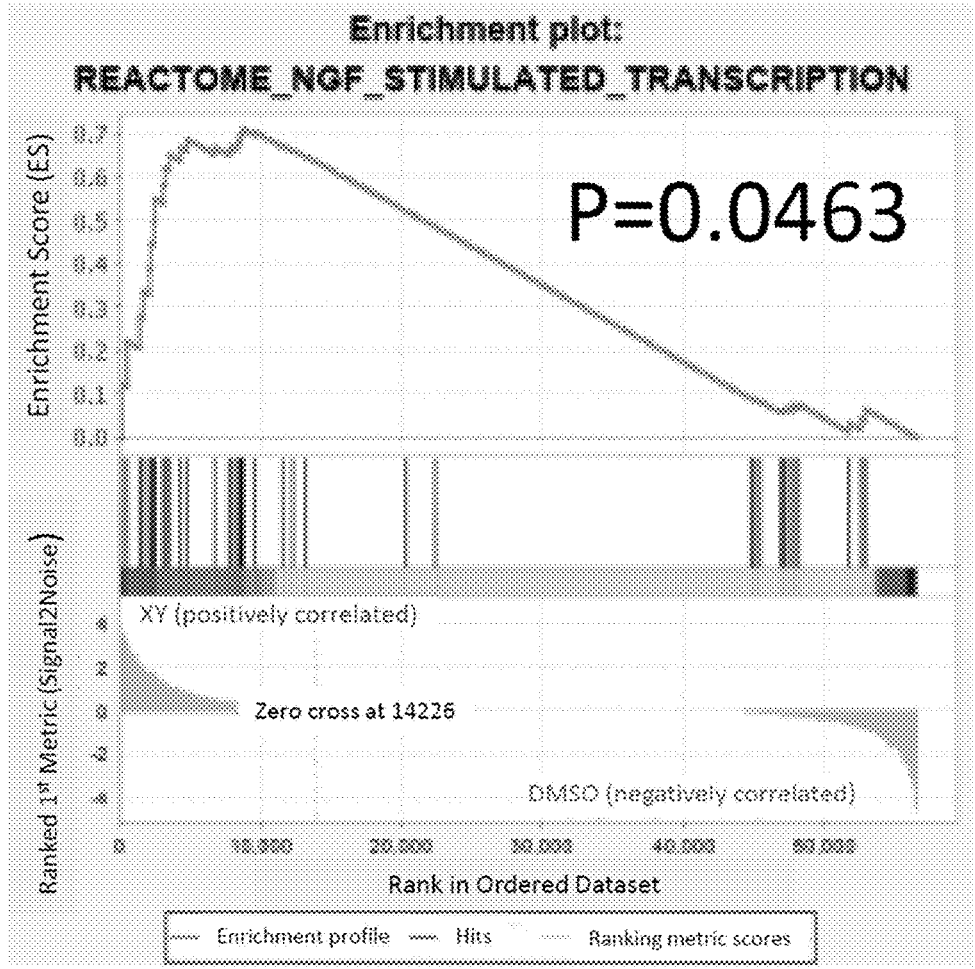
FIG. 29C-FIG. 29C shows that X and Y synergistically increased the activity of a variety of cytokine pathways (FIG. 17), including NGF, indicating that the drug combination X and Y delays aging by stimulating the neuroendocrine system and mimicking calorie restriction.
Figure 30A:
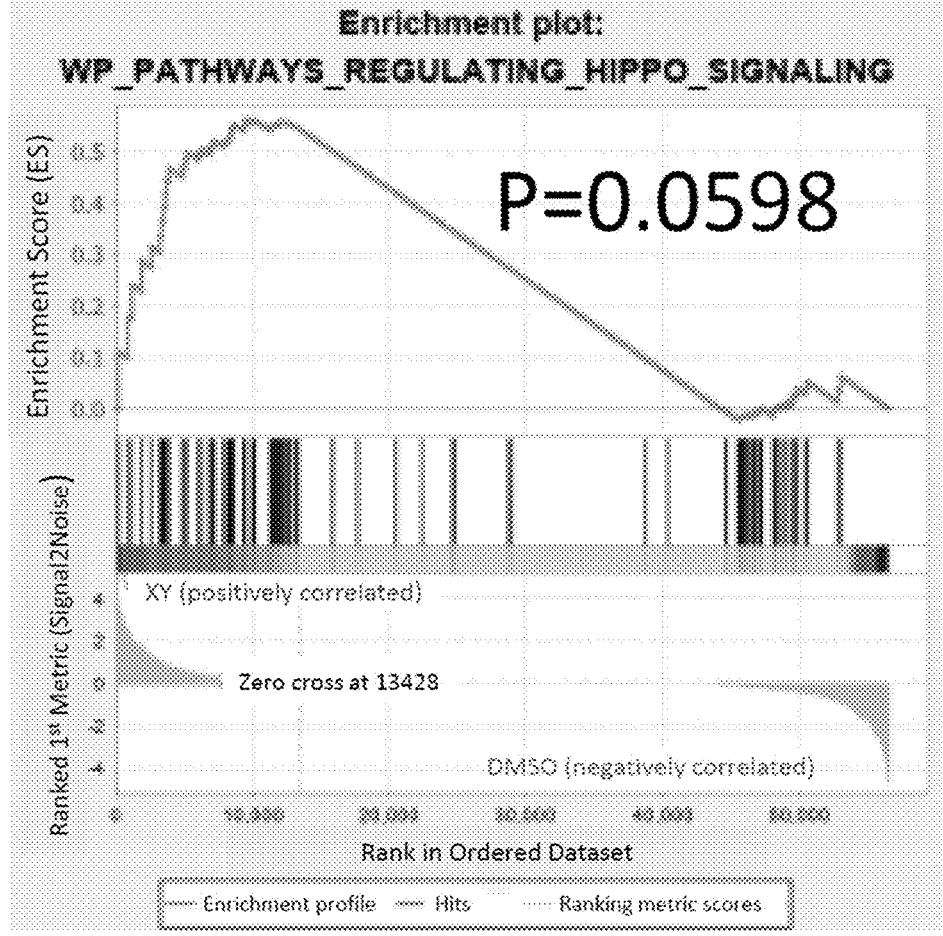
FIG. 30A-FIG. 30A shows that the drug combination X and Y synergistically increased the expression of stem cell pathways according to RNAseq (Illumina Hiseq), such as Hippo, Notch-Hes-Hey, HIF1a, and integrin-MAPK, indicating increased stemness and regenerative capacity.
Figure 30B:
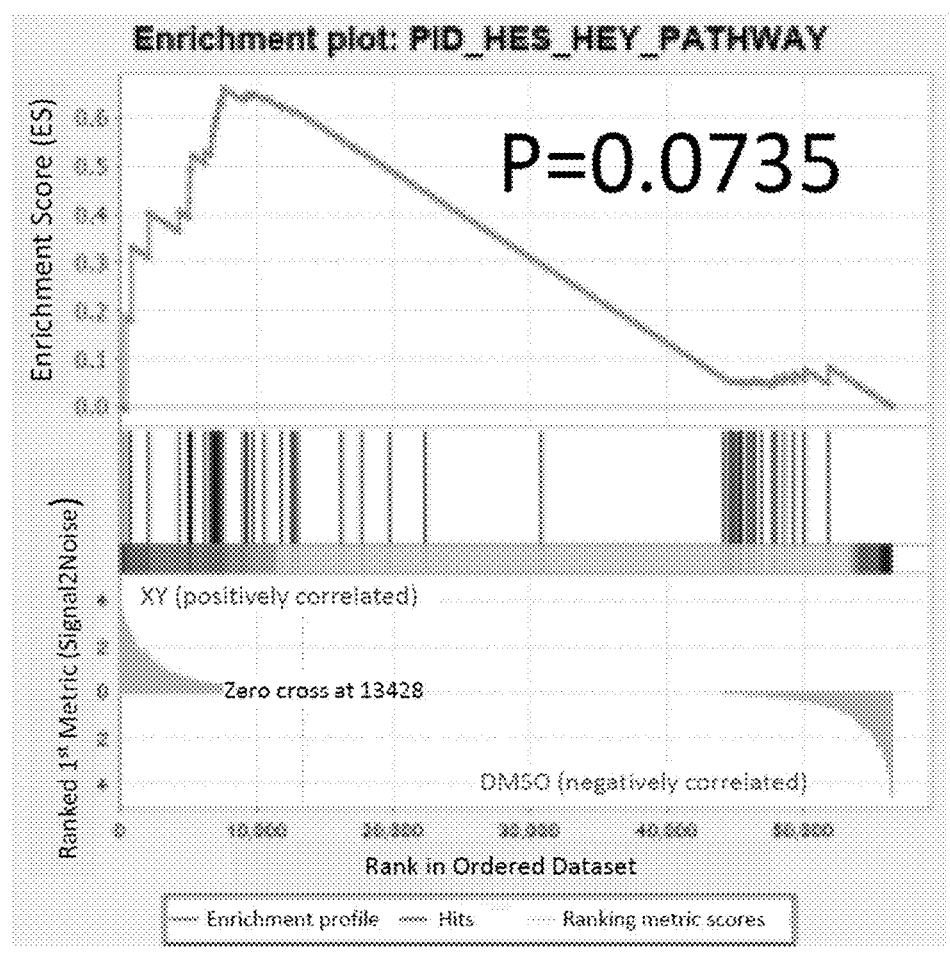
FIG. 30B-FIG. 30B shows that the drug combination X and Y synergistically increased the expression of stem cell pathways according to RNAseq (Illumina Hiseq), such as Hippo, Notch-Hes-Hey, HIF1a, and integrin-MAPK, indicating increased stemness and regenerative capacity.
Figure 30C:
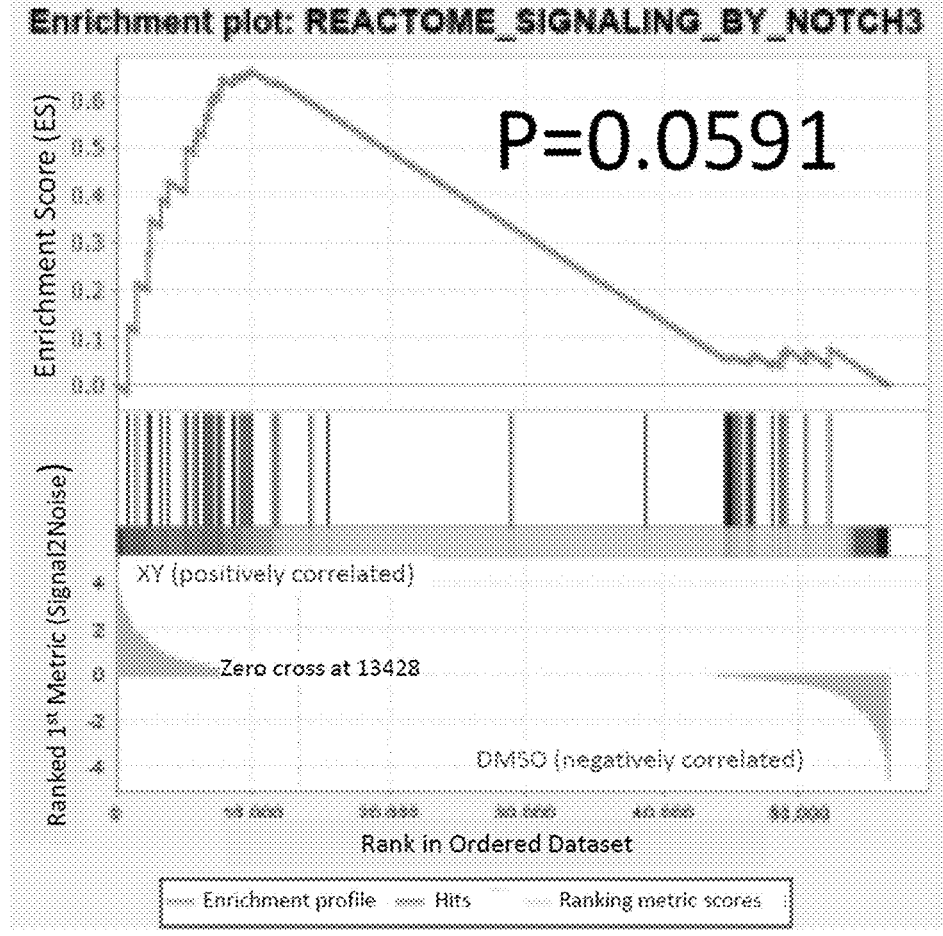
FIG. 30C-FIG. 30C shows that the drug combination X and Y synergistically increased the expression of stem cell pathways according to RNAseq (Illumina Hiseq), such as Hippo, Notch-Hes-Hey, HIF1a, and integrin-MAPK, indicating increased stemness and regenerative capacity.
Figure 30D:
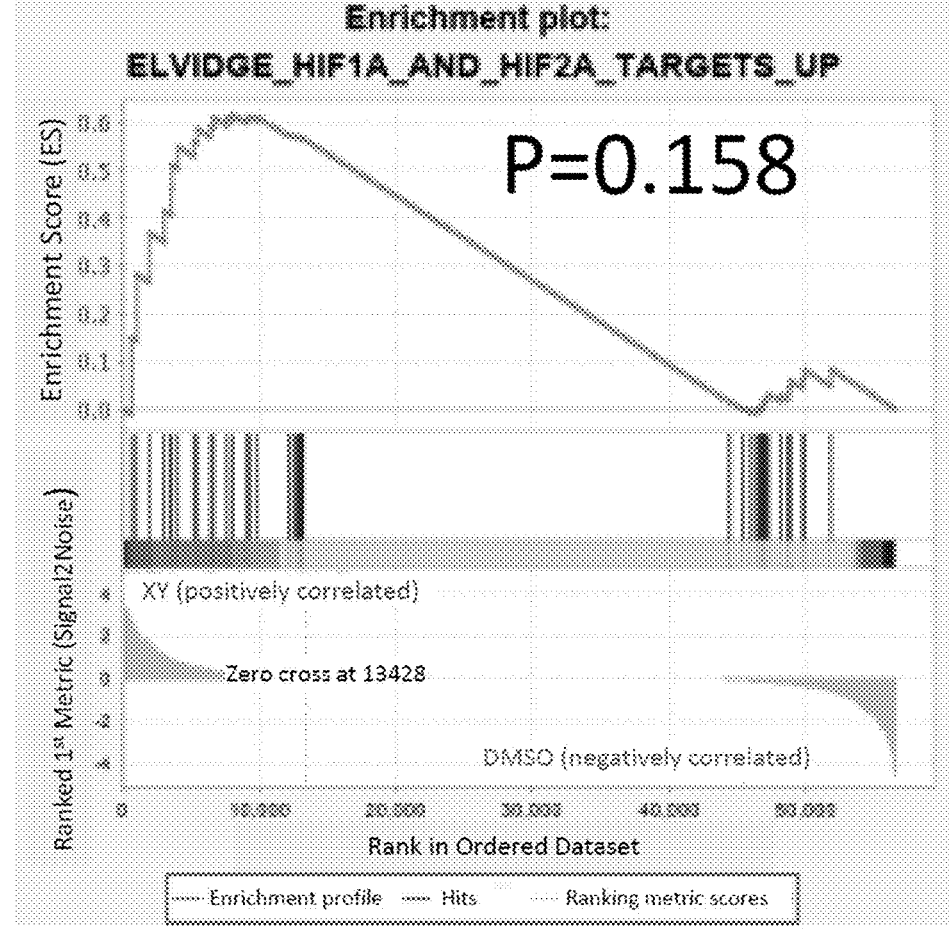
FIG. 30D-FIG. 30D shows that the drug combination X and Y synergistically increased the expression of stem cell pathways according to RNAseq (Illumina Hiseq), such as Hippo, Notch-Hes-Hey, HIF1a, and integrin-MAPK, indicating increased stemness and regenerative capacity.
Figure 30E:
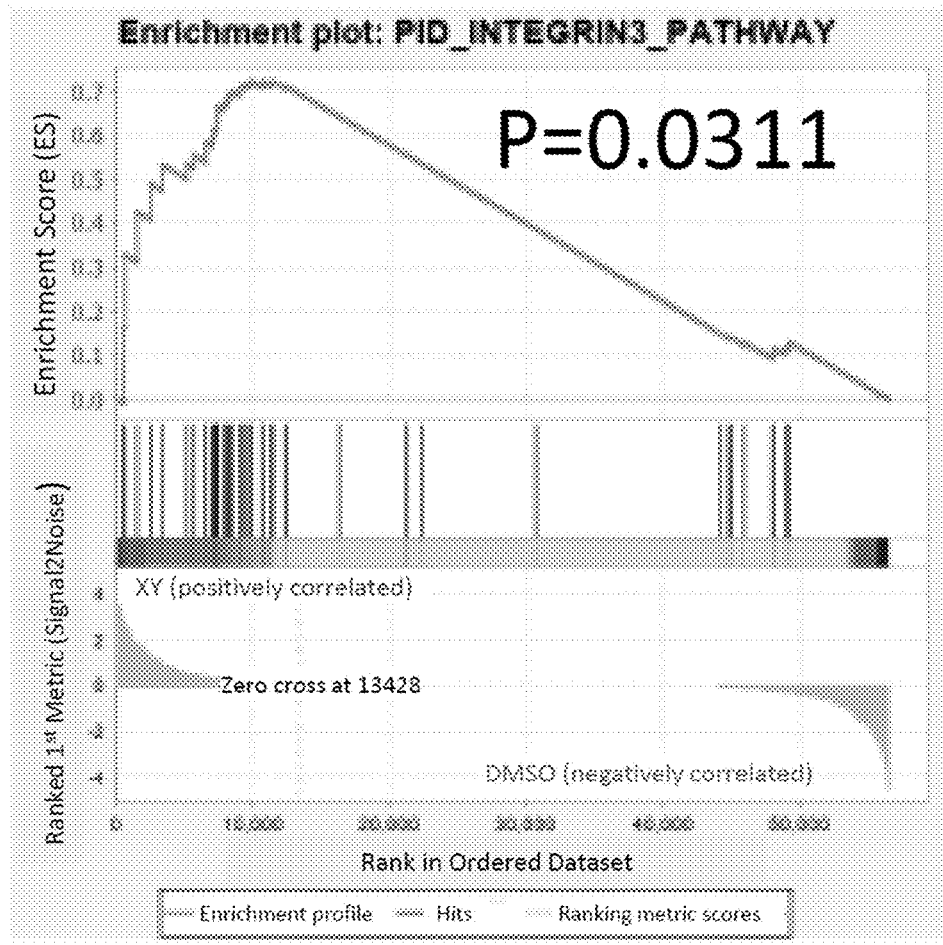
FIG. 30E-FIG. 30E shows that the drug combination X and Y synergistically increased the expression of stem cell pathways according to RNAseq (Illumina Hiseq), such as Hippo, Notch-Hes-Hey, HIF1a, and integrin-MAPK, indicating increased stemness and regenerative capacity.

Calorie restriction is known to ameliorate the effects of aging, by altering cellular bioenergetic stress and promoting mitochondrial activity, the unfolded protein response (UPR), the secretion of beneficial cytokines, and an increase in stem cell regeneration. To test how the drug combination X and Y mimics the effects of calorie restriction (CR), we profiled the metabolism of primary human skeletal muscle cells at passage 15 treated with X (100 mg/L) and Y (2 mg/L), compared to X alone (100 mg/L) or Y alone (2 mg/L). The results showed that X and Y bound to mitochondrial proteins UQCRH, NDUFS6, and COX7A2 directly according to thermal proteome profiling with TMTpro 16plex kit and Q-Exactive HF-X mass spectrometry (Thermo Fisher; FIGS. 21A-21C), synergistically decreased ATP levels within minutes (FIG. 22), synergistically decreased acetyl-CoA and protein acetylation (FIG. 23), synergistically increased Pink1 for Parkin-driven mitophagy according to immunostaining with the Abcam ab23707 antibody (FIG. 24), synergistically increased mitochondrial-targeted protein levels (FIGS. 25A and 25B), synergistically increased mitochondrial DNA levels according to qRT-PCR for mitochondrial genomic ND1 and ND4 relative to nuclear genomic B2M (FIG. 26), synergistically increased the IRE1a-mediated unfolded protein response (UPR) according to RNAseq (Illumina HiSeq) and gene set enrichment analysis (GSEA) (FIG. 27), and synergistically decreased the mitochondrial reactive oxygen species (ROS; FIGS. 28A and 28B). X and Y synergistically increased the activity of a variety of cytokine pathways according to gene set enrichment analysis (GSEA) (FIGS. 29A-29C), including NGF, GDNF, and semaphorins, indicating that the drug combination X and Y delays aging by stimulating the neuroendocrine system and mimicking calorie restriction. Finally, the drug combination X and Y synergistically increased the expression of stem cell pathways according to RNAseq (Illumina Hiseq) and gene set enrichment analysis (GSEA), such as Hippo, Notch-Hes-Hey, HIF1a, and integrin-MAPK (FIGS. 30A-30E), indicating increased stemness and regenerative capacity. None of these beneficial anti-aging effects were observed with either X alone or Y alone or the vehicle.

Example 12: Induction of Anti-Aging, Pro-Regenerative Responses In Vivo

Figure 31:
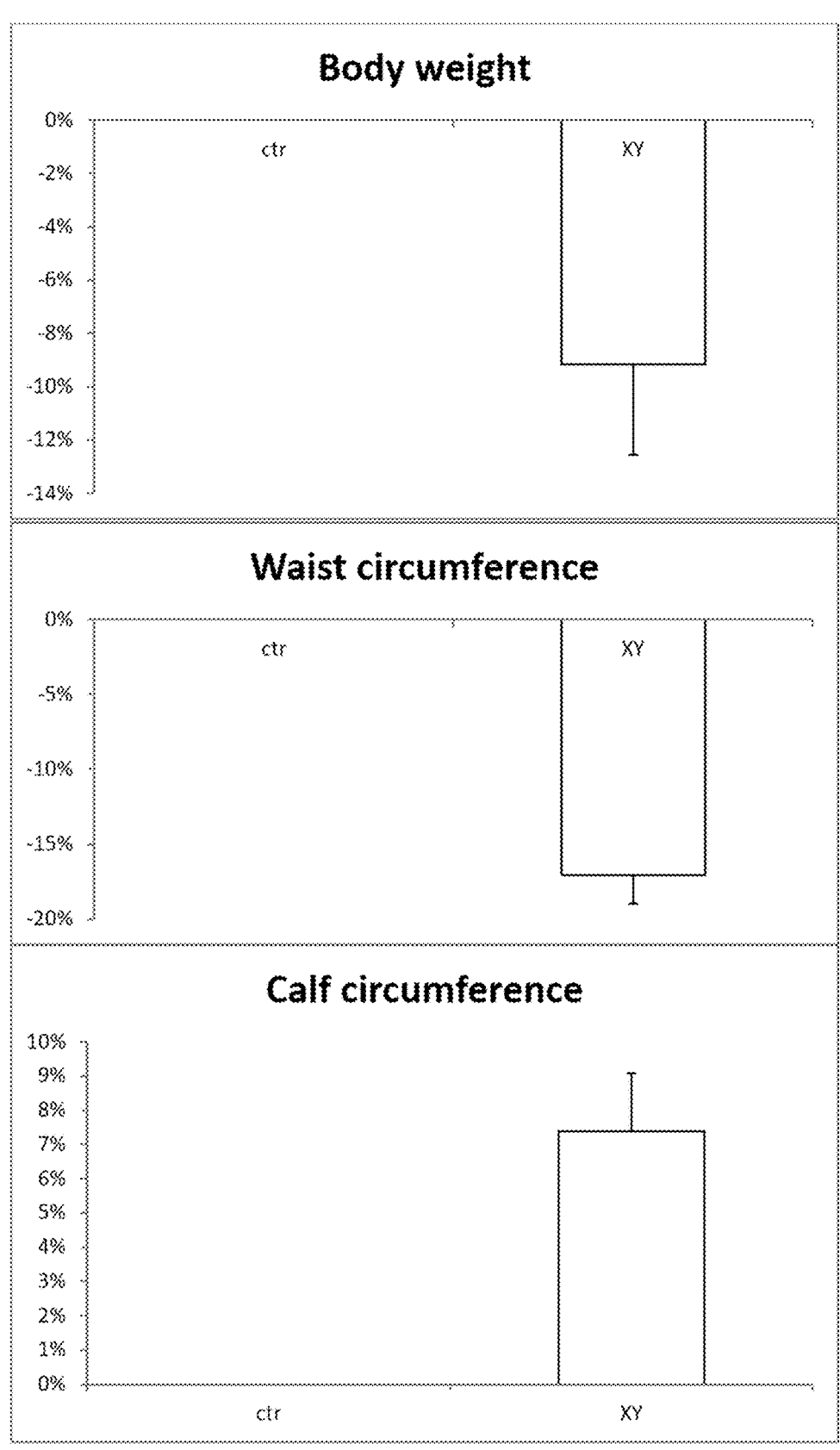
FIG. 31-FIG. 31 shows that after 2 rounds of transdermal treatment with X and Y, the cynomolgus monkeys' total body weight and waist circumference (an indicator of aging-induced central adiposity) both decreased significantly by ~10-20%, while the calf circumference (an indicator of skeletal muscle growth and regeneration) increased by ~8%.
Figure 32A:
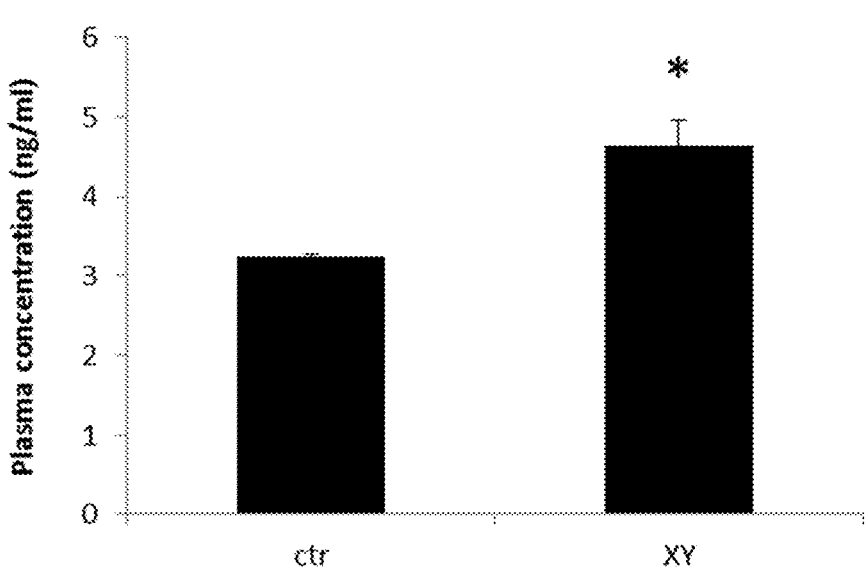
FIG. 32A-FIG. 32A shows that the cynomolgus monkeys' plasma levels of the neuroendocrine cytokine BDNF (R&D Systems ELISA) were also significantly increased after treatment with the drug combination X and Y, but not X alone or Y alone or the vehicle.
Figure 32B:
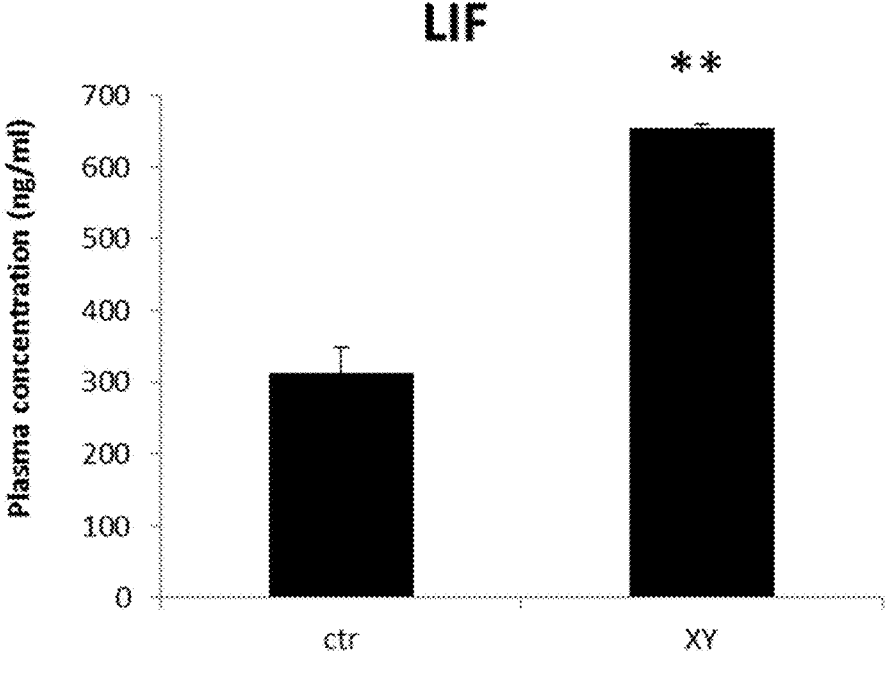
FIG. 32B-FIG. 32B shows that the cynomolgus monkeys' plasma levels of the neuroendocrine cytokine LIF (R&D Systems ELISA) were also significantly increased after treatment with the drug combination X and Y, but not X alone or Y alone or the vehicle.
Figure 33A:
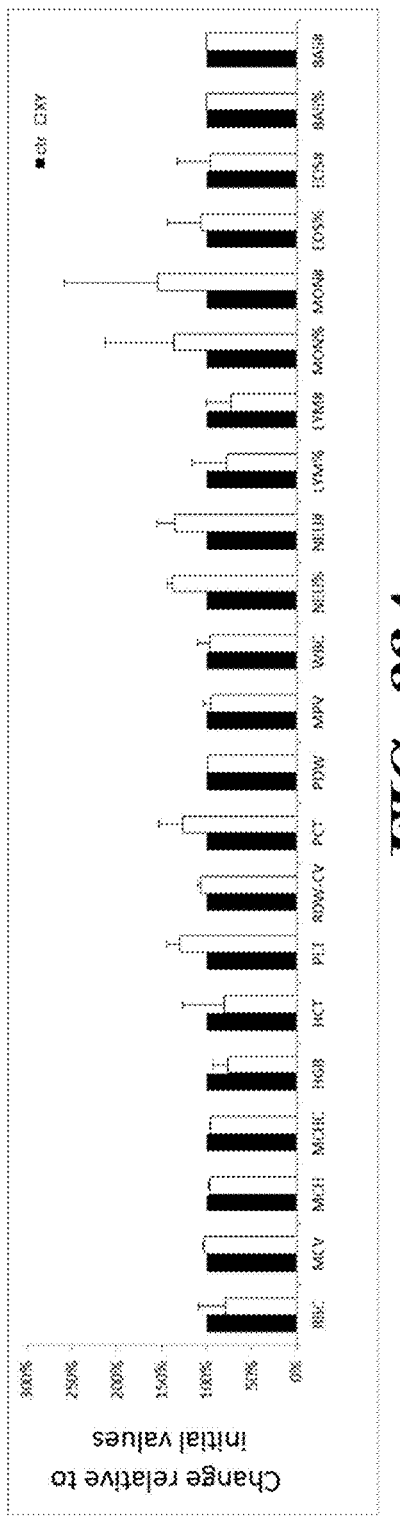
FIG. 33A-FIG. 33A shows that no toxicities associated with drug combination X and Y were observed according to clinical hematology or clinical blood chemistry (FIG. 21).
Figure 33B:
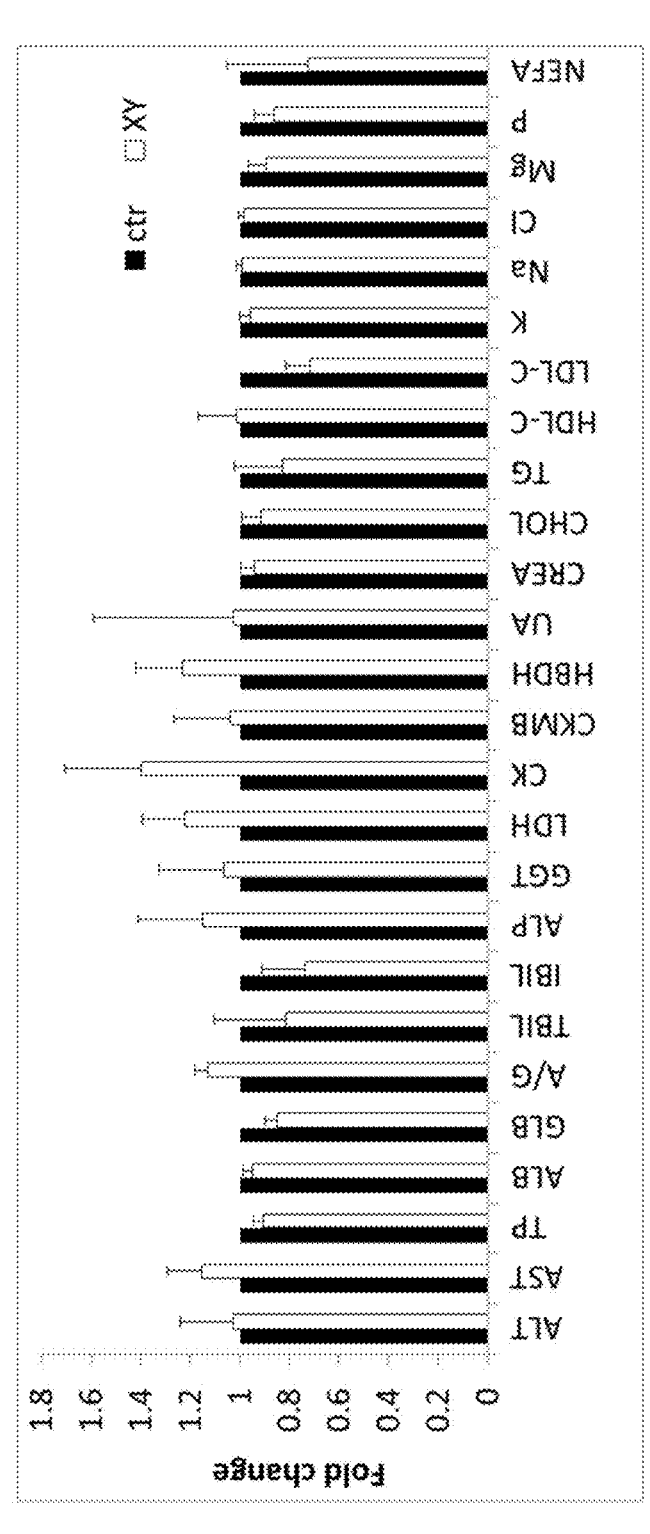
FIG. 33B-FIG. 33B shows that no toxicities associated with drug combination X and Y were observed according to clinical hematology or clinical blood chemistry (FIG. 21).

Application of the drug combination X and Y in cynomolgus monkeys increased neuroendocrine cytokines like calorie restriction, thereby increasing anti-aging-associated muscle regeneration and decreasing aging-associated central adiposity. By dissolving X and Y in DURO-TAK 87-2677 PSA (pressure-sensitive adhesive) solution, and coating it on a release film (Scotchpak™ 1022), followed by bake-drying and laminating with a backing film (Scotchpak™ 1109), we constructed a drug-in-adhesive patch for controlled transdermal release of the drugs X and Y every 7 days. After 2 rounds of transdermal drug treatment, we found that the cynomolgus monkeys' total body weight and waist circumference (an indicator of aging-induced central adiposity)

both decreased significantly by ~10-20%, while the calf circumference (an indicator of skeletal muscle growth and regeneration) increased by ~8% (FIG. 31). Importantly, their plasma levels of the neuroendocrine cytokines BDNF and LIF (R&D Systems ELISA) were also significantly increased after treatment with the drug combination X and Y, but not X alone or Y alone or the vehicle (FIGS. 32A and 32B). No toxicities were observed according to clinical hematology or clinical blood chemistry (FIGS. 33A and 33B).

Figure 34:
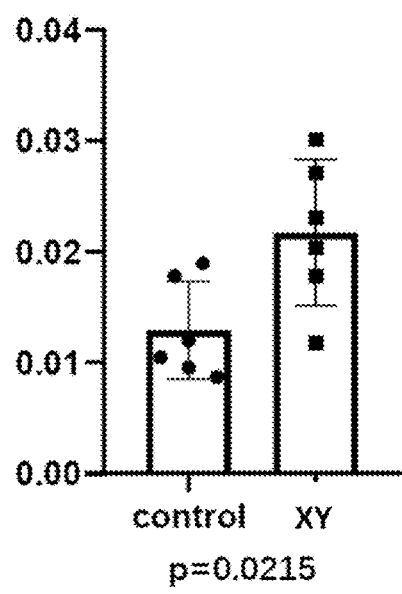
FIG. 34-FIG. 34 shows that X and Y promoted liver regeneration in 1-year-old aged diabetic mice with livers with aging-associated steatohepatitis, relative to X alone or Y alone or the vehicle as observed from increased hepatocyte proliferation indicated by Ki67 (Abcam ab16667) immunostaining.
Figure 35:
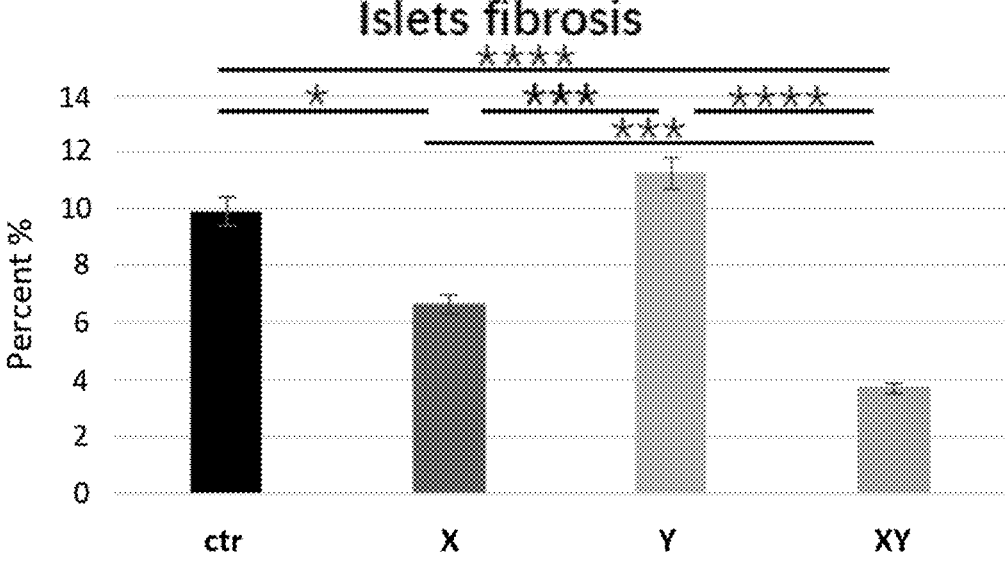
FIG. 35-FIG. 35 shows that drug combination X and Y decreased β islet fibrosis in pancreas with aging-associated pancreatitis due to type 2 diabetes, according to Masson's trichrome staining.
Figure 36A:
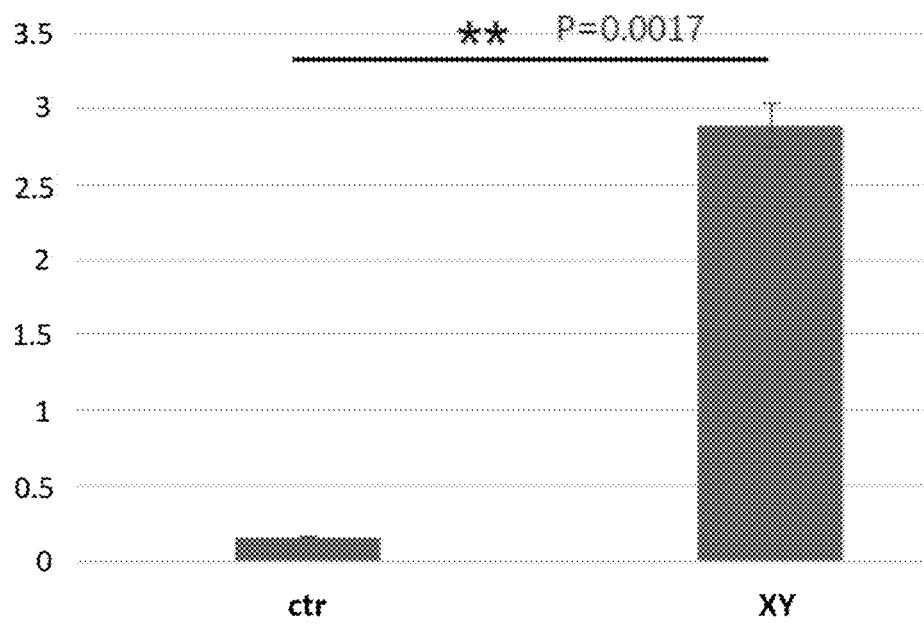
FIG. 36A-FIG. 36A shows that drug combination X and Y increased β islet cell growth and proliferation according to Ki67 (Abcam ab16667) immunostaining FIG. 36B
Figure 36B:
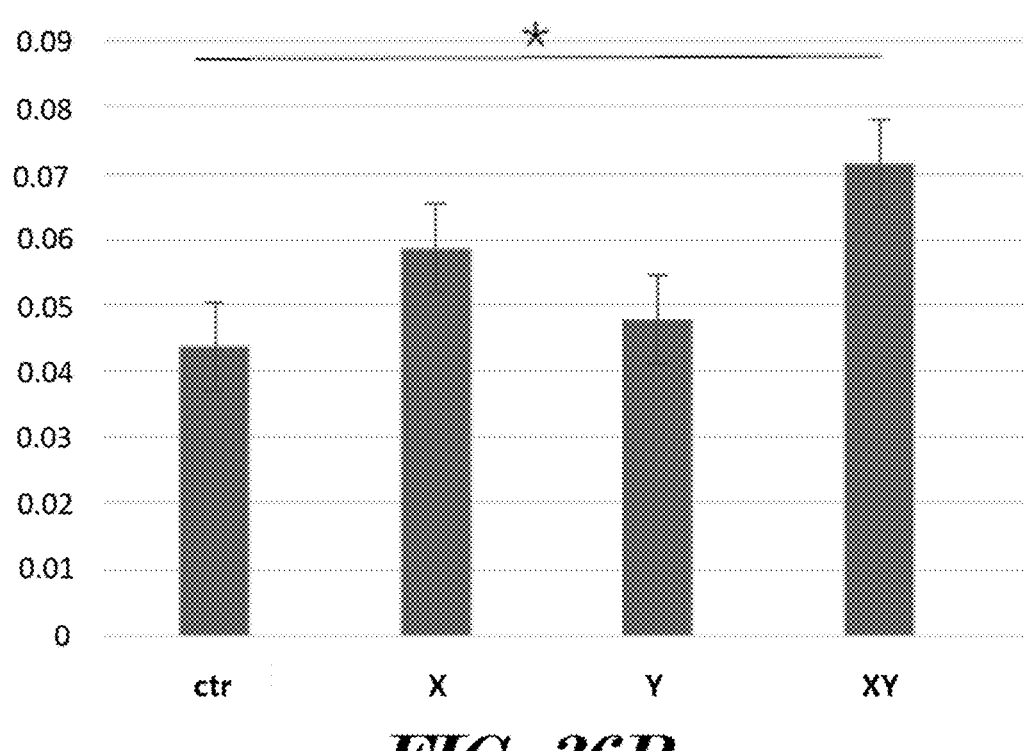
-FIG. 36B shows that drug combination X and Y increased β islet cell growth and proliferation according to Ki67 (Abcam ab16667) immunostaining FIG. 37A
Figure 38:
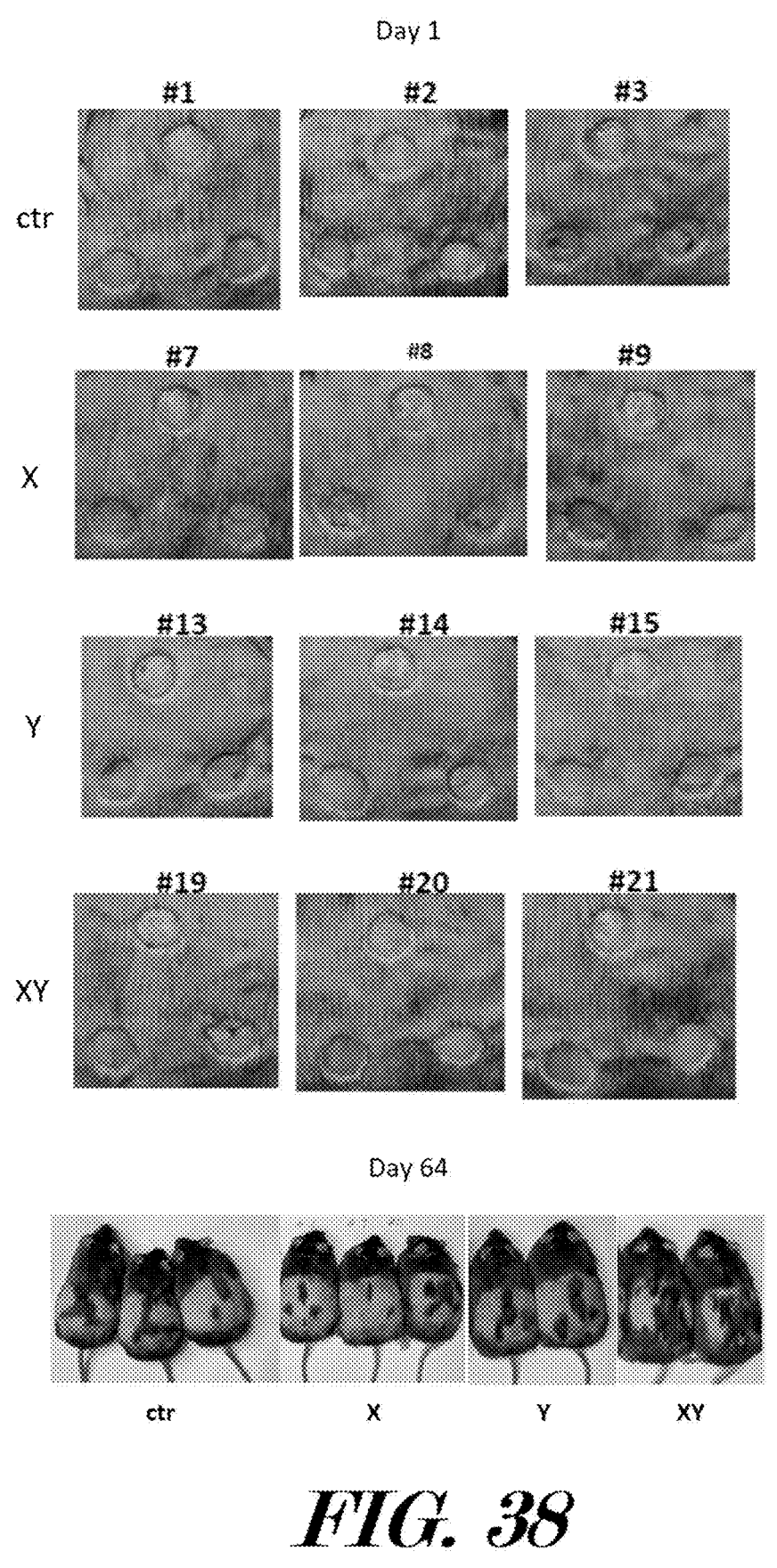
Figure 39:
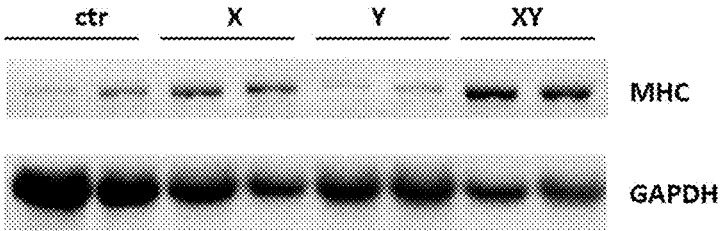
FIG. 39-FIG. 39 shows that, X and Y increased the protein levels of myosin heavy chain (MHC; Sigma-Aldrich-M4276 antibody) in the quadriceps muscles of 1-year-old diabetic mice, thereby promoting skeletal muscle regeneration.
Figure 40:
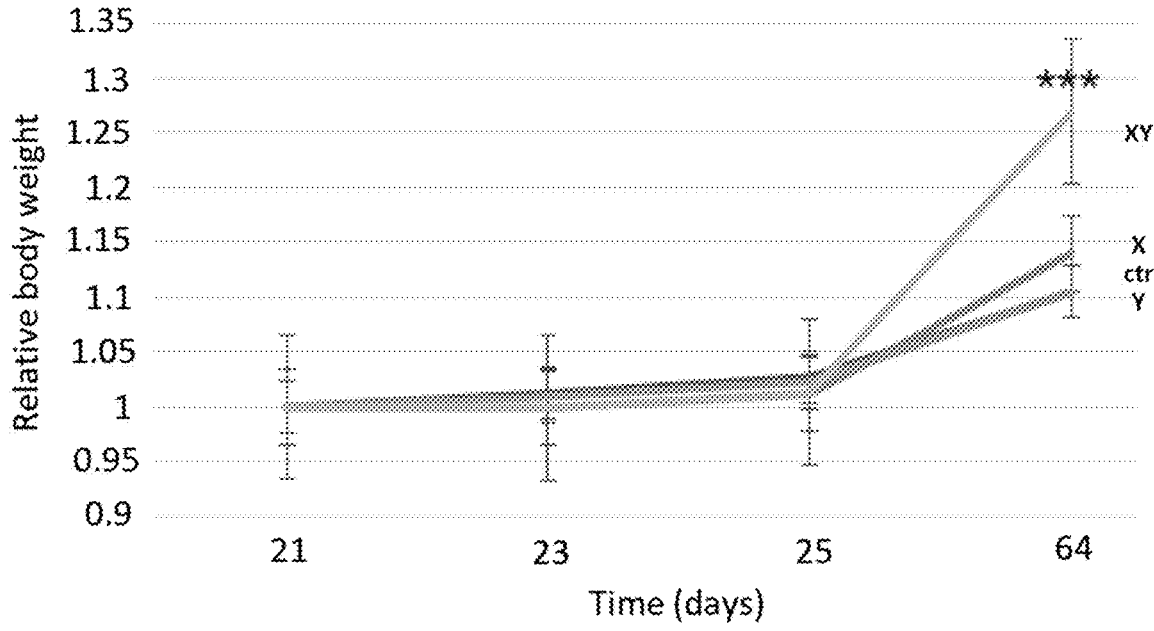
FIG. 40-FIG. 40 shows that drug combination X and Y increased total body mass significantly, compared to the aged control animals with muscle wasting and sarcopenia, indicating X and Y reversed sarcopenia.

Daily oral gavage of the drug combination X (20 mg/kg) and Y (4 mg/kg), relative to X alone (20 mg/kg) or Y alone (4 mg/kg) or the vehicle (DMSO in phosphate buffered saline or PBS) over 6 weeks, led to increases in anti-aging-associated tissue regeneration in 1 year-old aged diabetic mice. In their livers with aging-associated steatohepatitis, X and Y promoted liver regeneration, as observed from increased hepatocyte proliferation indicated by Ki67 (Abcam ab16667) immunostaining (FIG. 34). In their pancreas with aging-associated pancreatitis due to type 2 diabetes, X and Y decreased β islet fibrosis according to Masson's trichrome staining (FIG. 35) and increased β islet cell growth and proliferation according to Ki67 (Abcam ab16667) immunostaining (FIGS. 36A and 36B) and qRT-PCR for Pax6, Mafa, Pdx1 and Ins using primers from Origene (FIGS. 37A and 37B), thereby promoting pancreatic β islet regeneration. In their skin, after shaving and wounding with dorsal skin punches (10 mm diameter), X and Y promoted both aged hair regeneration and wound healing by 64 days (FIG. 38). In their quadriceps muscles, X and Y increased the protein levels of myosin heavy chain (MHC; Sigma-Aldrich-M4276 antibody) (FIG. 39), thereby promoting skeletal muscle regeneration. Moreover, total body mass increased significantly, compared to the aged control animals with muscle wasting and sarcopenia, indicating X and Y reversed sarcopenia (FIG. 40). None of these beneficial anti-aging effects were observed with either X alone or Y alone or the vehicle control.

Figures 41, 42:
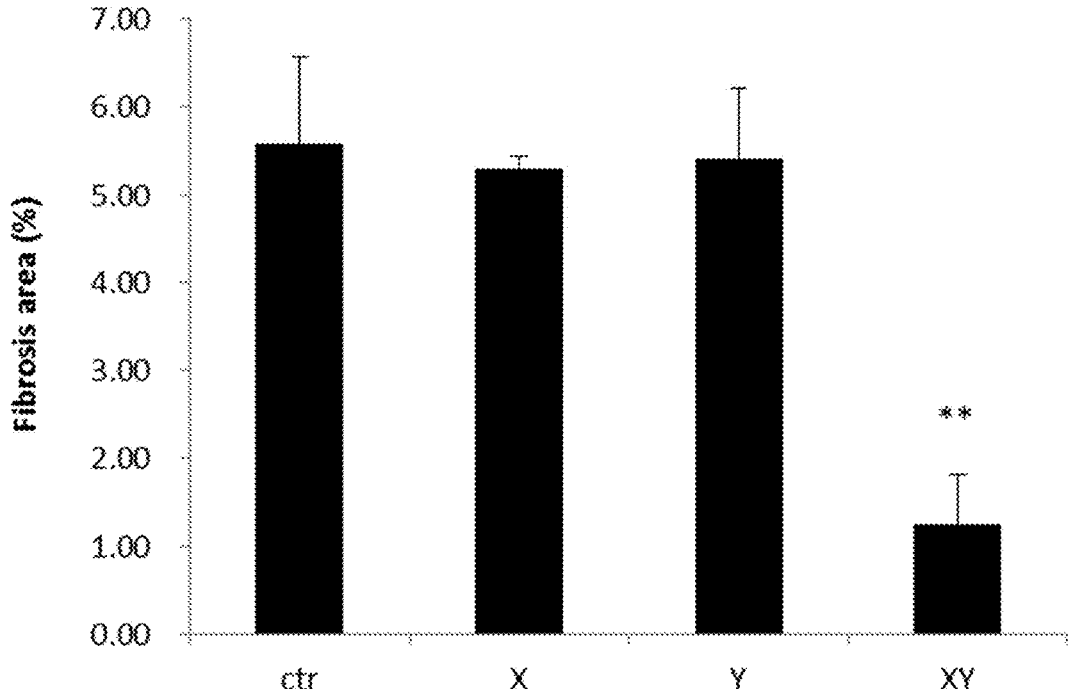
FIG. 41-FIG. 41 shows that daily oral gavage of the drug combination X and Y, relative to X alone or Y alone or the vehicle over 3 weeks, led to decreases in aging-associated lung fibrosis in 1 year-old aged mice treated with intratracheal bleomycin (3 mg/kg in 50 ul phosphate buffered saline or PBS) to model chronic obstructive pulmonary disease (COPD) and idiopathic pulmonary fibrosis (IPF).
FIG. 42-FIG. 42 shows that drug combination X and Y restored estrus cycles in most of female rats (PCOS rat models), based on vaginal smear analysis.

Daily oral gavage of the drug combination X and Y, relative to X alone or Y alone or the vehicle over 3 weeks, led to decreases in aging-associated lung fibrosis in 1 year-old aged mice treated with intratracheal bleomycin (3 mg/kg in 50 ul phosphate buffered saline or PBS) to model chronic obstructive pulmonary disease (COPD) and idiopathic pulmonary fibrosis (IPF). Masson trichrome staining and ImageJ (NIH) quantification of the % fibrotic area revealed that lungs of mice treated with X and Y had significantly lower levels of fibrosis (FIG. 41). None of these beneficial anti-aging effects were observed with either X alone or Y alone or the vehicle control.

Daily oral gavage of the drug combination X and Y, relative to X alone or Y alone or the vehicle over 6 weeks, led to restoration of estrus cycles in adult female rats treated with subcutaneous dehydroepiandrosterone (DHEA; 60 mg/kg body weight) and fed with a high fat-high sugar-high cholesterol diet ad libitum to model premature ovarian aging in polycystic ovary syndrome (PCOS). Vaginal smear analysis revealed that most of the female rats treated with X and Y had restored estrus cycles (FIG. 42). None of these beneficial anti-aging effects were observed with either X alone or Y alone or the vehicle control, where all of the rats were frozen in either the estrus or proestrus stages.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A method of treating at least one of the following conditions in a subject in need thereof: Lung Fibrosis, Chronic Obstructive Pulmonary Disease (COPD), and Idiopathic Pulmonary Fibrosis (IPF), wherein the method comprises administering to the subject an effective amount of a pharmaceutical composition that comprises a combination of therapeutic agent X and acceptable salts thereof and therapeutic agent Y and acceptable salts thereof, and wherein the therapeutic agent X is 2-acetoxybenzoic acid and the therapeutic agent Y is 1-[(2,3,4-trimethoxyphenyl) methyl]piperazine.

2. A method of treating a Chronic Wound in a subject in need thereof, wherein the method comprises administering to the subject an effective amount of a pharmaceutical composition that comprises a combination of therapeutic agent X and acceptable salts thereof and therapeutic agent Y and acceptable salts thereof, and wherein the therapeutic agent X is 2-acetoxybenzoic acid and the therapeutic agent Y is 1-[(2,3,4-trimethoxyphenyl)methyl]piperazine.

3. The method of claim 2, wherein the Chronic Wound is a result of Diabetes.

4. A method of treating Hair Loss in a subject in need thereof, wherein the method comprises administering to the subject an effective amount of a pharmaceutical composition that comprises a combination of therapeutic agent X and acceptable salts thereof and therapeutic agent Y and acceptable salts thereof, and wherein the therapeutic agent X is 2-acetoxybenzoic acid and the therapeutic agent Y is 1-[(2, 3,4-trimethoxyphenyl)methyl]piperazine.

5. A method of treating Sarcopenia in a subject in need thereof, wherein the method comprises administering to the subject an effective amount of a pharmaceutical composition that comprises a combination of therapeutic agent X and acceptable salts thereof and therapeutic agent Y and acceptable salts thereof, and wherein the therapeutic agent X is 2-acetoxybenzoic acid and the therapeutic agent Y is 1-[(2, 3,4-trimethoxyphenyl)methyl]piperazine.

6. A method of reducing senescence in a tissue or organ in a subject in need thereof, wherein the method comprises administering to the subject an effective amount of a pharmaceutical composition that comprises a combination of therapeutic agent X and acceptable salts thereof and therapeutic agent Y and acceptable salts thereof, and wherein the therapeutic agent X is 2-acetoxybenzoic acid and the therapeutic agent Y is 1-[(2,3,4-trimethoxyphenyl)methyl]piperazine.

7. A method of reversing fibrosis in a tissue or organ in a subject in need thereof, wherein the method comprises administering to the subject an effective amount of a pharmaceutical composition that comprises a combination of therapeutic agent X and acceptable salts thereof and therapeutic agent Y and acceptable salts thereof, and wherein the therapeutic agent X is 2-acetoxybenzoic acid and the therapeutic agent Y is 1-[(2,3,4-trimethoxyphenyl)methyl]piperazine.

8. The method according to any one of claims 1-7, wherein therapeutic agent X and therapeutic agent Y are included in separate dosage forms.

9. The method according to any one of claims 1-7, wherein therapeutic agent X and therapeutic agent Y are included in a single dosage form.

* * * * *